US008987209B2

(12) United States Patent
Lerchen et al.

(10) Patent No.: US 8,987,209 B2
(45) Date of Patent: Mar. 24, 2015

(54) N-CARBOXYALKYL-AURISTATIN AND THE USE THEREOF

(75) Inventors: Hans-Georg Lerchen, Leverkusen (DE); Sherif El Sheikh, Essen (DE); Beatrix Stelte-Ludwig, Wülfrath (DE); Sven Golfier, Berlin (DE); Joachim Schuhmacher, Wuppertal (DE); Jean Mark Gnoth, Mettmann (DE); Ursula Krenz, Leichlingen (DE)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 13/876,777

(22) PCT Filed: Sep. 26, 2011

(86) PCT No.: PCT/EP2011/066658
§ 371 (c)(1),
(2), (4) Date: Jun. 12, 2013

(87) PCT Pub. No.: WO2012/041805
PCT Pub. Date: Apr. 5, 2012

(65) Prior Publication Data
US 2013/0261064 A1    Oct. 3, 2013

(30) Foreign Application Priority Data

Sep. 29, 2010  (EP) ..................................... 10181966
Mar. 16, 2011  (EP) ..................................... 11158466

(51) Int. Cl.
| C07K 5/00   | (2006.01) |
| C07K 7/02   | (2006.01) |
| A61K 38/08  | (2006.01) |
| C07K 1/107  | (2006.01) |
| C07K 5/02   | (2006.01) |
| A61K 38/07  | (2006.01) |
| A61K 45/06  | (2006.01) |
| A61K 38/00  | (2006.01) |

(52) U.S. Cl.
CPC . *C07K 7/02* (2013.01); *A61K 38/00* (2013.01); *A61K 38/08* (2013.01); *C07K 1/1077* (2013.01); *C07K 5/0205* (2013.01); *A61K 38/07* (2013.01); *A61K 45/06* (2013.01)
USPC .......................................... 514/19.3; 530/330

(58) Field of Classification Search
None
See application file for complete search history.

(56) References Cited

U.S. PATENT DOCUMENTS

| 6,884,869 | B2 | 4/2005  | Senter et al.   |
| 7,498,298 | B2 | 3/2009  | Doronina et al. |
| 7,553,816 | B2 | 6/2009  | Senter et al.   |
| 7,659,241 | B2 | 2/2010  | Senter et al.   |
| 8,288,352 | B2 | 10/2012 | Doronina et al. |
| 8,343,928 | B2 | 1/2013  | Doronina et al. |
| 8,609,105 | B2 | 12/2013 | Senter et al.   |
| 8,722,629 | B2 | 5/2014  | Lerchen et al.  |
| 2002/0147138 | A1 | 10/2002 | Firestone et al. |
| 2009/0111756 | A1 | 4/2009  | Doronina et al. |
| 2009/0280056 | A1 | 11/2009 | Dennis et al.   |
| 2013/0066055 | A1 | 3/2013  | Lerchen et al.  |
| 2013/0095123 | A1 | 4/2013  | Lerchen et al.  |
| 2013/0122024 | A1 | 5/2013  | Lerchen et al.  |
| 2013/0157960 | A1 | 6/2013  | Lerchen et al.  |
| 2014/0080763 | A1 | 3/2014  | Lerchen et al.  |
| 2014/0127240 | A1 | 5/2014  | Lerchen et al.  |

FOREIGN PATENT DOCUMENTS

| WO |    96/18408 A1 | 6/1996  |
| WO |    99/35164 A1 | 7/1999  |
| WO | WO 01/18032 A2 | 3/2001  |
| WO | WO 02/088172 A2 | 11/2002 |
| WO |    03/008378 A1 | 1/2003  |
| WO |    03/026577 A2 | 4/2003  |
| WO |  2004/010957 A2 | 2/2004  |
| WO | WO 2004/010957 A2 | 2/2004 |
| WO | WO 2005/081711 A2 | 9/2005 |
| WO |  2006/132670 A2 | 12/2006 |
| WO | WO 2007/008603 A1 | 1/2007 |
| WO | WO 2007/008848 A1 | 1/2007 |
| WO | WO 2008/052187 A2 | 5/2008 |
| WO | WO 2009/117531 A1 | 9/2009 |
| WO |  2011/154359 A1 | 12/2011 |
| WO |  2012/041805 A1 | 4/2012  |
| WO |  2012/123423 A1 | 9/2012  |
| WO |  2012/143495 A2 | 10/2012 |
| WO |  2012/143496 A2 | 10/2012 |
| WO |  2012/143497 A2 | 10/2012 |
| WO |  2012/143499 A2 | 10/2012 |
| WO |  2013/087716 A2 | 6/2013  |

OTHER PUBLICATIONS

Nelson et al., Ann. Intern Med. 2009; 151:727-737.*
Kataja et al., Ann Oncol 2009; 20(sup 4): iv10-14.*
Balmana et al. Ann Oncol 2009; 20(supp 4):iv19-20.*
International Search Report (Form PCT/ISA/210) issued on Aug. 18, 2011, by the European Patent Office in International Application No. PCT/EP2011/059300. (4 pages).

(Continued)

*Primary Examiner* — Sheela J Huff
(74) *Attorney, Agent, or Firm* — Buchanan Ingersoll & Rooney PC

(57) ABSTRACT

The present application relates to new derivatives of monomethylauristatin F, substituted on the N terminus by a carboxyalkyl group, processes for preparing these derivatives, their use for the treatment and/or prevention of diseases and to produce medication for the treatment and/or prevention of diseases, particularly hyperproliferative and/or angiogenic disorders such as cancer disorders, for example. Such treatments can occur as monotherapies or in combination with other medication or further therapeutic measures.

16 Claims, No Drawings

(56) References Cited

OTHER PUBLICATIONS

International Search Report (Form PCT/ISA/210) issued on Apr. 17, 2012, by the European Patent Office in corresponding International Application No. PCT/EP2012/054294. (9 pages).
Notification Concerning Transmittal of International Preliminary Report on Patentability (Forms PCT/IB/326 and PCT/IB/373) and the Written Opinion of the International Searching Authority (Form PCT/ISA/237) issued on Dec. 20, 2012, by the International Bureau of WIPO in International Application No. PCT/EP2011/059300. (10 pages).
Arap et al., "Cancer Treatment by Targeted Drug Delivery to Tumor Vasculature in a Mouse Model" Science, (Jan. 16, 1998), vol. 279, No. 5349, pp. 377-380.
Bajjuri et al., "The Legumain Protease-Activated Auristatin Prodrugs Suppress Tumor Growth and Metastasis without Toxicity" ChemMedChem, (Jan. 3, 2011), vol. 6, Issue 1, pp. 54-59.
Doronina et al., "Enhanced Activity of Monomethylauristatin F through Monoclonal Antibody Delivery: Effects of Linker Technology on Efficacy and Toxicity" Bioconjugate Chemistry, (Jan.-Feb. 2006), vol. 17, No. 1, pp. 114-124.
Doronina et al., "Novel Peptide Linkers for Highly Potent Antibody-Auristatin Conjugate" Bioconjugate Chemistry, (Oct. 2008), vol. 19, No. 10, pp. 1960-1963.
Ducry et al., "Antibody-Drug Conjugates: Linking Cytotoxic Payloads to Monoclonal Antibodies" Bioconjugate Chemistry, (Jan. 2010), vol. 21, No. 1, pp. 5-13.
Karkan et al., "A Unique Carrier for Delivery of Therapeutic Compounds Beyond the Blood-Brain Barrier" PLoS One, (Jun. 25, 2008), vol. 3, Issue 6, pp. 1-14. (e2469).
Lambert, "Drug-Conjugated Monoclonal Antibodies for the Treatment of Cancer" Current Opinion in Pharmacology, (Oct. 2005), vol. 5, No. 5, pp. 543-549.
Pettit et al., "Antineoplastic Agents 365. Dolastatin 10 SAR Probes" Anti-Cancer Drug Design, (Jun. 1998), vol. 13, No. 4, pp. 243-277.
Pettit, "The Dolastatins" Prog. Chem. Org. Nat. Prod. (1997), vol. 70, pp. 1-79.
Pettit et al., "Antineoplastic Agents 337. Synthesis of Dolastatin 10 Structural Modifications" Anti-Cancer Drug Design, (Oct. 1995), vol. 10, No. 7, pp. 529-544.
Senter, "Potent Antibody Drug Conjugates for Cancer Therapy" Current Opinion in Chemical Biology, (Jun. 2009), vol. 13, No. 3, pp. 235-244.
Wu et al., "Arming Antibodies: Propects and Challenges for Immunoconjugates" Nature Biotechnology, (Sep. 2005), vol. 23, No. 9, pp. 1137-1146.
Lerchen et al., U.S. Appl. No. 14/004,699, entitle "N-Carboxyalkyl-Auristatin and the Use Thereof" filed Nov. 19, 2013.
International Search Report (PCT/ISA/210) issued on Nov. 8, 2011, by the European Patent Office as the International Searching Authority for International Application No. PCT/EP2011/066658.
Written Opinion (PCT/ISA/237) issued on Nov. 8, 2011, by the European Patent Office as the International Searching Authority for International Application No. PCT/EP2011/066658.
Lerchen et al., U.S. Appl. No. 14/269,577, entitled "Novel Binder-Drug Conjugates (ADCS) and Use Threof" filed May 5, 2014.
Lerchen et al., U.S. Appl. No. 14/364,203, entitled "New Antibody Drug Conjugates (ADCS) and the Use Thereof" National Stage Entry of PCT/EP2012/075277, (2012).

\* cited by examiner

N-CARBOXYALKYL-AURISTATIN AND THE USE THEREOF

The present application relates to new derivatives of monomethylauristatin F, substituted on the N terminus by a carboxyalkyl group, processes for preparing these derivatives, their use for the treatment and/or prevention of diseases and to produce medication for the treatment and/or prevention of diseases, particularly hyper proliferative and/or antigenic disorders such as cancer disorders, for example. Such treatments can occur as monotherapies or in combination with other medication or further therapeutic measures.

Cancer disorders are the result of uncontrolled cell growths in a wide variety of tissues. In many cases, new cells penetrate existing tissue (invasive growth), or they metastasize into remote organs. Cancers occur in a wide variety of organs and often progress in a tissue-specific manner. For this reason, the term "cancerous disorder" refers to a large group of defined diseases of different organs, tissues and cell types.

Early-stage tumors may be removed using surgical or radio therapeutic measures. Metastasized tumors are usually treated as palliative care only using chemotherapeutic agents. The main goal here is to find the optimal combination between improving the quality of life and prolonging life.

The majority of parenterally administered chemotherapeutic agents used nowadays are often not specifically aimed at the tumor tissue or the tumor cells, but are distributed non-specifically in the body because of their systemic administration, thus, also in places where exposure to the drug is undesirable, for example in healthy cells, tissues and organs. This can lead to undesirable side-effects up to and including general effects of toxicity, which often limits the therapeutically usable dosage of the drug and can even lead to cessation of medication.

The improved and selective availability of these chemotherapeutic agents in the tumor cell or the surrounding tissue has been the focus of the development of new chemotherapeutic agents for years, not only to maximize the effect of the drug but also to minimize toxic side-effects. Efficient methods for administering the drug directly into the target cell have been attempted many times. Optimizing the association between drug and intracellular target and minimizing intracellular drug distribution, for example into neighboring cells, is still proving a difficult task.

Monoclonal antibodies, for example, are suitable for specific targeting of tumor tissues and tumor cells. The significance of these antibodies for the clinical treatment of cancerous disorders has increased significantly in the last few years, based on the effectiveness of agents such as trastuzumab (Herceptin), rituximab (Rituxan), cetuximab (Erbitux) and bevacizumab (Avastin), which are all licensed for the therapy of individual, specific tumor disorders [see for example, G. P. Adams and L. M. Weiner, Nat. Biotechnol. 23, 1147-1157 (2005)]. As a consequence of this, the interest in so called immunoconjugates has increased significantly. An internalizing antibody directed against a tumor-associated antigen is joined covalently via a linking unit ("linker") to a cytotoxic agent. After being introduced into the tumor cell and separated from the conjugate, it can then work directly and selectively. Doing this could potentially reduce the damage of normal tissue significantly compared to conventional chemotherapy of cancerous disorders [see for example J. M. Lambert, Curr. Opin. Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducey and B. Stump, Bioconjugate Chem. 21, 5-13 (2010)].

Instead of antibodies, one could also use ligands from the small-molecule drug range which selectively bind to a specific target, such as a receptor [see for example E. Ruoslahti et al., Science 279, 377-380 (1998); D. Karkan et al., PLoS ONE 3 (6), e2469 (Jun. 25, 2008)]. Conjugates made from a cytotoxic drug and addressing ligand, which reveal a clear cleavage site between ligand and drug to release the active drug, are also known. Such a "predetermined break point" can exist in a peptide chain, which can be cleaved selectively at a specific location by a specific enzyme at the required location [see for example R. A. Firestone and L. A. Telan, US Patent Application US 2002/0147138].

Auristatin E (AE) and monomethylauristatin E (MMAE) are synthetic analogues of dolastatines, a specific group of linear pseudopeptides, which were originally isolated from marine sources and which have partly shown very potent cytotoxic activity towards tumor cells [for a review see for example G. R. Pettit, Prog. Chem. Org. Nat. Prod. 70, 1-79 (1997); G. R. Pettit et al., Anti-Cancer Drug Design 10, 529-544 (1995); G. R. Pettit et al., Anti-Cancer Drug Design 13, 243-277 (1998)].

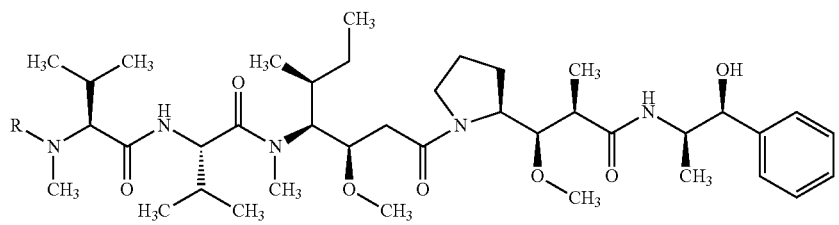

Auristatin E (AE): R = CH₃
Monomethylauristatin E (MMAE): R = H

However, MMAE has unfortunately comparatively high systemic toxicity. Furthermore, using an antibody/active agent-conjugate (immunoconjugate) is incompatible with linkers between antibodies and active compound with an enzymatically predetermined breaking point. [S. O. Doronina et al., Bioconjugate Chem. 17, 114-124 (2006)].

Monomethylauristatin F (MMAF) is an auristatin derivative with a C-terminal phenylalanine unit which shows only moderate anti-proliferate activity compared to MMAE. It is very likely that this can be attributed to the free carboxyl group whose polarity and charge adversely affects its ability to access cells. In this context the methyl ester of MMAF (MMAF-OMe) has been described as a neutrally charged prodrug derivative with ability to access cells, which has shown in vitro toxicity towards a variety of carcinoma cell lines which is higher by several orders of magnitude compared to MMAF [S. O. Doronina et al., Bioconjugate Chem. 17, 114-124 (2006)]. It can be assumed that this effect is caused by MMAF itself, which is released quickly via intracellular ester hydrolysis after the prodrug has been introduced into the cells.

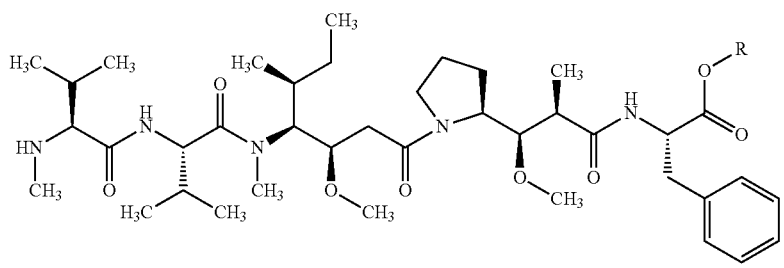

Monomethylauristatin F (MMAF): R = H
Monomethylauristatin F-methylester (MMAF—OMe): R = CH₃

However, drug compounds based on simple ester derivatives are generally exposed to the risk of chemical instability due to non-specific ester hydrolysis which is independent of the intended site of action, for example with esterases which occur in blood plasma; this can restrict the usefulness of these compounds for therapeutic purposes significantly. Furthermore, auristatin derivatives such as MMAE and MMAF are also substrates for transporter proteins, which are expressed by many tumor cells, which can lead to the development of resistance against these drugs.

Starting with only moderately effective monomethylauristatin F (MMAF), it was thus the intention of the present invention to identify new connections and make these available especially for the therapy of cancerous diseases, which show significantly higher cytotoxic activity in whole-cell assays on the one hand and reduced substrate properties for transporter proteins on the other. Such substances could be particularly suitable as toxophores to connect with proteins such as antibodies, or possibly with ligands of low molecular weights, to form anti-proliferative (immuno-) conjugates.

Monomethylauristatin F (MMAF) and several ester and amide derivatives thereof have already been disclosed in WO 2005/081711-A2. Several other auristatin analogues with a C-terminal, amidically substituted phenylalanine unit are described in WO 01/18032-A2. In WO 02/088172-A2 and WO 2007/008603-A1, MMAF analogues are described in which the side-chain of the phenylalanine is modified and WO 2007/008848-A2, describes analogues, in which the carboxyl group of the phenylalanine is modified. Further auristatin conjugates which are connected with the N- or C-terminal are described in WO 2004/010957-A2 and WO 2009/117531-A1, amongst others [see also S. O. Doronina et al., *Bioconjugate Chem.* 19, 1960-1963 (2008)].

Object of the present invention are compounds of the general formula (I)

Wherein
L stands for a straight-chain $(C_1\text{-}C_{12})$-alkandiyl, which may be substituted with methyl up to four times and in which (a) two carbon atoms may be connected to each other in 1,2-, 1,3- or 1,4 relation, if necessary including carbon atoms that are located between them to form a $(C_3\text{-}C_6)$-cycloalkyl-ring or a phenyl ring or (b) up to three $CH_2$ groups not adjacent to each other may be substituted for an O, $R^1$ stands for hydrogen or methyl, $R^2$ stands for isopropyl, isobutyl, sec.-butyl, tert.-butyl, 1-hydroxyethyl, phenyl, benzyl, 4-hydroxybenzyl, 1-phenylethyl, diphenylmethyl, 1H-imidazol-4-ylmethyl or 1H-indol-3-ylmethyl, Or $R^1$ and $R^2$, together with the carbon atom to which they are both connected, form a 2-phenylcyclopropan-1,1-diyl group of the formula

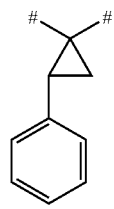

Wherein
\# marks the points of attachment with other parts of the molecule,

And

T stands for a group with formula $-C(=O)-OR^3$, $-C(=O)-NR^4R^5$, $-C(=O)-NH-NH-R^6$ or $-CH_2-O-R^7$ in which $R^3$ stands for hydrogen, $(C_1\text{-}C_6)$-alkyl or $(C_3\text{-}C_{10})$-cycloalkyl, Where $(C_1\text{-}C_6)$-alkyl may be substituted with phenyl, naphthyl or $(C_3\text{-}C_{10})$-cycloalkyl, (I)

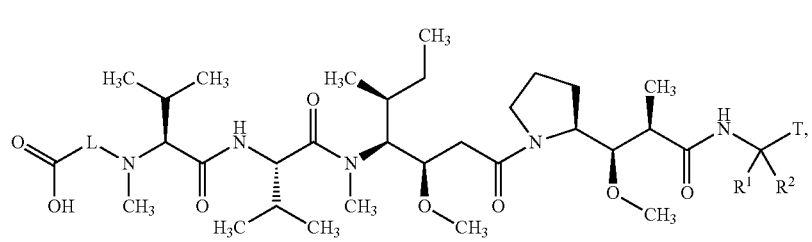

R⁴ stands for hydrogen or $(C_1-C_6)$-alkyl,

R⁵ stands for hydrogen, $(C_1-C_6)$-alkyl or $(C_3-C_{10})$-cycloalkyl,

Where $(C_1-C_6)$-alkyl may be substituted with phenyl,

Or

R⁴ and R⁵ are connected to each other and, together with the nitrogen atom they are attached to, form a 5- to 7-membered, saturated aza-heterocyclic compound, which may contain a further ring-heteroatom such as >N—H, >N—CH₃ or —O—; and are located either at the 1,3- or 1,4-location in relation to the aforementioned nitrogen atom, R⁶ stands for $(C_1-C_6)$-alkyl, $(C_1-C_6)$-alkylcarbonyl, phenyl or benzoyl, And R⁷ stands for $(C_1-C_6)$-alkyl, which may be substituted with phenyl, Where phenyl may also be substituted with $(C_1-C_6)$-alkoxycarbonyl or carboxyl, and also their salts, solvates and solvates of the salts.

Compounds of the invention are compounds of formula (I) and its salts, solvates and solvates of the salts, the compounds of the formulas mentioned below encompassing formula (I) and their salts, solvates and solvates of the salts, and the compounds encompassing formula (I) which will be subsequently introduced as working examples and their salts, solvates and solvates of the salts, assuming that the subsequently mentioned compounds are not already salts, solvates and solvates of the salts.

Depending on their structure, the compounds of the invention may exist in different stereoisomeric forms, i.e. in the form of configurative isomers or, if appropriate, in the form of conformational isomers (enantiomers and/or diastereomers, including atropisomers). The present invention thus includes enantiomers and diastereomers and their respective composites. Stereoisomerically homogeneous components may be extracted in the usual manner from such composites of enantiomers and/or diastereomers; preferably, this will be achieved using chromatographic processes, in particular, HPLC chromatography in an achiral or chiral phase.

If the compounds of the invention exist in tautomeric forms, the present invention encompasses all tautomeric forms.

Salts that are preferred in the context of the present invention are physiologically harmless salts of the compounds of the invention. Salts which are not suitable for pharmaceutical uses are also included as these can be used for isolating or purifying compounds of the invention.

Physiologically harmless salts of the compounds of the invention include acid addition salts of mineral acids, carboxylic acid and sulphonic acids, such as salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically harmless salts of the compounds of the invention also include salts of the common bases such as, and preferably, alkali metal salts (e.g. sodium and potassium salts), alkaline earth metal salts (e.g. calcium and magnesium salts) and ammonium salts, derived from ammonia or organic amines with 1 to 16 C atoms, such as, and preferably, ethylamine, diethylamine, triethylamine, N,N-diisopropylethylamine, monoethanolamine, diethanolamine, trisethanolamine, dimethylaminoethanol, diethylaminoethanol, procaine, dicyclohexylamine, dibenzylamine, N-methylpiperidine, N-methylmorpholine, arginine, lysine and 1,2-ethylendiamine.

In the context of this invention such forms of the compounds of the invention are referred to as solvates which form a complex by coordination with solvent molecules either in their solid or liquid state. Hydrates are a special form of solvates in which the coordination occurs with water. In the context of the present invention, hydrates are preferred as solvates.

Furthermore, the present invention also includes prodrugs of the compounds of the invention. The term "prodrugs" here refers to compounds which may be biologically active or inactive, but are converted into compounds of the invention during their time in the body (for example metabolically or through hydrolysis).

In the context of the present invention, the substituents, unless otherwise specified, are defined as follows:

$(C_1-C_6)$-alkyl and $(C_1-C_4)$-alkyl here represent a straight-chain or branched alkyl radical with 1 to 6 and 1 to 4 carbon atoms, respectively. A straight-chain or branched alkyl radical with 1 to 4 carbon atoms is preferred here. By way of example and preference, the following are mentioned: methyl, ethyl, n-propyl, isopropyl, n-butyl, isobutyl, sec.-butyl, tert.-butyl, n-pentyl, 2-pentyl, 3-pentyl, neopentyl, n-hexyl, 2-hexyl and 3-hexyl.

$(C_1-C_6)$-alkylcarbonyl and $(C_1-C_4)$-alkylcarbonyl, in the context of the invention, represent a straight-chain or branched alkyl radical with 1 to 6 and 1 to 4 carbon atoms, respectively, which is connected via a carbonyl group [—C(=O)—]. A straight-chain or branched alkylcarbonyl group with 1 to 4 carbon atoms in the alkyl radical is preferred here. By way of example and preference, the following are mentioned: acetyl, propionyl, n-butyryl, iso-butyryl, n-pentanoyl, pivaloyl, n-hexanoyl and n-heptanoyl.

$(C_1-C_6)$-alkoxy and $(C_1-C_4)$-alkoxy, in the context of the invention, represent a straight-chain or branched alkoxy radical with 1 to 6 and 1 to 4 carbon atoms, respectively. A straight-chain or branched alkoxy radical with 1 to 4 carbon atoms is preferred here. By way of example and preference, the following are mentioned: methoxy, ethoxy, n-eropoxy, isopropoxy, n-butoxy, tert-butoxy, n-pentoxy and n-hexoxy.

$(C_1-C_6)$-alkoxycarbonyl and $(C_1-C_4)$-alkoxycarbonyl, in the context of the invention, represent a straight-chain or branched alkoxy radical with 1 to 6 and 1 to 4 carbon atoms, respectively, which is connected through a carbonyl group [—C(=O)—] via the oxygen atom. A straight-chain or branched alkoxycarbonyl group with 1 to 4 carbon atoms in the alkoxy radical is preferred here. By way of example and preference, the following are mentioned: methoxycarbonyl, ethoxycarbonyl, n-propoxycarbonyl, isopropoxycarbonyl, n-butoxycarbonyl, tert-butoxycarbonyl, n-pentoxycarbonyl and n-hexoxycarbonyl.

$(C_1-C_{12})$-alkanediyl, $(C_1-C_8)$-alkanediyl and $(C_1-C_6)$-alkanediyl here represent a straight-chain α,ω-divalent alkyl radical with 1 to 12, 1 to 8 and 1 to 6 carbon atoms, respectively. A straight-chain alkanediyl group with 1 to 8, but especially 1 to 6 carbon atoms is preferred here. By way of example and preference, the following are mentioned: methylene, ethane-1,2-diyl(1,2-ethylene), propane-1,3-diyl(1,3-propylene), butane-1,4-diyl(1,4-butylene), pentane-1,5-diyl (1,5-pentylene), hexane-1,6-diyl(1,6-hexylene), heptane-1,7-diyl(1,7-hexylene), octane-1,8-diyl(1,8-octylene), nonane-1,9-diyl(1,9-nonylene), decane-1,10-diyl(1,10-decylene), undecane-1,11-diyl(1,11-undecylene) and dodecane-1,12-diyl(1,12-dodecylene).

$(C_3-C_6)$-cycloalkyl, in the context of the invention, represents a monocyclic, saturated cycloalkyl group with 3 to 6 carbon atoms. By way of example and preference, the following are mentioned: cyclopropyl, cyclobutyl, cyclopentyl and cyclohexyl.

$(C_3-C_{10})$-cycloalkyl, in the context of the invention, represents a monocyclic, or if necessary, a bi- or tricyclic, saturated cycloalkyl group with 3 to 10 carbon atoms. By way of example and preference, the following are mentioned: cyclopropyl, cyclobutyl, cyclopentyl, cyclohexyl, cycloheptyl, cyclooctyl, cyclononyl, cyclodecyl, hexahydroindanyl, decalinyl, bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decyl, bicyclo[4.3.1]decyl and adamantyl.

In the context of the invention, a 5- to 7-membered azaheterocycle represents a monocyclic, saturated heterocycle with 5 to 7 ring atoms altogether, which contains one nitrogen ring atom, with which it is also connected and which may further contain another ring heteroatom from the following >N—H, >N—CH$_3$ or —O—, which is located at the 1,3- or, if necessary, in the 1,4-position in relation to the aforementioned nitrogen ring atom. By way of example and preference, the following are mentioned: pyrrolidinyl, 1,3-oxazolidinyl, piperidinyl, piperazinyl, N-methylpiperazinyl and morpholinyl.

In the context of the present invention, all radicals which occur more than once have meaning independently of each other. If radicals in the compounds of the inventions are substituted, the radicals can be substituted once or several times, unless otherwise specified. A substitution with one or two identical or several substituent(s) is preferred. Substitution with one substituent is particularly preferred.

In the context of the present invention, preference is given to compounds of formula (I) in which L stands for a straight-chain (C$_1$-C$_8$)-alkandiyl, in which (a) two carbon atoms are linked to each other in 1,3 or 1,4 relation including one or two carbon atoms located between them to form a phenyl ring or (b) up to two CH$_2$ groups not adjacent to each other which may be substituted for an O, R$^1$ stands for hydrogen, R$^2$ stands for benzyl, 4-hydroxybenzyl, 1-phenylethyl or 1H-indol-3-ylmethyl, Or R$^1$ and R$^2$, together with the carbon atom to which they are both connected, form a 2-phenylcyclopropan-1,1-diyl group of the formula

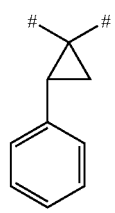

Wherein marks the points of attachment with other parts of the molecule,

And

T stands for a group with formula —C(=O)—OR$^3$, —C(=O)—NR$^4$R$^5$, —C(=O)—NH—NH—R$^6$ or —CH$_2$—O—R$^7$ in which R$^3$ stands for hydrogen or (C$_1$-C$_4$)-alkyl, which may be substituted with phenyl, naphthyl or (C$_3$-C$_{10}$)-cycloalkyl, R$^4$ stands for hydrogen or methyl, R$^5$ stands for hydrogen or (C$_1$-C$_4$)-alkyl, which may be substituted with phenyl, Or R$^4$ and R$^5$ are connected to each other and together with the nitrogen atom they are attached to, form a piperidine- or morpholine ring, R$^6$ stands for (C$_1$-C$_4$)-alkylcarbonyl or benzoyl, And R$^7$ stands for (C$_1$-C$_4$)-alkyl or benzyl, which, in the phenyl group, may be substituted with (C$_1$-C$_4$)-alkoxycarbonyl or carboxyl, and also their salts, solvates and solvates of the salts.

In the context of the present invention, compounds of formula (I) are particularly preferred, in which L stands for a straight-chain (C$_1$-C$_6$)-alkandiyl, R$^1$ stands for hydrogen, R$^2$ stands for benzyl, 1-phenylethyl or 1-H-indol-3-ylmethyl, Or R$^1$ and R$^2$, together with the carbon atom they are both attached to form a (1S,2R)-2-phenylcyclopropan-1,1-diyl group of the formula

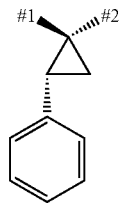

Wherein

1 marks the point of attachment with the adjacent nitrogen atom

And

2 marks the point of attachment of group T,

And

T stands for a group with formula —C(=O)—OR$^3$, —C(=O)—NR$^4$R$^5$, —C(=O)—NH—NH—R$^6$ or —CH$_2$—O—R$^7$ in which R$^3$ stands for hydrogen, methyl, ethyl, n-propyl, benzyl or adamantylmethyl, R$^4$ stands for hydrogen or methyl, R$^5$ stands for hydrogen, methyl, ethyl, n-propyl or benzyl, R$^6$ stands for benzoyl, And R$^7$ stands for benzyl, which may be substituted with methoxycarbonyl or carboxyl in the phenyl group, and also their salts, solvates and solvates of the salts.

In the context of the present invention, compounds of formula (IA) are of particular importance

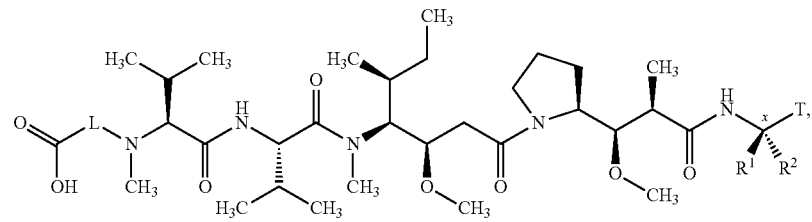

(I-A)

in which L, $R^1$, $R^2$ and T are defined as above and that the radicals $R^1$ and $R^2$ supporting $C^X$-carbon atom has the pictured configuration,
and also their salts, solvates and solvates of the salts.

In the context of the present invention, compounds of formulas (I) and (IA) are also of particular importance, in which L stands for propane-1,3-diyl,
and also their salts, solvates and solvates of the salts.

Independently of the respective combinations of the radicals given, the specific radical definition given in the respective or preferred combinations of radicals are also replaced by radical definitions of other combinations. Particular preference is given to two or more of the preferred ranges given above.

The present invention also provides a process to prepare compounds of the invention of formula (I), characterized in that a compound of formula (II)

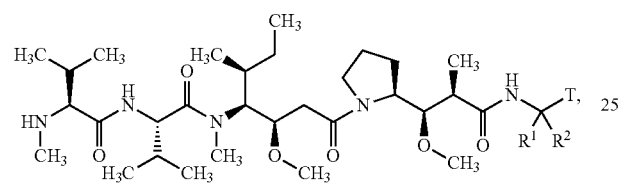
(II)

in which $R^1$, $R^2$ and T are defined as above, is coupled in an inert solvent either by

[A] base-induced alkylation with a compound of formula (III)

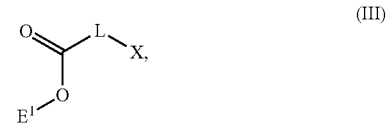
(III)

Wherein L is defined as above, $E^1$ stands for hydrogen, $(C_1-C_4)$-alkyl or benzyl, And X stands for a leaving group such as chloride, bromide, iodide, mesylate, triflate or tosylate, to a compound of formula (IV)

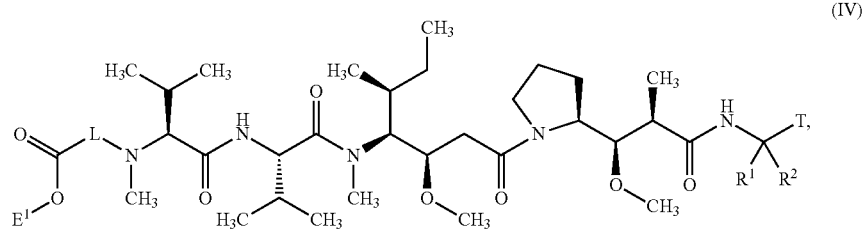
(IV)

Wherein $E^1$, L, $R^1$, $R^2$ and T are defined as above, and then, should $E^1$ stand for $(C_1-C_4)$-alkyl or benzyl, this ester radical is split off using common methods, so that, just as in the event in which $E^1$ in (III) stands for hydrogen, the carboxylic acid according to the invention of formula (I)

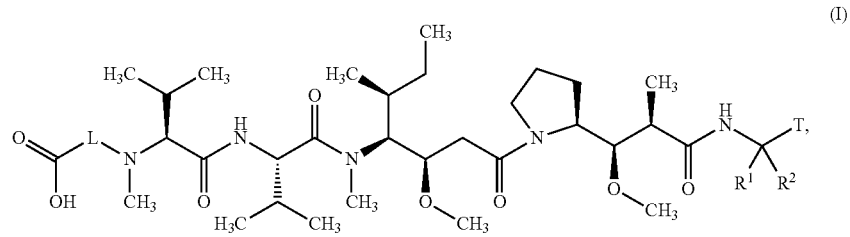
(I)

in which L, $R^1$, $R^2$ and T are defined as above,
is preserved,
Or
[B] by treatment with a compound of formula (V)

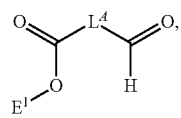

Wherein
$E^1$ stands for hydrogen, $(C_1-C_4)$-alkyl or benzyl,
And
$L^A$ is defined as L above, however its alkyl chain-length is shortened by one $CH_2$-unit,
in the presence of a suitable reducing agent to a compound of formula (VI)

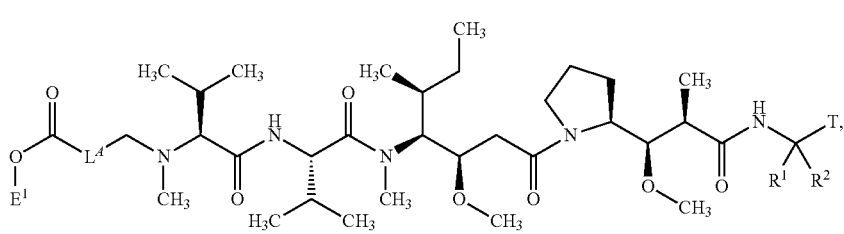

Wherein $E^1$, $L^A$, $R^1$, $R^2$ and T are defined as above,
and then, should $E^1$ stand for $(C_1-C_4)$-alkyl or benzyl, this ester radical is split off using common methods, so that, just as in the case in which $E^1$ in (V) stands for hydrogen, the carboxylic acid which complies with the invention of (I-B)

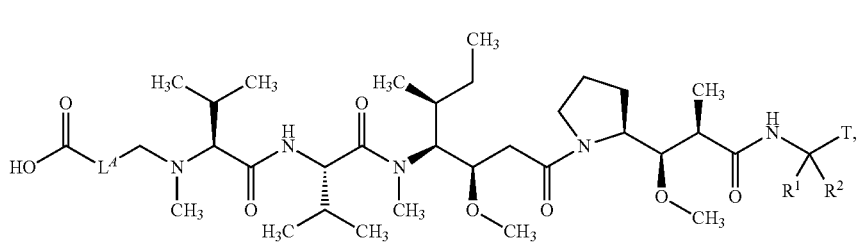

in which $L^A$, $R^1$, $R^2$ and T are defined as above,
is preserved,
And the resulting compounds of formula (I) and (I-B) may be, as required, separated into their enantiomers and/or diastereomers and/or converted using appropriate (i) solvents and/or (ii) bases or acids into their solvates, salts and/or solvates of the salts.

Suitable inert solvents for the coupling reaction (II)+(III)→(IV) are for example ether such as diethylether, diisopropylether, methyl-tert.-butylether, tetrahydrofuran, 1,4-dioxane, 1,2-dimethoxyethane or bis-(2-methoxyethyl)-ether, hydrocarbons such as benzene, toluene, xylene, pentane, hexane, heptane, cyclohexane or mineral oil fractions, or dipolar aprotic solvents such as acetone, methyl ethyl ketone, acetonitrile, dimethyl sulphoxide (DMSO), N,N-dimethylformamide (DMF), N,N-dimethylacetamide (DMA), N,N'-dimethyl propylene urea (DMPU), N-methylpyrrolidinone (NMP) or pyridine. It is also possible to use mixtures of these solvents. Acetone or N,N-dimethylformamide is preferred.

Suitable bases for the alkylation reaction are in particular alkali hydroxides such as lithium, sodium or potassium hydroxide, alkali or alkaline earth metal carbonates, such as lithium, sodium, potassium, calcium or cesium carbonate or usual organic amines, such as triethylamine, N-methylmorpholine, N-methylpiperidine, N,N-diisopropylethylamine, pyridine or 4-N,N-dimethylaminopyridine. Potassium or cesium carbonates are preferred. If necessary, it is advantageous to add an alkylation catalyst, such as lithium bromide or -iodide, sodium or potassium iodide, tetra-n-butylammoniumbromide or -iodide or benzyltriethylammoniumbromide.

The reaction (II)+(III)→(IV) is usually performed in a temperature range of between −20° C. and +100° C., and preferably between 0° C. and +50° C. The reaction can be carried out at atmospheric, elevated or reduced pressure (e.g. between 0.5 and 5 bar); usually, the reaction is carried out at atmospheric pressure.

The reaction (II)+(V)→(VI) is usually carried out in solvents which are standard for reductive amination and inert under the reaction conditions, if necessary with the addition of an acid and/or a dehydrating agent as catalyst. Such solvents are for example alcohols such as methanol, ethanol, n-propanol, isopropanol, n-butanol or tert.-butanol, ether such as tetrahydrofuran, 1,4-dioxan, 1,2-dimethoxyethan or bis-(2-methoxyethyl)-ether, or other solvents such as dichlormethane, 1,2-dichlorethane, N,N-dimethylformamide or water. It is also possible to use mixtures of these solvents. A 1,4-dioxane/water mixture is used preferentially under addition of acetic acid or diluted hydrochloric acid as a catalyst.

Suitable reducing agents for this reaction are particularly complex borohydrides, such as sodium borohydride, sodium cyanoborohydride, sodium triacetoxyborohydride or tetra-n-butylammoniumborohydride. Sodium cyanoborohydride is preferred.

The reaction (II)+(V)→(VI) is usually performed at a temperature range of between −0° C. and +120° C., and preferably in a range of between +50° C. and +100° C. The reaction can be carried out at atmospheric, elevated or reduced pressure (e.g. between 0.5 and 5 bar); usually, the reaction is carried out at atmospheric pressure.

The cleavage of the ester radical $E^1$ in steps (IV)→(I) and (VI)→(I-B) [$E^1$=($C_1$-$C_4$)-alkyl or benzyl] is performed using standard procedures, by treating an ester with an acid or a base in an inert solvent, and by treating the developing carboxylate salt with an acid to produce the free carboxylic acid in the latter case. In the case of tert.-butyl esters the cleavage occurs via an acid. In the case of a benzyl ester, the cleavage can be achieved using hydrogenolysis in the presence of a suitable palladium catalyst, such as palladium on activated carbon.

The ester radical $E^1$ produced in reaction (III) and (V) is chosen so that the condition of its cleavage is compatible with those of the corresponding group T in reaction (IV) and (VI).

Suitable bases for ester hydrolysis are standard inorganic bases. These include in particular alkali or earth metal alkali hydroxides such as lithium hydroxide, sodium hydroxide, potassium hydroxide or barium hydroxide, or alkali and earth metal alkali carbonates such as sodium carbonates, potassium carbonates or calcium carbonates. Lithium hydroxide, sodium hydroxide or potassium hydroxide is preferred.

Suitable acids for ester cleavage are, in general, sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluorimethanesulphonic acid or mixtures thereof, with the addition of water if necessary. In the case of a tert.-butyl ester, hydrogen chloride or trifluoroacetic acid is preferred, and hydrochloric acid in the case of a methyl ester.

Suitable inert solvents for these reactions are water or standard organic solvents used for ester cleavage. Preferably, these include lower alcohols such as methanol, ethanol, n-propanol or isopropanol, ether such as diethylether, tetrahydrofuran, 1,4-dioxane or 1,2-dimethoxyethane, or other solvents such as dichlormethane, acetone, methyl ethyl ketone, N,N-dimethylformamide or dimethyl sulphoxide. It is also possible to use mixtures of these solvents. In the case of basic ester hydrolysis, mixtures of water with 1,4-dioxane, tetrahydrofuran, methanol, ethanol and/or dimethylformamide are preferred. In the case of a reaction with trifluoroacetic acid, dichloromethane is preferred and in the case of reaction with hydrogen chloride, tetrahydrofurane, diethyl ether, 1,4-dioxane or water is preferred.

Ester cleavage is generally performed in a temperature range between −20° C. to +100° C., preferably between 0° C. to +50° C.

The compounds of formula (II) can, for instance, be produced using standard procedures of peptide chemistry by coupling a compound of formula (VII)

(VII)

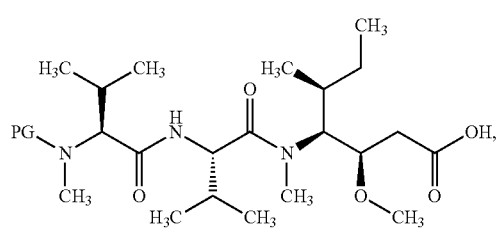

Wherein

PG stands for an amino protection group such as (9H-fluoren-9-ylmethoxy)carbonyl, tert.-butoxycarbonyl or benzyloxycarbonyl, in an inert solvent under the activation of the carboxyl function in (VII) either

[C] at first with a compound of formula (VIII)

(VIII)

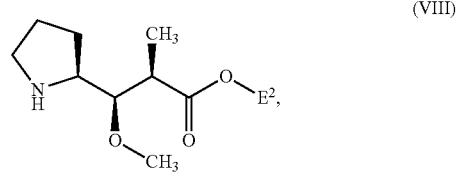

Wherein $E^2$ stands for hydrogen, ($C_1$-$C_4$)-alkyl or benzyl, or a salt of this compound with a compound of formula (IX)

(IX)

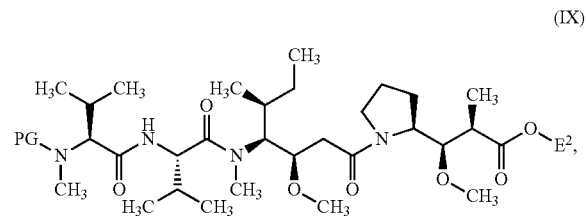

In which $E^2$ and PG are defined as above, and then, should $E^2$ stand for ($C_1$-$C_4$)-alkyl or benzyl, cleave off the ester radical using standard procedures, and then couple the resulting carboxylic acid of formula (X)

(X)

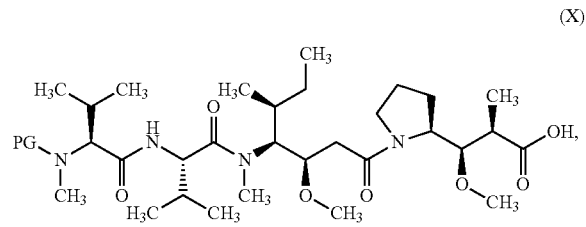

Wherein PG, defined as above, is then coupled in an inert solvent by means of activating the carboxyl function with a compound of formula (XI)

(XI)

In which $R^1$, $R^2$ and T, defined as above, or a salt of this compound to a compound of formula (XII)

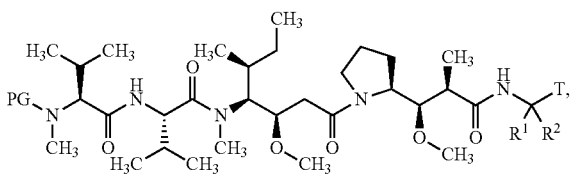
(XII)

Wherein PG, $R^1$, $R^2$ and T, defined as are coupled

Or

[D] with a compound of formula (XIII)

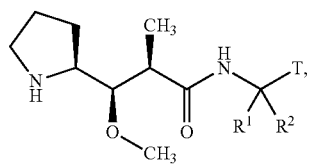
(XIII)

In which $R^1$, $R^2$ and T, defined as above, or with a salt of this compound to a compound of formula (XII)

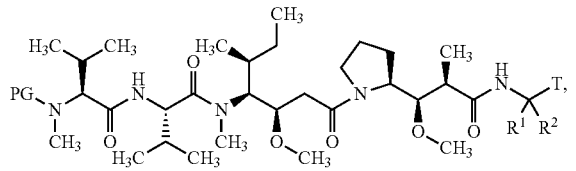
(XII)

Wherein PG, $R^1$, $R^2$ and T, defined as above, are coupled and the compound of formula (XII) is then deprotected to a compound of formula (II) in the usual manner

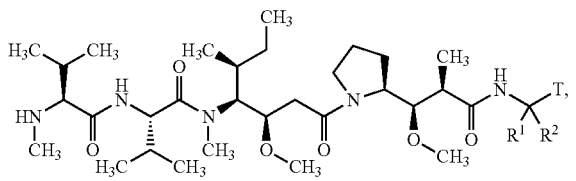
(II)

Wherein $R^1$, $R^2$ and T are defined as above, are deprotected.

The coupling reactions described above (i.e. the formation of amides from respective amine and carboxylic acid components) are performed using standard procedures of peptide chemistry [see for example. M. Bodanszky, *Principles of Peptide Synthesis*, Springer-Verlag, Berlin, 1993; M. Bodanszky and A. Bodanszky, *The Practice of Peptide Synthesis*, Springer-Verlag, Berlin, 1984; H.-D. Jakubke and H. Jeschkeit, *Aminosäuren, Peptide, Proteine*, Verlag Chemie, Weinheim, 1982].

Inert solvents for the coupling reactions (VII)+(VIII)→(IX), (X)+(XI)→(XII) and (VII)+(XIII)→(XII) are for example ethers such as diethyl ether, diisopropyl ether, tert.-butylmethylether, tetrahydrofuran, 1,4-dioxane, 1,2-dimethoxyethane or bis-(2-methoxyethyl)-ether, hydrocarbons such as benzene, toluene, xylene, pentane, hexane, heptane, cyclohexane or mineral oil fractions, halogenated hydrocarbons such as dichloromethane, trichloromethane, tetrachloromethane, 1,2-dichloroethane, trichloroethylene or chlorobenzene, or dipolar aprotic solvents such as acetone, methyl ethyl ketone, acetonitrile, ethyl acetate, pyridine, dimethyl sulphoxide (DMSO), N,N-dimethylformamide (DMF), N,N-dimethylacetamide (DMA), N,N'-dimethylpropylene urea (DMPU) or N-methylpyrrolidinon (NMP). It is also possible to use mixtures of these solvents. N,N-dimethylformamide is preferred.

Suitable activating/condensing agents for these couplings are for example carbodiimides such as N,N'-diethyl-, N,N'-diisopropyl-, N,N'-dicyclohexylcarbodiimide (DCC) or N-(3-dimethylaminoisopropyl)-N'-ethylcarbodiimid-hydrochloride (EDC), phosgene derivates such as N,N'-carbonyldiimidazole (CDI) or isobutylchloroformiat, 1,2-oxazolium-compounds such as 2-ethyl-5-phenyl-1,2-oxazolium-3-sulfate or 2-tert.-butyl-5-methylisoxazolium-perchlorate, acylamino-compounds such as 2-ethoxy-1-ethoxycarbonyl-1,2-dihydrochinoline, α-chlorenamines such as 1-chloro-2-methyl-1-dimethylamino-1-propene, phosphor-compounds such as propanephosphonic acid anhydride, cyanophosphonic acid diethyl ester, bis-(2-oxo-3-oxazolidinyl)-phosphorylchloride, benzotriazole-1-yloxy-tris(dimethylamino)phosphonium-hexafluorophosphate or benzotriazole-1-yloxy-tris(pyrrolidino)phosphonium-hexafluorophosphate (PyBOP) or uronium-compounds such as O-(benzotriazole-1-yl)-N,N,N'N'-tetramethyluronium-tetrafluoroborate (TBTU), O-(benzotriazole-1-yl)-N,N,N',N'-tetramethyluronium-hexafluorophosphate (HBTU), 2-(2-oxo-1-(2H)-pyridyl)-1,1,3,3-tetramethyluronium-tetrafluoroborate (TPTU), O-(7-azabenzotriazole-1-yl)-N,N,N,N-tetramethyluronium-hexafluorophosphate (HATU) or O-(1H-6-chlorbenzotriazole-1-yl)-1,1,3,3-tetramethyluronium-tetrafluoroborate (TCTU), if necessary in combination with the aid of 1-hydroxybenzotriazole (HOBt) or N-hydroxysuccinimide (HOSu), or, as bases, alkali-carbonates, for example, sodium or potassium carbonate or tertiary amine such as triethylamine, N-methylmorpholine, N-methylpiperidine, N,N-diisopropylethylamine, pyridine or 4-N,N-dimethylaminopyridine.

In the context of the present invention, N-(3-dimethylaminoisopropyl)-N'-ethylcarbodiimid-hydrochloride (EDC) in combination with 1-hydroxybenzotriazole (HOBt) and N,N-diisopropylethylamine, or O-(7-azabenzotriazole-1-yl)-N,N,N',N'-tetramethyluronium-hexafluorophosphate (HATU) in connection with N,N-diisopropylethylamine are the preferred activating/condensation agents for these coupling reactions.

The coupling reactions (VII)+(VIII)→(IX), (X)+(XI)→(XII) and (VII)+(XIII)→(XII) are generally performed in a temperature range of between −20° C. and +60° C., preferably between 0° C. and +40° C. The reactions can be carried out at atmospheric, elevated or reduced pressure (e.g. between 0.5 and 5 bar); usually, the reactions are carried out at atmospheric pressure.

If necessary, existing functional groups—particularly amino, hydroxyl and carboxyl groups can be present in temporarily protected forms in the steps described here, if functional or necessary. The introduction and removal of such protection groups is done using standards methods of peptide chemistry. [See for example, T. W. Greene and P. G. M. Wuts, *Protective groups in Organic Synthesis*, Wiley, New York, 1999; M. Bodanszky and A. Bodanszky, *The Practice of Peptide Synthesis*, Springer-Verlag, Berlin, 1984]. Where several protected groups are present, they may be simultaneously liberated in a one-pot reaction or liberated in separate reaction steps.

The preferred amino-protection group is tert.-butoxycarbonyl (Boc), benzyloxycarbonyl (Z) or (9H-fluoren-9-ylmethoxy)carbonyl (Fmoc); for a hydroxyl or carboxyl function, tert.-butyl or benzyl are the preferred protection groups. The removal of a tert.-butyl- or tert.-butoxycarbonyl group is typically achieved by treatment with a strong acid, such as, hydrogen chloride, hydrogen bromide or trifluoroacetic acid, in an inert solvent such as diethylether, 1,4-dioxane, dichloromethane or acetic acid: if necessary, this reaction can take place without the addition of an inert solvent. If the protection group is benzyl or benzyloxycarbonyl, these are preferably removed through hydrogenolysis in the presence of a suitable palladium catalyst, such as palladium on activated carbon. The (9H-fluoren-9-ylmethoxy)carbonyl group is usually removed using a secondary amine base such as diethylamine or piperidine.

An ester radical $E^2$ in compound (VIII) [$E2=(C_1-C_4)$-alkyl or benzyl] is chosen so that the conditions of its cleavage are compatible with the particular protection group from compound (VII).

The compounds of formula (VII) can be produced in an analogous manner, by firstly, coupling N-(benzyloxycarbonyl)-L-valine of formula (XIV)

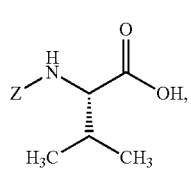

(XIV)

Wherein Z stands for the benzyloxycarbonyl protection group,
with the aid of a condensation agent to a compound of formula (XV)

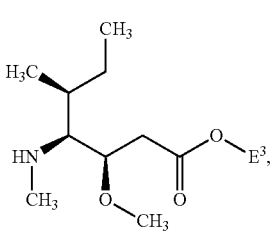

(XV)

Wherein $E^3$ stands for an $(C_1-C_4)$-alkyl, or a salt of this compound to a compound of formula (XVI)

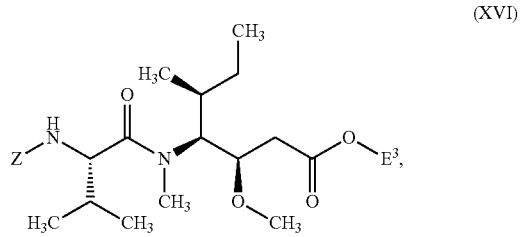

(XVI)

Wherein $E^3$ and Z are defined as above, is coupled, after removing the Z-protection group with hydrogenolysis, in the presence of a condensation agent with N-protective N-methyl-L-valine of formula (XVII)

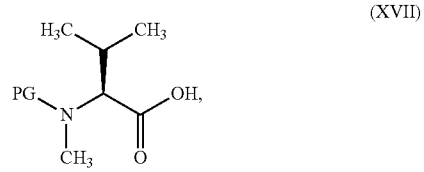

(XVII)

Wherein

PG stands for an amino protection group such as (9H-fluoren-9-ylmethoxy)carbonyl, tert.-butoxycarbonyl or benzyloxycarbonyl, to a compound of formula (XVIII)

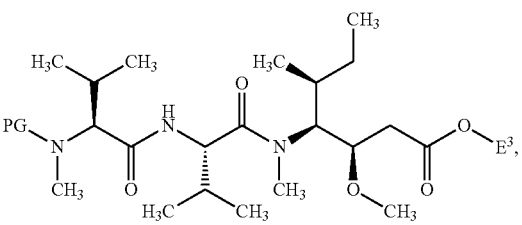

(XVIII)

Wherein $E^3$ and PG are defined as above, and finally transfer the ester group —C(O)O-$E^3$ in (XVIII) converted in the free carboxyl acid (VII) using standard procedures.

The coupling reactions (XIV)+(XV)→(XVI) and Z-deprotected (XVI)+(XVII)→(XVIII) are performed under analogous reaction conditions as described in steps [C] and [D].

The hydrolysis of ester group —C(O)O-$E^3$ in step (XVIII)→(VII) is performed in an analogous manner has been described in steps [A] and [B] for the ester radical $E^1$. The alkyl group $E^3$ in compound (XV) is chosen here so that its cleavage conditions are compatible with the chosen protection group PG from compound (XVII).

The compounds of formula (XIII) themselves are accessible through coupling of compound (XI) described above with compound (XIX)

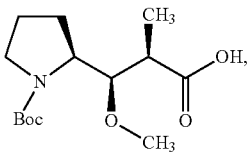

(XIX)

Wherein Boc stands for tert.-butoxycarbonyl protection group,
to a compound of formula (XX)

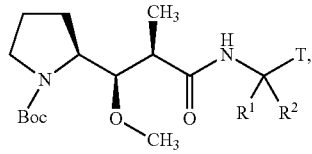

(XX)

Wherein Boc, $R^1$, $R^2$ and T are defined as above,
and accessible for subsequent cleavage of the Boc protection group.

The coupling reaction (XI)+(XIX)→(XX) is carried out under analogous conditions as has been described on the coupling steps of procedures [C] and [D].

The compounds of formulas (III), (VIII), (XI), (XIV), (XV), (XVII) and (XIX), respectively, are, where appropriate, commercially available in chiral or diastereomeric forms, or are described as such in the literature, or can be produced by experts in the standard ways, analogous to methods published in the literature. Numerous comprehensive instructions, including literature sources for the production of starting compounds can be found in the experimental part of the section on the production of starting compounds and intermediates.

If the relevant isomerically pure starting compounds are not available, then cleavage of the compounds according to invention into its corresponding enantiomers and/or diastereomers can take place at compound stages (II), (IV), (VI), (XII), (XIII), and (XX), which can then be used further in separated form as described in subsequent reaction steps. The cleavage of stereoisomers can be done by an expert using the standard methods. Chromatographic processes on achiral and chiral separation phases is preferred; in the case of free carboxyl groups, as intermediates, cleavage can be achieved via diastereomeric salts with the aid of chiral bases.

The production of compounds of the invention can be visualized using the following schemes:

Scheme 1

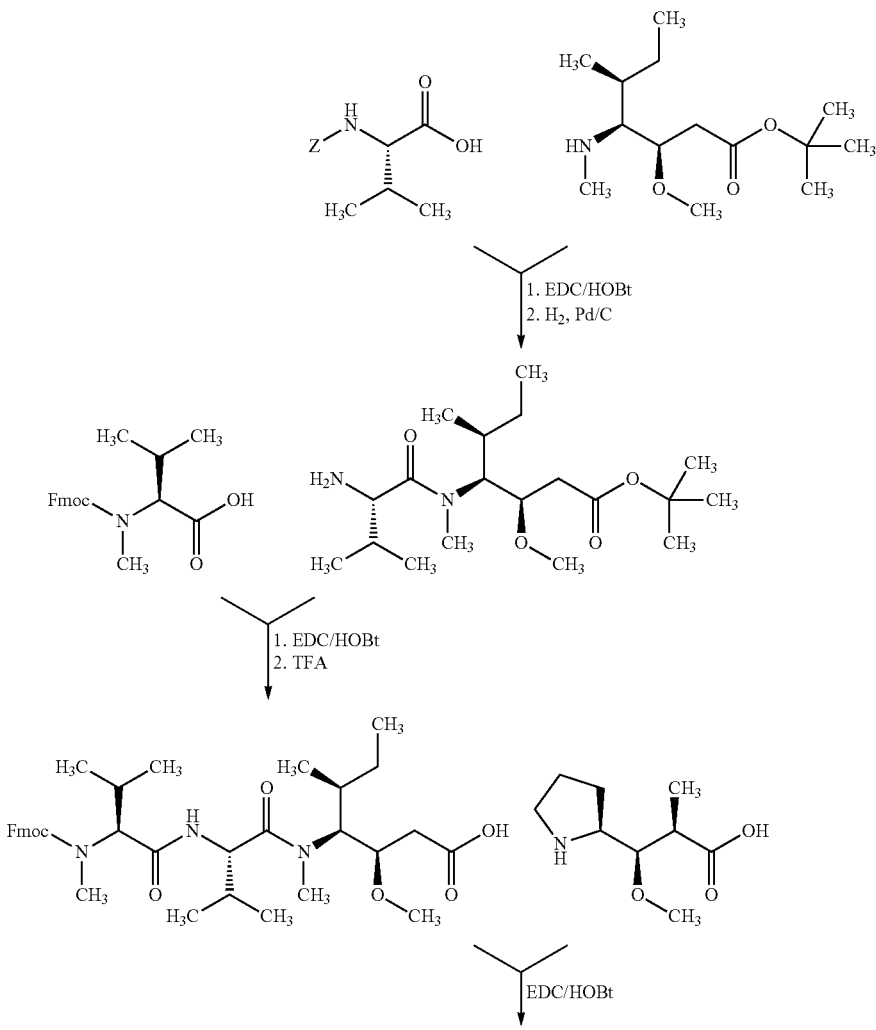

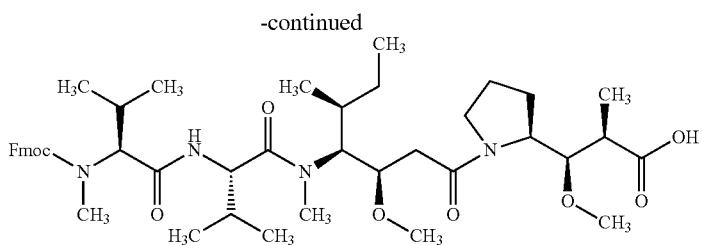
Scheme 2
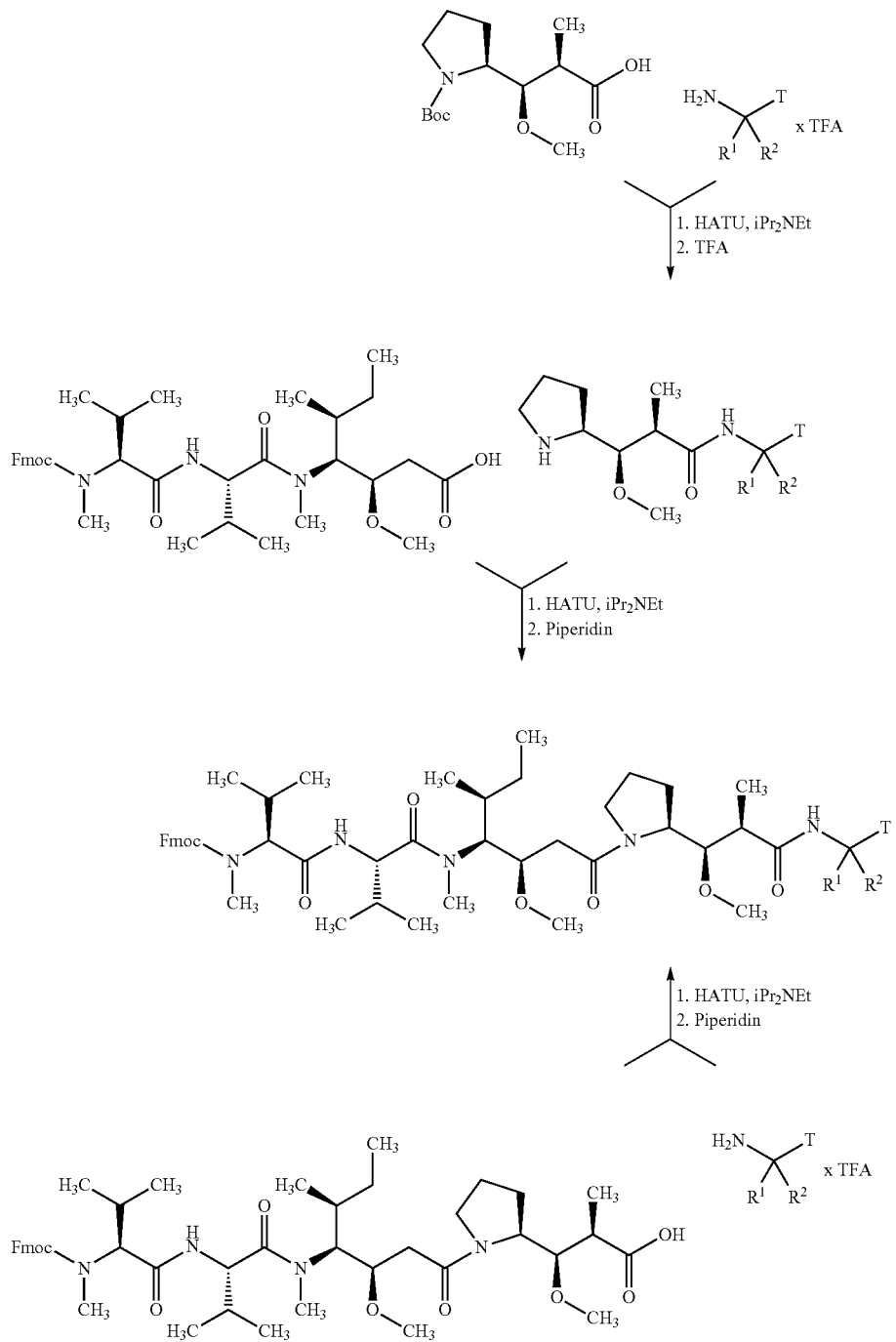

Scheme 3
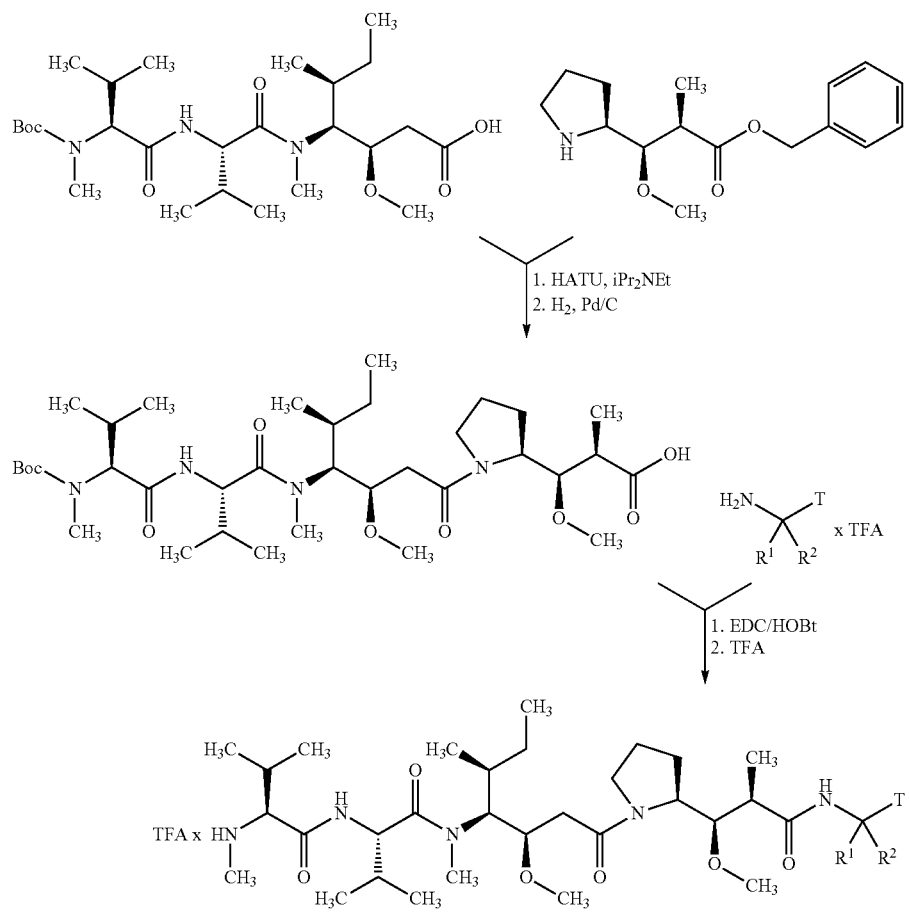
Scheme 4
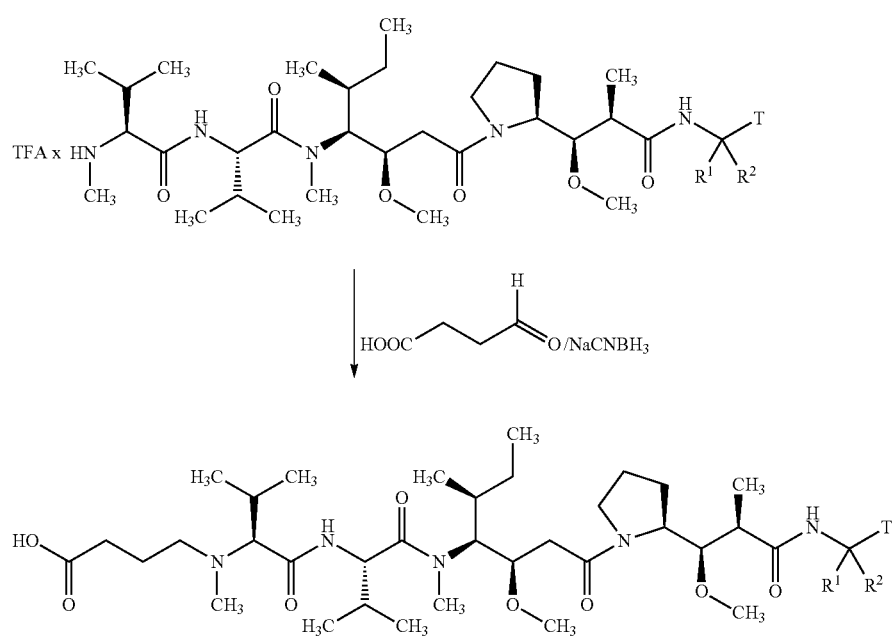

The compounds of the invention possess valuable pharmacological properties and can be used for the treatment and prevention of disease in humans and animals.

Compared to other well-known auristatin derivatives, the N-terminal carboxyalkyl group [HOOC-L- in formula (I)], which is contained in compounds of the present invention, does not only function as a linker for the potential connection with antibody proteins or other ligands, but also proves to be a constitutive structural element which has surprisingly advantageous properties for these compounds.

Compared to, say monomethylauristatin F (MMAF), the compounds of the present invention show much stronger cytotoxic activity, but at the same time, also show a much lower potential for acting as substrates for cellular transporter proteins.

Thus, the compounds of the invention are particularly suited to the treatment of hyper proliferative diseases in humans and mammals in general. On the one hand, the compounds can hinder, block, lessen or reduce cell proliferation and cell division, but also increases apoptosis.

The hyper proliferative diseases which can be treated with the compounds of the invention are cancerous and tumor disorders, in particular. In the context of the present invention, these include, amongst others: Mammary carcinomas and mammary tumors (ductal and lobular forms, also in situ), tumors of the respiratory tract (parvicellular and non-parvicellular carcinoma, bronchial carcinoma), brain tumors (e.g. of the brain stem and hypothalamus, astrocytoma, ependymoma, glioblastoma, glioma, medulloblastoma, meningioma and also neuro-ectodermal and pineal tumors), tumors of the digestive organs (esophagus, stomach, gall bladder, small and large intestine, rectum and anus), tumors of the liver (such as hepatocellular carcinoma, cholangiocellular carcinoma and mixed- and cholangio-cellular carcinoma), tumors of the head and neck region (larynx, hypopharynx, nasopharynx, oropharynx, lips and oral cavity, oral melanoma), skin tumors (basalioma, spinalioma, squamos epithelial carcinoma, Kaposi sarcoma, malignant melanoma, non-malignant skin cancer, Markel cell carcinoma, mast cell tumors), tumors of the soft tissues (such as soft tissue sarcoma, osteosarcoma, malignant fibrous histiocytoma, chondrosarcoma, fibrosarcoma, hemangiosarcoma, leiomyosarcoma, liposarcoma and rhabdomyosarcoma), tumors of the eyes (such as intra-ocular melanoma and retinoblastoma), tumors of endrocrine and exocrine glands (e.g. thyroid and parathyroid glands, pancreas and salivary glands, adenocarcinoma), tumors of the urinary tract (bladder, penis, kidneys, renal pelvis and ureter) and tumors of the reproductive organs (endometrium, cervical, ovarian, vaginal, vulvar and uterus carcinoma in women and prostate and testicular carcinoma in men). This also includes proliferative diseases of the blood, the lymphatic system and of the spinal cord, in solid form and as circulating cells, such as leukemias, lymphomas and myeloproliferative diseases, e.g. acute, myeloid, acute, lymphoblastic, chronic lymphocytic, chronic myelogenic and hairy cell leukemia, and also AIDS-related lymphomas, Hodgkin's lymphoma, non-Hodgkin's lymphoma, cutaneous T-cell lymphomas, Burkitt lymphomas and lymphomas of the central nervous system.

These well-described diseases in humans can exist in other mammals, too, with a comparable etiology, and can also be treated with compounds of the invention there.

The treatment of the above-mentioned cancers with compounds of the invention does not only include solid tumors, but also the treatment of metastasized and circulating forms.

The terms "treatment" and "treat" are used here in their conventional sense, and describe the provision, care and supervision of patients with the aim to fight, lessen, reduce or alleviate a disease or health deviation and to improve quality of life, which has been affected by the disease, as is the case in cancers.

Further point of the present invention is thus the application of the compounds of the invention for treatment and/or prevention of diseases, in particular the above-mentioned diseases.

Further point of the present invention is the application of the compounds of the invention the development of medication for treatment and/or prevention of diseases, in particular the above-mentioned diseases.

Further point of the present invention is thus the application of the compounds for a process for treatment and/or prevention of diseases, in particular the above-mentioned diseases.

Further point of the present invention is the application of the compounds of the invention in a process for treatment and/or prevention of diseases, in particular the above-mentioned diseases, whilst using at least one of the compounds of the invention in a useful quantity.

The compounds of the invention can be used alone or, if necessary, in connection with one or more other pharmacologically useful substances, as long as this combination does not lead to undesirable and unacceptable side-effects. Further point of the present invention is thus medication, which contains at least one of the compounds of the invention and one or more active substances, particularly for the treatment and/or prevention of the above-mentioned diseases.

For example, the compounds of the present invention can be combined with known anti-hyper proliferative, cytostatic or cytotoxic substances for the treatment of cancers. Suitable combination agents are, for example:

aldesleukin, alendronic acid, alfaferone, alitretinoin, allopurinol, aloprim, Aloxi, altretamin, aminoglutethimide, amifostine, amrubicin, amsacrine, anastrozole, anzmet, Aranesp, arglabin, arsenic trioxide, aromasin, 5-azacytidine, azathioprin, BCG or tice-BCG, bestatin, betamethason acetate betamethason sodium phosphate, bexarotene, bleomycin sulphate, broxuridine, bortezomib, busulfan, calcitonin, Campath, capecitabine, carboplatin, Casodex, cefesone, celmoleukin, cerubidin, chlorambucil, cisplatin, cladribin, clodronic acid, cyclophosphamide, cytarabine, dacarbazine, dactinomycin, DaunoXome, Decadron, Decadron phosphate, delestrogen, denileukin diftitox, depomedrol, deslorelin, dexrazoxane, diethylstilbestrol, Diflucan, docetaxel, doxifluridine, doxorubicin, dronabinol, DW-166HC, Eligard, Elitek, Ellence, Emend, epirubicin, epoetin alpha, Epogen, eptaplatin, ergamisol, Estrace, estradiol, estramustin sodium phosphate, ethinylestradiol, Ethyol, etidronic acid Etopophos, etoposide, fadrozol, farstone, filgrastim, finasteride, fligrastim, floxuridine, fluconazol, fludarabin, 5-fluordeoxyuridin monophosphate, 5-fluoruracil (5-FU), fluoxymesterone, flutamide, formestane, fosteabine, fotemustine, fulvestrant, Gammagard, gemcitabine, gemtuzumab, Gleevec, Gliadel, goserelin, granisetron hydrochloride, histrelin, hycamtin, hydrocortone, erythro-hydroxynonyladenine, hydroxyurea, ibritumomab tiuxetan, idarubicin, ifosfamide, interferon-alpha, interferon-alpha-2, interferon-alpha-2α, interferon-alpha-2β, interferon-alpha-n1, interferon-alpha-n3, interferon-beta, interferon-gamma-1α, interleukin-2, intron A, iressa, irinotecan, kytril, lentinan sulphate, letrozol, leucovorin, leuprolide, leuprolide acetate, levamisole, levofolic acid calcium salt, levothroid, levoxyl, lomustine, lonidamine, Marinol, mechlorethamine, mecobalamin, medroxyprogesterone acetate, megestrol acetate, melphalan, Menest, 6-mercaptopurine, mesna, methotrexate, Metvix, miltefosine, minocycline, mitomycin C, mitotane, mitoxantrone, Modrenal, Myocet, nedaplatin, Neulasta, Neumega, Neupogen, nilutamide, Nolvadex, NSC-631570, OCT-43, octreotide, ondansetron hydrochloride, Orapred, oxaliplatin, paclitaxel, Pediapred, pegaspargase, Pegasys, pentostatin, Picibanil, pilocarpine hydrochloride, pirarubicin, plicamycin, porfimer sodium, prednimustine, prednisolone, prednisone, Premarin, procarbazine, Procrit, raltitrexed, Rebif, rhenium-186 etidronate, rituximab, roferon-A, romurtide, Salagen, sandostatin, sargramostim, semustine, sizofiran, sobuzoxane, Solu-Medrol, streptozocin, strontium-89 chloride, Synthroid, tamoxifen, tamsulosin, tasonermin, tastolactone, taxoter, teceleukin, temozolomide, teniposide, testosterone propionate, Testred, thioguanine, thiotepa, thyrotropin, tiludronic acid, topotecan, toremifen, tositumomab, tastuzumab, teosulfan, Tretinoin, Trexall, trimethylmelamine, trimetrexate, triptoreline acetate, triptoreline pamoate, UFT, uridine, valrubicin, vesnarinone, vinblastine, vincristine, vindesine, vinorelbine, Virulizin, Zinecard, zinostatin-stimalamer, Zofran; ABI-007, acolbifen, Actimmun, Affinitak, aminopterin, arzoxifen, asoprisnil, atamestan, atrasentan, avastin, BAY 43-9006 (sorafenib), CCI-779, CDC-501, celebrex, cetuximab, crisnatol, cyproterone acetate, decitabine, DN-101, doxorubicin-MTC, dSLIM, dutasteride, edotecarin, eflornithin, exatecan, fenretinide, histamine dihydrochloride, histrelin hydrogel implant, holmium-166-DOTMP, ibandronic acid, interferon-gamma, ntron-PEG, ixabepilone, keyhole limpet hemocyanine, L-651582, lanreotide, lasofoxifen, libra, lonafarnib, miproxifen, minodronat, MS-209, liposomal MTP-PE, MX-6, nafarelin, nemorubicin, neovastat, nolatrexed, oblimersen, onko-TCS, Osidem, paclitaxe polyglutamate, pamidronate disodium, PN-401, QS-21, quazepam, R-1549, raloxifen, ranpirnas, 13-cis-retic acid, satraplatin, seocalcitol, T-138067, Tarceva, taxoprexin, thymosin-alpha-1, tiazofurin, tipifarnib, tirapazamin, TLK-286, toremifen, transMID-107R, valspodar, vapreotide, vatalanib, verteporfin, vinflunin, Z-100, zoledronic acid, and combinations of these.

In a preferred form, the compounds of the invention can be combined with anti-hyperproliferative agents, which could be one of the following. However, this list is not exclusive: aminoglutethimide, L-asparaginase, azathioprine, 5-azacytidine, bleomycin, busulfan, carboplatin, carmustine, chlorambucil, cisplatin, colaspase, cyclophosphamide, cytarabine, dacarbazine, dactinomycin, daunorubicin, diethylstilbestrol, 2',2'-difluordeoxycytidine, docetaxel, doxorubicin (adriamycin), epirubicin, epothilon and its derivatives, erythro-hydroxynonyladenin, ethinylestradiol, etoposide, fludarabin phosphate, 5-fluordeoxyuridine, 5-fluordeoxyuridine monophosphate, 5-fluoruracil, fluoxymesterone, flutamide, hexamethylmelamine, hydroxyurea, hydroxyprogesterone caproate, idarubicin, ifosfamide, interferon, irinotecan, leucovorin, lomustine, mechlorethamine, medroxyprogesterone acetate, megestrol acetate, melphalan, 6-mercaptopurine, mesna, methotrexate, mitomycin C, mitotane, mitoxantron, paclitaxel, pentostatin, N-phosphonoacetyl L-aspartate (PALA), plicamycin, prednisolone, prednisone, procarbazine, raloxifen, semustine, streptozocin, tamoxifen, teniposide, testosterone propionate, thioguanine, thiotepa, topotecan, trimethylmelamine, uridine, vinblastine, vincristine, vindesine and vinorelbine.

The compounds of the invention can be combined with biological therapeutics such as antibodies (e.g. avastin, rituxan, erbitux, herceptin) in a promising manner. The compounds of the invention also achieve positive effects in combination with therapies that are directed against angiogenesis, such as, for example, avastin, axitinib, recentin, regorafenib, sorafenib or sunitinib. Combinations with inhibitors of proteasomes and of mTOR as well as combinations with antihormones and steroidal metabolic enzyme inhibitors are also particularly suitable because of their advantageous side effect profile.

Generally, the following goals can be pursued when the compounds of the invention are used in combination with other cytostatic or cytotoxic agents:
    increased efficacy in slowing down the growth of the tumor, in the reduction of its size and even in its complete elimination compared to treatment with a single drug;
    the possibility to give chemotherapeutic agents in a lower dosage compared to monotherapies;
    the possibility of a more agreeable therapy with less side-effects compared to single drug administration;
    the possibility of treating a broader spectrum of tumor disorders;
    the achievement of a higher rate of response of the therapy;
    Longer survival rates of patients compared to current standard therapies.

Furthermore, the compounds of the invention can also be used in conjunction with radiotherapy and/or surgical interventions.

A further point of the present invention is medication which contains at least one compound of the invention, usually in connection with one or more inert, non-toxic, pharmaceutically suitable excipients and its use for the purposes named above.

The compounds of the intervention can work systemically and/or locally. To achieve this, they can be applied in a suitable manner, for example, orally, parenterally, pulmonally, nasally, sublingually, lingually, buccally, rectally, dermally, transdermally, conjunctively or via an implant or stent.

For these methods of application, the compounds of the invention can be given in a form suitable for the method of application.

For oral application, the compounds of the invention may be administered using quick and/or modified methods of dispensation, which may contain the compounds in crystalline and/or amorphized and/or soluble form, e.g. tablets (non-coated or coated, for example with coatings resistant to gastric acid or which dissolve in a delayed manner or which do not dissolve, and thus control the release of the compounds of the invention); tablets or films/oblates which dissolve quickly in the mouth, films/lyophylizates, capsules (for example, hard or soft gelatin capsules), pills, granulates, pellets, powders, emulsions, suspensions, aerosols or solutions.

Parenteral application can be achieved by side-stepping an absorption step (e.g. intravenous, intra-arterial, intracardiac or intralumbar) or by utilizing absorption (e.g. intra-muscular, subcutaneous, intracutaneous, percutanous or intraperitoneal). Application forms suitable for parenteral application are, among others, injection and infusion preparations in the form of solutions, suspensions, emulsions, lyophylizates or sterile powders.

For the other methods of applications, one could utilize, for example, inhalation medication (powder inhalers, nebulizers), nasal drops, solution or sprays, tablets, films/oblates or capsules to be applied lingually, sublingually or buccally, suppositories, ear or eye preparations, vaginal capsule, aqueous suspensions (lotions, mixtures which need to be shaken), lipophilic suspensions, salves, creams, transdermal therapeutic systems (e.g. plasters), milk, pastes, foams, sprinkling powders, implants or stents.

Oral and parenteral applications are preferred, particularly oral and intravenous application.

The compounds of the invention can be converted into the methods of application described above. This can be achieved by mixing with inert, nontoxic, pharmaceutically suitable excipients in the standard way. These excipients may be, for example, carrier substances (such as micro crystalline cellulose, lactose, mannitol), solvents (such as liquid polyethylene glycols), emulsifiers and dispersing or wetting agents (such as sodium dodecyl sulphate, polyoxysorbitan oleate), binders (such as polyvinylpyrrolidone), synthetic and natural polymers (such as albumin), stabilizers (e.g. antioxidants such as ascorbic acid), colorants (e.g. inorganic pigments such as iron oxides) and taste and/or odor correctors.

Generally, when using parenteral application, it has proven advantageous to administer doses of ca. 0.001 up to 1 mg/kg, preferably ca. 0.01 up to 0.5 mg/kg of body weight to achieve effective results. For oral applications, the dose is about 0.01 to 100 mg/kg, preferably ca. 0.01 to 20 mg/kg and ideally 0.1 to 10 mg/kg of body weight.

However, it might be necessary to deviate from the doses mentioned above, depending on body weight, method of application, individual behavior towards to active agent, and type of preparation and the time or interval, over which the application takes place. It is possible that in some cases, less than the stated minimum dose is sufficient, whereas in some case, more than the stated maximum does might be required. Should the application of large amounts be required, it might be advisable to distribute these in several smaller doses throughout the day.

The following examples illustrate the invention. The invention is not limited to these examples.

The percentage figures in the following tests and examples, refer to body weight percentages, unless otherwise states; parts are parts by weight. Solvent ratios, dilution ratios and concentration data of liquid/liquid solutions refer to volume.

A. EXAMPLES

Abbreviations and Acronyms
abs. absolute
Ac Acetyl
aq. aqueous, aqueous solution
Boc tert.-butoxycarbonyl
br. broad (in NMR)
Ex. example
ca. circa, approximately
CI chemical ionization (in MS)
d doublet (in NMR)
d day(s)
TLC thin-layer chromatography
DCI direct chemical ionization (in MS)
dd doublet of a doublet (in NMR)
DMAP 4-N,N-dimethylaminopyridine
DME 1,2-dimethoxyethane
DMF N,N-dimethylformamide
DMSO dimethyl sulphoxide
DPBS Dulbecco's phosphate-buffered salt solution
dt doublet of a triplet (in NMR)
o.th. of theory (for chemical yield)
EDC N'-(3-dimethylaminopropyl)-N-ethylcarbodiimide hydrochloride
EI electron impact ionization (in MS)
eq. equivalent(s)
ESI electron spray ionization (in MS)
FCS fetal calf serum
Fmoc (9H-fluoren-9-ylmethoxy)carbonyl
sat. saturated
GTP guanosine-5' triphosphate
h hour(s)
HATU O-(7-azabenzotriazol-1-yl)-N,N,N',N'-tetramethyluronium hexafluorophosphate
HEPES 4-(2-hydroxyethyl)piperazin-1 ethane sulphonic acid
HOAc acetic acid
HOBt 1-hydroxy-1H-benzotriazol hydrate
HOSu N-hydroxysuccinimide
HPLC high-pressure, high-performance liquid chromatography
conc. evaporated
LC-MS liquid chromatography coupled with mass spectrometry
m multiplet (in NMR)
min minute(s)
MS mass spectrometry
MTT 3-(4,5-Dimethylthiazol-2-yl)-2,5-diphenyl-2H-tetrazoliumbromide
NMM N-methylmorpholine
NMP N-methyl-2-pyrrolidinone
NMR nuclear magnetic resonance spectrometry
PBS phosphate-buffered salt solution
Pd/C palladium on activated carbon
quant. quantitative (with yield)
quart quartet (in NMR)
quint quintet (in NMR)
$R_f$ retention index (in DC)
RT room temperature
$R_t$ retention time (in HPLC)
s singlet (in NMR)
t triplet (in NMR
tert. tertiary
TFA trifluoroacetic acid
THF tetrahydrofuran
UV ultra-violet spectrometry
v/v volume to volume ratio (of a solution)
Z benzyloxycarbonyl
tog. together
HPLC and LC-MS Methods:
Method 1 (LC-MS):
  Instrument: Waters Acquity SQD UPLC System; column: Waters Acquity UPLC HSS T3 1.8µ 50 mm×1 mm; Eluent A: 1 l water+0.25 ml 99% formic acid, Eluent B: 1 l acetonitrile+0.25 ml 99% formic acid; Gradient: 0.0 min 90% A→1.2 min 5% A→2.0 min 5% A; flow rate: 0.40 ml/min; oven: 50° C.; UV detection: 210-400 nm.
Method 2 (LC-MS):
  Instrument: Micromass Quattro Premier with Waters UPLC Acquity; column: Thermo Hypersil GOLD 1.9µ 50 mm×1 mm; Eluent A: 1 l water+0.5 ml 50% formic acid, Eluent B: 1 l acetonitrile+0.5 ml 50% formic acid; gradient: 0.0 min 90% A→0.1 min 90% A→1.5 min 10% A→2.2 min 10% A; flow rate: 0.33 ml/min; oven: 50° C.; UV detection: 210 nm.
Method 3 (LC-MS):
  Instrument: Micromass Quattro Micro MS with HPLC Agilent Series 1100; column: Thermo Hypersil GOLD 3µ 20 mm×4 mm; Eluent A: 1 l water+0.5 ml 50% formic acid, Eluent B: 1 l acetonitrile+0.5 ml 50% formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.
Method 4 (LC-MS):
  MS instrument type: Micromass ZQ; instrument type HPLC: HP 1100 Series; UV DAD; column: Phenomenex Gemini 3µ 30 mm×3.00 mm; Eluent A: 1 l water+0.5 ml 50% formic acid, Eluent B: 1 l acetonitrile+0.5 ml 50% formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.
Method 5 (HPLC):
Instrument: HP 1090 Series II; column: Merck Chromolith SpeedROD RP-18c, 50 mm×4.6 mm; precolumn: Merck Chromolith Guard Cartridge Kit RP-18e, 5 mm×4.6 mm; injection volume: 5 µl; Eluent A: 70% HClO₄ in water (4 ml/liter), Eluent B: acetonitrile; gradient: 0.00 min 20% B→0.50 min 20% B→3.00 min 90% B→3.50 min 90% B→3.51 min 20% B→4.00 min 20% B; flow rate: 5 ml/min; column temperature: 40° C.
Method 6 (HPLC):
Instrument: Waters 2695 with DAD 996; column: Merck Chromolith SpeedROD RP-18e, 50 mm×4.6 mm; precolumn: Merck Chromolith Guard Cartridge Kit RP-18e, 5 mm×4.6 mm; Eluent A: 70% HClO₄ in water (4 ml/liter), Eluent B: acetonitrile; gradient: 0.00 min 5% B→0.50 min 5% B→3.00 min 95% B→4.00 min 95% B; flow rate: 5 ml/min.
Method 7 (LC-MS):
MS instrument type: Waters ZQ; instrument type HPLC: Agilent 1100 Series; UV DAD; column: Thermo Hypersil GOLD 3µ 20 mm×4 mm; Eluent A: 1 l water+0.5 ml 50% formic acid, Eluent B: 1 l acetonitrile+0.5 ml 50% formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.
Method 8 (LC-MS):
MS instrument type: Waters ZQ; instrument type HPLC: Agilent 1100 Series; UV DAD; column: Thermo Hypersil GOLD 3µ 20 mm×4 mm; Eluent A: 1 l water+0.5 ml 50% formic acid, Eluent B: 1 l acetonitrile+0.5 ml 50% formic acid; gradient: 0.0 min 100% A→2.0 min 60% A→2.3 min 40% A→3.0 min 20% A→4.0 min 10% A→4.2 min 100% A (flow rate 2.5 ml/min); oven: 55° C.; flow rate: 2 ml/min; UV detection: 210 nm.
Method 9 (LC-MS):
Instrument: Waters Acquity SQD UPLC System; column: Waters Acquity UPLC HSS T3 1.8µ 50 mm×1 mm; Eluent A: 1 l water+0.25 ml 99% formic acid, Eluent B: 1 l acetonitrile+0.25 ml 99% formic acid; Gradient: 0.0 min 95% A→6.0 min 5% A→7.5 min 5% A; oven: 50° C.; flow rate: 0.35 ml/min; UV detection: 210-400 nm.
Method 10 (HPLC):
Instrument: Agilent 1200 Series; column: Agilent Eclipse XDB-C18 5µ 4.6 mm×150 mm; precolumn: Phenomenex KrudKatcher Disposable Pre-Column; injection volume: 5 µl; Eluent A: 1 l water+0.01% trifluoroacetic acid; Eluent B: 1 l acetonitrile+0.01% trifluoroacetic acid; gradient: 0.00 min 10% B→1.00 min 10% B→1.50 min 90% B→5.5 min 10% B; flow rate: 2 ml/min; column temperature: 30° C.
Method 11 LC-MS:
Instrument: Waters Acquity SQD UPLC System; column: Waters Acquity UPLC HSS T3 1.8µ 30 mm×2 mm; Eluent A: 1 l water+0.25 ml 99% formic acid, Eluent B: 1 l acetonitrile+0.25 ml 99% formic acid; Gradient: 0.0 min 90% A→1.2 min 5% A→2.0 min 5% A; flow rate: 0.60 ml/min; oven: 50° C.; UV detection: 208-400 nm.

For all reactants or reagents whose synthesis has not been explicitly described, it can be assumed that they were obtained commercially from readily available sources. For all reactants or reagents whose synthesis has not been explicitly described but were not commercially or readily available, a reference is given to literature in which their preparation is described.

Starting Compounds and Intermediates:
Starting Compound 1

(2R,3R)-3-[(2S)-1-(tert.-butoxycarbonyl)pyrrolidine-2-yl]-3-methoxy-2-methyl propane acid (Boc-dolaproin) dicyclohexylamine salt

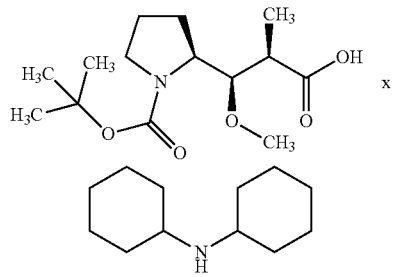

This compound can be produced in a variety of ways following references in literature, e.g. Pettit et al., Synthesis 1996, 719; Shioiri et al., Tetrahedron Lett. 1991, 32, 931; Shioiri et al., Tetrahedron 1993, 49, 1913; Koga et al., *Tetrahedron Lett.* 1991, 32, 2395; Vidal et al., *Tetrahedron* 2004, 60, 9715; Poncet et al., *Tetrahedron* 1994, 50, 5345. Here, it was synthesized using instructions by Shioiri et al. (*Tetrahedron Lett.* 1991, 32, 931)

Starting Compound 2 tert.-butyl-(3R,4S,5S)-3-methoxy-5-methyl-4-(methylamino)heptanoate-hydrochloride (dolaisoleucin-OtBu×HCl)

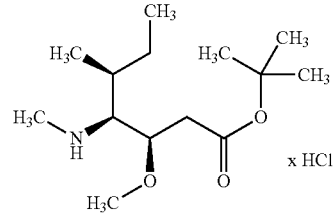 [SMILES: CC[C@H](C)[C@H](NC)[C@@H](CC(=O)OC(C)(C)C)OC]

This compound can be produced in a variety of ways following references in literature, e.g. Pettit et al., *J. Org. Chem.* 1994, 59, 1796; Koga et al., *Tetrahedron Lett.* 1991, 32, 2395; Shioiri et al., *Tetrahedron Lett.* 1991, 32, 931; Shioiri et al., *Tetrahedron* 1993, 49, 1913. Here, it was synthesized using instructions by Koga et al. (*Tetrahedron Lett.* 1991, 32, 2395).

Intermediate 1 tert.-butyl-(3R,4S,5S)-4-[{N-[(benzyloxy)carbonyl]-L-valyl}(methyl)amino]-3-methoxy-5-methylheptanoate

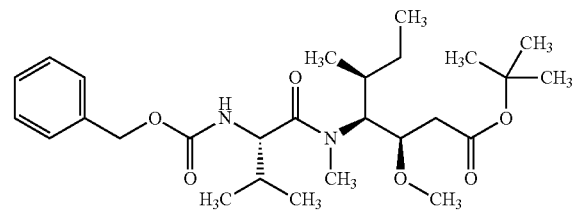 [SMILES: CC[C@H](C)[C@@H]([C@@H](CC(=O)OC(C)(C)C)OC)N(C)C(=O)[C@@H](NC(=O)OCc1ccccc1)C(C)C]

425 mg (1.7 mmol) N-[(benzyloxy)carbonyl]-L-valine were dissolved in 50 ml of DMF and mixed successively with 500 mg (1.7 mmol) of tert.-butyl-(3R,4S,5S)-3-methoxy-5-methyl-4-(methylamino)-heptanoate hydrochloride (starting compound 2), 356 mg (1.9 mmol) 1-(3-dimethylaminopropyl)-3-ethyl carbodiimide hydrochloride, 285 mg (1.9 mmol) 1-hydroxy-1H-benzotriazol hydrate and 655 mg (5.1 mmol) of N,N-iiisopropylethylamine. The mixture was stirred for 20 h at RT. Another 142 mg (0.5 mmol) of N-[(benzyloxy)carbonyl]-L-valine, 119 mg (0.6 mmol) of 1-(3-dimethylaminopropyl)-3-ethylcarbodiimide hydrochloride, 95 mg (0.6 mmol) of 1-hydroxy-1H-benzotriazol hydrate and 218 mg (1.7 mmol) N,N-diisopropylethylamine were added and the mixture was treated with ultrasound for 90 min. The mixture was then poured into a solution of semi-saturated aqueous ammonium chloride and ethyl acetate. The organic phase was separated off, washed successively with saturated sodium hydrogen carbonate solution and saturated sodium chloride solution, then dried over magnesium sulphate, filtered and evaporated. The remainder was purified using preparative HPLC. 329 mg (40% o. th.) of the title compound were obtained as a colorless oil.

HPLC (Method 5): $R_t$=2.5 min;

LC-MS (method 1): $R_t$=1.45 min; MS (ESIpos): m/z=493 $(M+H)^+$.

Intermediate 2 tert.-butyl-(3R,4S,5S)-3-methoxy-5-methyl-4-[methyl(L-valyl)amino]heptanoate

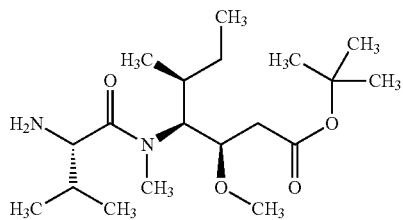 [SMILES: CC[C@H](C)[C@@H]([C@@H](CC(=O)OC(C)(C)C)OC)N(C)C(=O)[C@@H](N)C(C)C]

500 mg (1 mmol) tert.-butyl-(3R,4S,5S)-4-[{N-[(benzyloxy)carbonyl]-L-valyl}(methyl)amino]-3-methoxy-5-methylheptanoate (intermediate 1) were dissolved in 50 ml Methanol and, after adding 100 mg 10% Palladium on activated carbon, was hydrated at RT for 1 h under atmospheric pressure. The catalyst was then filtered off and the solving agents was removed in a vacuum. 370 mg (quant.) of the title compound were obtained an almost colorless oil.

HPLC (Method 5): $R_t$=1.59 min;

LC-MS (method 1): $R_t$=0.74 min; MS (ESIpos): m/z=359 $(M+H)^+$.

Intermediate 3

N-[(9H-fluoren-9-ylmethoxy)carbonyl]-N-methyl-L-valyl-N-[(3R,4S,5S)-1-tert.-butoxy-3-methoxy-5-methyl-1-oxoheptane-4-yl]-N-methyl-L-valinamide

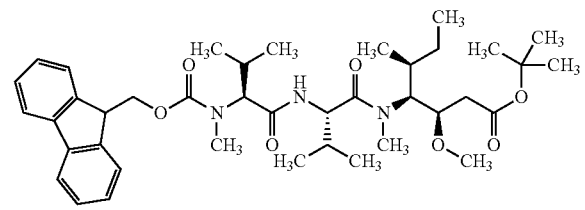 [SMILES: CC[C@H](C)[C@@H]([C@@H](CC(=O)OC(C)(C)C)OC)N(C)C(=O)[C@@H](NC(=O)[C@H](C(C)C)N(C)C(=O)OCC1c2ccccc2-c2ccccc21)C(C)C]

396 mg (1.1 mmol) N-[(9H-fluoren-9-ylmethoxy)carbonyl]-N-methyl-L-valine were dissolved in 20 ml DMF and 365 mg (1 mmol) tert.-butyl-(3R,4S,5S)-3-methoxy-5-methyl-4-[methyl(L-valyl)amino]heptanoate (intermediate 2), 234 mg (1.2 mmol) 1-(3-dimethylaminopropyl)-3-ethylcarbodiimide hydrochloride and 187 mg (1.2 mmol) 1-hydroxy-1H-benzotriazol hydrate were added in succession. The mixture was stirred overnight at RT. The mixture was then poured into a solution of semi-saturated aqueous ammonium chloride and ethyl acetate. The organic phase was separated off, washed successively with saturated sodium hydrogen carbonate solution and saturated sodium chloride solution, then dried over magnesium sulphate, filtered and evaporated. The residue was used directly in the next step, without purification.

Yield: 660 mg (68% o. th.)

HPLC (Method 5): $R_t$=3.0 min;

LC-MS (method 1): $R_t$=1.61 min; MS (ESIpos): m/z=694 $(M+H)^+$.

Intermediate 4

N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide

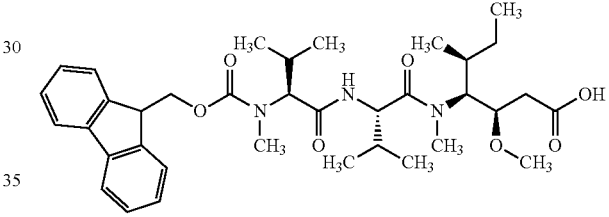

650 mg (0.94 mmol) N-[(9H-fluoren-9-ylmethoxy)carbonyl]-N-methyl-L-valyl-N-[(3R,4S,5S)-1-tert.-butoxy-3-methoxy-5-methyl-1-oxoheptane-4-yl]-N-methyl-L-valinamide (intermediate 3) were absorbed by 5 ml dichlormethane, 5 ml trifluoroacetic acid were added and then stirred overnight at RT. Then, the mixture was evaporated in vacuum and the remaining residue was purified using HPLC. 430 mg (72% o. th.) of the title compound were obtained as a colorless foam.

HPLC (Method 5): $R_t$=2.4 min.

LC-MS (method 2): $R_t$=1.51 min; MS (ESIpos): m/z=638 $(M+H)^+$.

Intermediate 5

N-(tert.-butoxycarbonyl)-N-methyl-L-valyl-N-[(2R,3S,4S)-1-carboxy-2-methoxy-4-methylhexane-3-yl]-N-methyl-L-valinamide

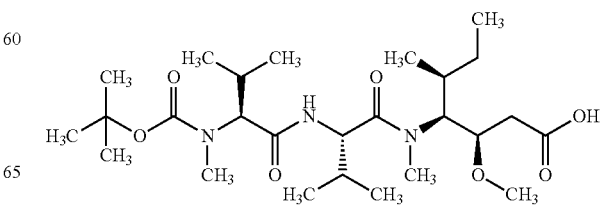

51 mg (0.08 mmol) N-[(9H-fluoren-9-ylmethoxy)carbonyl]-N-methyl-L-valyl-N-[(2R,3S,4S)-1-carboxy-2-methoxy-4-methylhexane-3-yl]-N-methyl-L-valinamide (intermediate 4) were dissolved in 10 ml DMF and 0.5 ml piperidine were added. After stirring for 10 min at RT, the mixture was evaporated in a vacuum and the residue was dissolved in diethyl ether. Insoluble components were filtered off and washed several times with diethyl ether. The filter residue was added to 5 ml dioxane/water (1:1) and, using 1N sodium hydroxide, the solution was adjusted to a pH-value of 11. Under ultrasound treatment, 349 mg (1.6 mmol) Di-tert.-butyldicarbonate were added in several stages. The pH-value of 11 of the solution was maintained. After completion of the reaction, the dioxane was evaporated and the aqueous solution was adjusted to a pH-value of 2-3, using citric acid. Twice an extraction with 50 ml ethyl acetate each followed. The organic phases were purified, dried over magnesium sulphate and evaporated in a vacuum. The residue was absorbed by diethyl ether and precipitated using pentane. The solving agents were separated using decantation. The residue was macerated several times with pentane and then dried in a high vacuum. Thus, 31 mg (93% o.th.) of the title compound were obtained.

HPLC (Method 6): Rt=2.2 min.
LC-MS (method 2): $R_t$=1.32 min; MS (ESIpos): m/z=516 (M+H)$^+$.

Intermediate 6

N-[(9H-fluoren-9-ylmethoxy)carbonyl]-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide

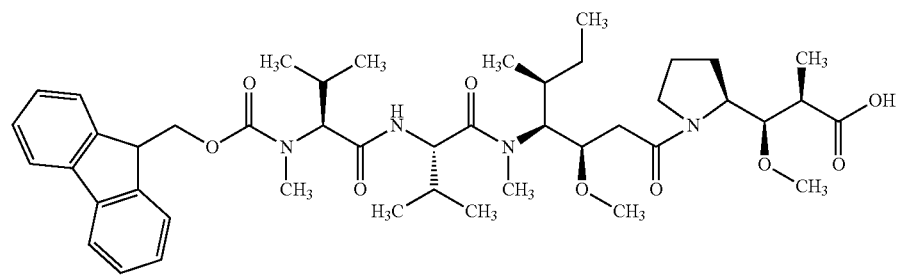 [SMILES: CC[C@H](C)[C@@H]([C@@H](CC(=O)N1CCC[C@H]1[C@H](OC)[C@@H](C)C(=O)O)OC)N(C)C(=O)[C@@H](NC(=O)[C@H](C(C)C)N(C)C(=O)OCC1c2ccccc2-c2ccccc21)C(C)C]

315 mg (0.494 mmol) N-[(9H-fluoren-9-ylmethoxy)carbonyl]-N-methyl-L-valyl-N-[(2R,3S,4S)-1-carboxy-2-methoxy-4-methylhexane-3-yl]-N-methyl-L-valinamide (intermediate 4) were dissolved in 12 ml DMF, and 104 mg (0.543 mmol) 1-(3-dimethylaminopropyl)-3-ethylcarbodiimide hydrochloride and 83 mg (0.543 mmol) 1-hydroxy-1H-benzotriazol hydrate were added and stirred for 90 min at RT. Then 112 µl N,N-diisopropylethylamine and 149 mg (0.494 mmol) (2R,3R)-3-methoxy-2-methyl-3-[(2S)-pyrrolidine-2-yl]propane acid sodium trifluoracetate, which had at first been synthesized from starting compound 1 by cleavage of the Boc protection group using trifluoroacetic acid, were added. The composition was stirred for 2 h at RT and then evaporated in a high vacuum. The remaining residue was then purified using preparative HPLC twice. 140 mg (35% o. th.) of the title compound were obtained as a colorless foam.

HPLC (Method 5): Rt=2.4 min.
LC-MS (method 1): $R_t$=1.38 min; MS (ESIpos): m/z=807 (M+H)$^+$.

Intermediate 7

Benzyl-(βS)-N-{(2R,3R)-3-methoxy-2-methyl-3-[(2S)-pyrrolidine-2-yl]propanoyl}-β-methyl-L-phenylalaninate sodium trifluoracetate

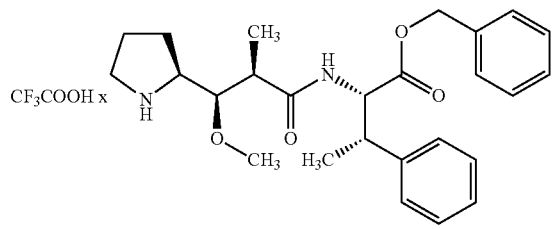 [SMILES: CO[C@@H]([C@@H]1CCCN1)[C@@H](C)C(=O)N[C@H](C(=O)OCc1ccccc1)[C@@H](C)c1ccccc1]

First, (2R,3R)-3-[(2S)-1-(tert.-butoxycarbonyl)pyrrolidine-2-yl]-3-methoxy-2-methylpropanoic acid was released by absorbing 351 mg (0.75 mmol) of dicyclohexylamine salt (starting compound 1) in ethyl acetate and separating out by means of aqueous potassium hydrogen sulphate solution. The organic phase was dried over magnesium sulphate, filtered and evaporated. The residue was then absorbed in 10 ml of DMF and 373 mg (0.75 mmol) of benzyl-(βS)-β-methyl-L-phenylalaninate sodium trifluoroacetate [synthesized using commercially available (βS)-N-(tert.-butoxycarbonyl)-β-methyl-L-phenylalanine through DEC/DMAP-supported esterification with benzyl alcohol and subsequent cleavage of the Boc protection group with the help of trifluoroacetic acid], 428 mg (1.125 mmol) of O-(7-azabenzotriazol-1-yl)-N,N,N',N'-tetramethyluronium-hexafluorophosphate (HATU) and 392 µl of N,N-diisopropylethylamine were added in succession. The mixture was stirred for 20 h at RT. The mixture was then poured into a solution of semi-saturated aqueous ammonium chloride and ethyl acetate. The organic phase was separated off, purified with sodium hydrogen carbonate solution and then sodium chloride solution and finally evaporated. The residue was purified using preparative HPLC. Thus, 230 mg (57% d. Th.) of the Boc-protected intermediate benzyl-(βS)-N-{(2R,3R)-3-[(2S)-1-(tert.-butoxycarbonyl)pyrrolidine-2-yl]-3-methoxy-2-methylpropanoyl}-(3-methyl-L-phenylalaninate were obtained.

HPLC (Method 6): $R_t$=2.3 min;
LC-MS (method 1): $R_t$=1.36 min; MS (ESIpos): m/z=539 (M+H)$^+$, 230 mg (0.42 mmol) of this intermediate were absorbed in 5 ml dichloromethane, then 5 ml trifluoroacetic acid were added and stirred for 30 min at RT. It was then evaporated in a vacuum. The remaining residue was further dried in a vacuum and then lyophilized from acetonitrile/water. Thus, 230 mg (quant.) of the title compound were obtained.

HPLC (Method 6): $R_t$=1.6 min;

Intermediate 8

Benzyl-N-{(2R,3R)-3-methoxy-2-methyl-3-[(2S)-pyrrolidine-2-yl]propanoyl}-L-phenylalaninate sodium trifluoroacetate

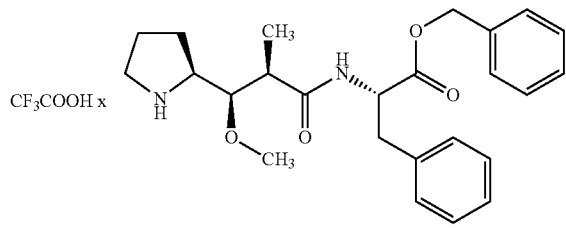 [SMILES: CO[C@@H]([C@@H]1CCCN1)[C@@H](C)C(=O)N[C@@H](Cc1ccccc1)C(=O)OCc1ccccc1]

Analogous to the synthesis of intermediate 7, the title compound has been synthesized from starting compound 1 and benzyl-L-phenylalaninate.

HPLC (Method 5): $R_t$=1.6 min;
LC-MS (method 1): $R_t$=0.85 min; MS (ESIpos): m/z=425 (M+H)$^+$.

Intermediate 9

N-benzyl-N-methyl-L-phenylalaninamide sodium trifluoroacetate

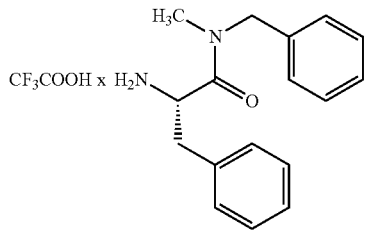 [SMILES: CN(Cc1ccccc1)C(=O)[C@@H](N)Cc1ccccc1]

1000 mg (3.77 mmol) of N-(tert.-butoxycarbonyl)-L-phenylalanine were dissolved in 10 ml DMF and 457 mg (3.77 mmol) N-methylbenzylamine, 2150 mg (5.65 mmol) O-(7-Azabenzotriazol-1-yl)-N,N,N',N'-tetramethyluronium hexafluorophosphate and 657 µl N,N-diisopropylethylamine were added. The batch was stirred for 30 minutes at RT and then evaporated in a vacuum. The residue was absorbed by dichloromethane and extracted three times with water. The organic phase was dried out over magnesium sulphate and evaporated. The residue was purified using flash chromatography on silica gel with petroleum ether/ethyl acetate 3:1 as solvents. The product fractions were evaporated and the residue was dried in a high vacuum. Thus, 1110 mg (75% o. th.) of the Boc-protected intermediate N-benzyl-N$^\alpha$-(tert.-butoxycarbonyl)-N-methyl-L-phenylalaninamide were obtained.

HPLC (Method 5): $R_t$=2.1 min;
LC-MS (method 1): $R_t$=1.14 min; MS (ESIpos): m/z=369 (M+H)$^+$.

1108 mg (3.007 mmol) of this intermediate were absorbed in 30 ml dichloromethane, then 10 ml trifluoroacetic acid were added and stirred for 30 min at RT. Subsequently, it was evaporated in a vacuum, the remaining residue was dissolved in dichloromethane and the solving agent was distilled. The residue was dissolved in pentane twice, the solving agents decanted away each time, and the product was finally dried in a high vacuum. Thus, 1075 mg (93% o. th.) of the title compound in resin form were obtained.

HPLC (Method 5): $R_t$=1.6 min;
LC-MS (method 1): $R_t$=0.6 min; MS (ESIpos): m/z=269 (M+H)$^+$.

Intermediate 10

N-benzyl-N$^\alpha$-{(2R,3R)-3-methoxy-2-methyl-3-[(2S)-pyrrolidine-2-yl]propanoyl}-N-methyl-L-phenylalaninamide trifluoroacetic acid

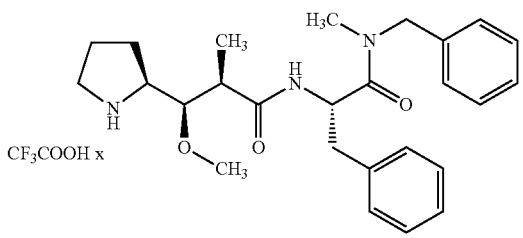 [SMILES: CO[C@@H]([C@@H]1CCCN1)[C@@H](C)C(=O)N[C@@H](Cc1ccccc1)C(=O)N(C)Cc1ccccc1]

Firstly, (2R,3R)-3-[(2S)-1-(tert.-butoxycarbonyl)pyrrolidine-2-yl]-3-methoxy-2-methylpropanoic acid was released by dissolving 141 mg (0.491 mmol) of the dicyclohexylamine salt (starting material 1) in ethyl acetate and then shaking out with 5% aqueous sulfuric acid. The organic phase was dried over magnesium sulphate, filtered and evaporated. The residue was absorbed by 10 ml DMF and 187.6 mg (0.49 mmol) N-benzyl-N-methyl-L-phenylalaninamide trifluoroacetic acid salt (intermediate 9), 190.3 mg (1.47 mmol) 0-(7-azabenzotriazol-1-yl)-N,N,N',N'-tetramethyluronium-hexafluorophosphate (HATU) and 256 µl N,N-diisopropylethylamine were added. The composition was stirred for 1 h at RT. The batch was then evaporated, the residue was absorbed in ethyl acetate, and the solution then went through manual solvent extraction successively using saturated ammonium chloride solution, sodium hydrogen carbonate solution and water. The organic phase was dried out over magnesium sulphate and evaporated. The residue was purified using flash chromatography on silica gel with acetonitrile/water 30:1 as eluent. The product fractions were evaporated and the residue was then dried in a high vacuum. Thus, 168 mg (64% o. th.) of the Boc-protected intermediate tert.-butyl-(2S)-2-[(1R,2R)-3-({(2S)-1-[benzyl(methyl)amino]-1-oxo-3-phenylpropane-2-yl}amino)-1-methoxy-2-methyl-3-oxopropyl]pyrrolidine-1-carboxylate were obtained.

HPLC (method 5): $R_t$=2.2 min;
LC-MS (method 2): $R_t$=1.22 min; MS (ESIpos): m/z=538 (M+H)$^+$.

168 mg (0.312 mmol) of this intermediate were absorbed in 15 ml dichloromethane, then 3 ml trifluoroacetic acid were added and stirred for 30 min at RT. It was then evaporated in a vacuum. The remaining residue was dissolved first in dichloromethane and then diethyl ether, and the solving agent was distilled away in each case. After drying in a high vacuum, 170 mg (99% o. th.) of the title compound were obtained as a resin.

HPLC (method 5): $R_t$=1.7 min;
LC-MS (method 1): $R_t$=0.73 min; MS (ESIpos): m/z=438 (M+H)$^+$.

Intermediate 11

Methyl-N-{(2R,3R)-3-methoxy-2-methyl-3-[(2S)-pyrrolidine-2-yl]propanoyl}-L-phenylalaninate trifluoroacetic acid salt

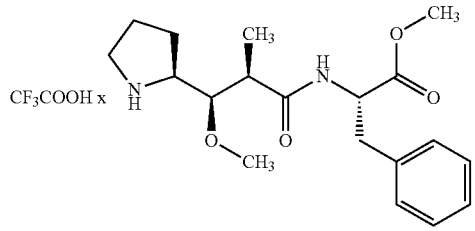 [SMILES: COC(=O)[C@H](Cc1ccccc1)NC(=O)[C@H](C)[C@@H](OC)[C@@H]1CCCN1]

Analogous to the synthesis for intermediate 10, the title compound was synthesized using (2R,3R)-3-[(2S)-1-(tert.-butoxycarbonyl)pyrrolidine-2-yl]-3-methoxy-2-methylpropanoic acid dicyclohexylamine salt (starting material 1) and methyl-L-phenylalaninate hydrochloride.

HPLC (method 6): $R_t$=0.6 min;
LC-MS (method 3): $R_t$=1.17 min; MS (ESIpos): m/z=349 (M+H)$^+$.

Intermediate 12

Benzyl-N-{(2R,3R)-3-methoxy-2-methyl-3-[(2S)-pyrrolidine-2-yl]propanoyl}-L-tryptophanate trifluoroacetic acid salt

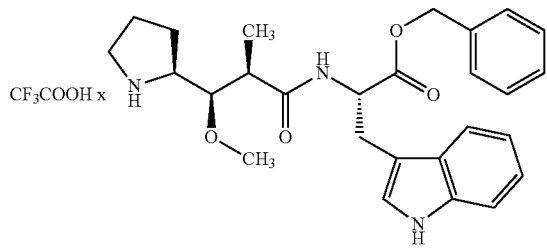 [SMILES: CO[C@@H]([C@@H]1CCCN1)[C@@H](C)C(=O)N[C@@H](Cc1c[nH]c2ccccc12)C(=O)OCc1ccccc1]

Analogous to the synthesis for intermediate 10, the title compound was synthesized using (2R,3R)-3-[(2S)-1-(tert.-butoxycarbonyl)pyrrolidine-2-yl]-3-methoxy-2-methylpropanoic acid dicyclohexylamine salt (starting material 1) and benzyl-L-tryptophanate.

HPLC (method 5): $R_t$=2.0 min;
LC-MS (method 1): $R_t$=0.8 min; MS (ESIpos): m/z=464 (M+H)$^+$.

Intermediate 13

Benzyl-(1S,2R)-1-({(2R,3R)-3-methoxy-2-methyl-3-[(2S)-pyrrolidin-2-yl]propanoyl}amino)-2-phenylcyclopropancarboxylate trifluoroacetic acid sodium chloride

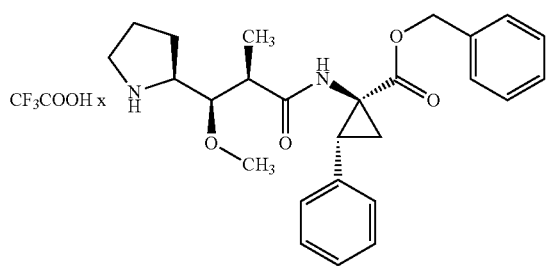 [SMILES: CO[C@@H]([C@@H]1CCCN1)[C@@H](C)C(=O)N[C@@]1(C(=O)OCc2ccccc2)C[C@@H]1c1ccccc1]

Analogous to the synthesis for intermediate 10, the title compound was synthesized using (2R,3R)-3-[(2S)-1-(tert.-butoxycarbonyl)pyrrolidine-2-yl]-3-methoxy-2-methylpropanoic acid dicyclohexylamine salt (starting material 1) and benzyl-(1S,2R)-1-amino-2-phenylcyclopropancarboxylate. The latter was synthesized by esterification using standard procedures of commercially available (1S,2R)-1-[(tert.-butoxycarbonyl)amino]-2-phenylcyclopropancarbonic acid with benzyl alcohol and subsequent Boc cleavage using trifluoroacetic acid.

HPLC (Method 6): $R_t$=1.5 min;
LC-MS (method 2): $R_t$=0.93 min; MS (ESIpos): m/z=437 (M+H)$^+$.

Intermediate 14

Benzyl-(2R,3R)-3-methoxy-2-methyl-3-[(2S)-pyrrolidin-2-yl]propanoate trifluoroacetic acid

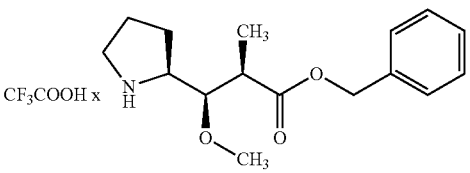 [SMILES: CO[C@@H]([C@@H]1CCCN1)[C@@H](C)C(=O)OCc1ccccc1]

First, (2R,3R)-3-[(2S)-1-(tert.-butoxycarbonyl)pyrrolidine-2-yl]-3-methoxy-2-methylpropanoic acid was released from 1.82 g (3.88 mmol) of the dicyclohexylamine salt (starting material 1) through absorption in 150 ml ethyl acetate and by extraction with 100 ml 0.5% aqueous sulfuric acid. The organic phase was dried over magnesium sulphate, filtered and evaporated. The residue was absorbed in 10 ml dioxane and 10 ml water, 1517 (4.66 mmol) cesium carbonate were added and the mixture was then treated in an ultrasonic bath for 5 min. It was then evaporated in a vacuum and the residue was co-distilled with DMF once. The residue was then absorbed by 15 ml DMF and added to 1990 mg (11.64 mmol) benzyl bromide. The mixture was treated in an ultrasonic bath for 15 min and then evaporated in a vacuum. The residue was split between ethyl acetate and water. The organic phase was separated off, purified using sodium chloride solution and then evaporated. The residue was then purified using preparative HPLC. Thus, 1170 mg (80% o. th.) of the Boc-protected intermediate tert.-butyl-(2S)-2-[(1R,2R)-3-(benzyloxy)-1-methoxy-2-methyl-3-oxopropyl]pyrrolidine-1-carboxylate were obtained.

The 1170 mg of the intermediate were added to 15 ml dichloromethane straight away which was then added to 5 ml trifluoroacetic acid. After 15 min of stirring at RT, the mixture was evaporated in a vacuum after which the residue was lyophilized using dioxane. After drying in a high vacuum, we obtained 1333 mg (84% o.th.) of the title compound as a yellow oil.

HPLC (method 5): $R_t$=1.5 min;
LC-MS (method 1): $R_t$=0.59 min; MS (ESIpos): m/z=278 (M+H)$^+$.

Intermediate 15

N-(tert.-butoxycarbonyl)-N-methyl-L-valyl-N-[(3R,4S,5S)-1-{(2S)-2-[(1R,2R)-2-carboxy-1-methoxypropyl]pyrrolidine-1-yl}-3-methoxy-5-methyl-1-oxoheptane-4-yl]-N-methyl-L-valinamide

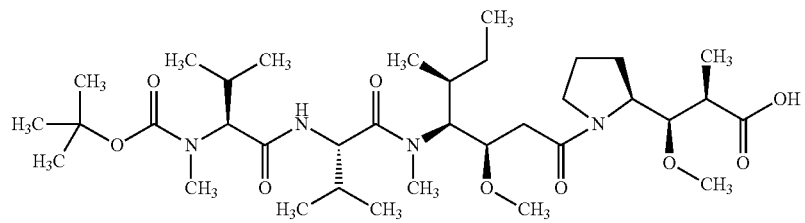 [SMILES: CC[C@H](C)[C@@H]([C@@H](CC(=O)N1CCC[C@H]1[C@H](OC)[C@@H](C)C(=O)O)OC)N(C)C(=O)[C@@H](NC(=O)[C@H](C(C)C)N(C)C(=O)OC(C)(C)C)C(C)C]

1200 mg (2.33 mmol) of N-(tert.-butoxycarbonyl)-N-methyl-L-valyl-N-[(2R,3S,4S)-1-carboxy-2-methoxy-4-methylhexane-3-yl]-N-methyl-L-valinamide (intermediate 5) were mixed with 910.8 mg (2.33 mmol) benzyl-(2R,3R)-3-methoxy-2-methyl-3-[(2S)-pyrrolidin-2-yl]propanoate sodium trifluoroacetate (intermediate 14), 1327 mg (3.49 mmol) of O-(7-Azabenzotriazol-1-yl)-N,N,N',N'-tetramethyluronium-hexafluorophosphate and 2027 μl N,N-diisopropylethylamine in 50 ml of DMF and stirred at RT for 5 minutes. Afterwards the solvent was evaporated under vacuum. The remaining residue was absorbed in ethyl acetate and successively extracted in 5% of lemon acid solution and saturated sodium hydrogen carbonate solution. The organic phase was separated and evaporated. The residue was purified by means of a preparative HPLC. The product fractions were combined, evaporated and the residue dried in a high vacuum. This way, 1000 mg (55% o. th.) of the benzyl ester-intermediate N-(tert.-butoxycarbonyl)-N-methyl-L-valyl-N-[(3R,4S,5S)-1-{(2S)-2-[(1R,2R)-3-(benzyloxy)-1-methoxy-2-methyl-3-oxopropyl]pyrrolidin-1-yl}-3-methoxy-5-methyl-1-oxoheptan-4-yl]-N-methyl-L-valinamide were yielded as a resin.

LC-MS (method 1): $R_t$=1.56 min; MS (ESIpos): m/z=775 (M+H)$^+$.

The total amount of this intermediate was absorbed in 25 ml of a composition of methanol and dichlormethane (20:1) and the benzyl ester-group was removed by way of hydration under normal pressure of 10% palladium on activated carbon as catalyst. After 30 minutes of stirring at RT the catalyst was filtered off and the filtrate was vacuum evaporated. The yield was 803 mg (91% o. th.) of the title compound as a white solid substance.

HPLC (Method 5): $R_t$=2.1 min;
LC-MS (method 1): $R_t$=1.24 min; MS (ESIpos): m/z=685 (M+H)$^+$.

Intermediate 16

(1S,2R)-1-Amino-2-phenyl-N-propylcyclopropancarboxamid sodium trifluoroacetate

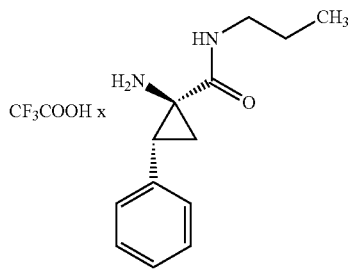 [SMILES: CCCNC(=O)[C@]1(N)C[C@@H]1c1ccccc1]

The title compound was produced by means of coupling of commercially available (1S,2R)-1-[(tert.-butoxycarbonyl)amino]-2-phenylcyclopropane carbon acid with n-propylamine in the presence of O(7-Azabenzotriazol-1-yl)-N,N,N',N'-tetramethyluronium-hexafluorophosphate (HATU), followed by cleavage of Boc with trifluoroacetic acid (yield of 85% o. th, over both stages).

HPLC (method 5): $R_t$=1.2 min;
LC-MS (method 1): $R_t$=0.52 min; MS (ESIpos): m/z=219 (M+H)$^+$.

Intermediate 17

Ethyl-(1S,2R)-1-amino-2-phenylcyclopropancarboxylate sodium trifluoroacetate

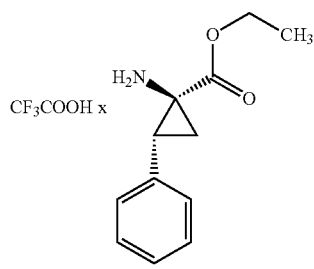

The title compound was synthesized by esterification using standard procedures of commercially available (1S,2R)-1-[(tert.-butoxycarbonyl)amino]-2-phenylcyclopropancarbonic acid with ethanol and subsequent Boc cleavage using trifluoroacetic acid.

LC-MS (method 1): $R_t$=0.50 min; MS (ESIpos): m/z=206 (M+H)$^+$.

Intermediate 18

1-Naphthylmethyl-N-(tert.-butoxycarbonyl)-L-phenylalaninate

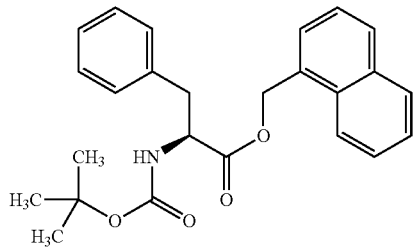 [SMILES: CC(C)(C)OC(=O)N[C@@H](Cc1ccccc1)C(=O)OCc1cccc2ccccc12]

1192 mg (6.2 mmol) of EDC, 578 μl (4.1 mmol) of triethylamine, 345 mg (2.8 mmol) of DMAP, and 328 mg (2.1 mmol) of 1-naphthylmethanol were added at RT to a solution of 500 mg (1.89 mmol) of N-Boc-L-phenylalanine in 25 ml dichlormethane. The reaction composition was stirred overnight, then diluted with 50 ml Dichlormethane and successively washed in a solution of 10% of aqueous citric acid, water, and saturated saline. The organic phase was dried over magnesium sulphate and then evaporated, and the residue purified with preparative HPLC. The yield was 501 mg (66% o. th.) of the title compound.

LC-MS (method 1): $R_t$=1.33 min; m/z=406 (M+H)$^+$.

Intermediate 19

1-Naphthylmethyl-L-phenylalaninate-Hydrochlorid

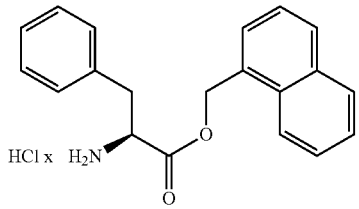 [SMILES: "HCl x" ; N[C@@H](Cc1ccccc1)C(=O)OCc1cccc2ccccc12]

500 mg (1.2 mmol) of 1-naphthylmethyl-N-(tert.-butoxycarbonyl)-L-phenylalaninate (intermediate 18) were stirred into 20 ml of a 4 N hydrogen chloride solution diluted in dioxane and stirred for 1 hour at RT. Then the reaction composition was evaporated and the residue vacuum dried. The yield was 421.5 mg (quant.) of the title compound.

LC-MS (method 1): $R_t$=0.80 min; m/z=306 (M+H)$^+$.

Intermediate 20

N-(tert.-butoxycarbonyl)-N-methyl-L-valyl-N-[(3R,4S,5S)-3-methoxy-1-{(2S)-2-[(1R,2R)-1-methoxy-2-methyl-3-{[(2S)-1-(1-naphthylmethoxy)-1-oxo-3-phenylpropane-2-yl]amino}-3-oxopropyl]pyrrolidin-1-yl}-5-methyl-1-oxoheptan-4-yl]-N-methyl-L-valinamide

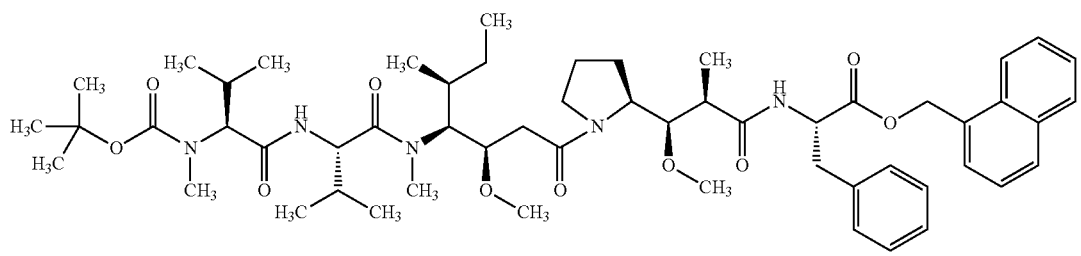 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCc1cccc2ccccc12)OC)N(C)C(=O)[C@@H](NC(=O)[C@H](C(C)C)N(C)C(=O)OC(C)(C)C)C(C)C]

15.3 µl (88 µmol) N,N-diisopropylethylamine, 6.7 mg (44 µmol) HOBt and 6.7 mg (35 µmol) EDC were added to a solution of 20 mg (29 µmol) N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) in 1 ml DMF and the composition was then stirred for 30 minutes. Then, 11 mg (32 µmol) of 1-Naphthylmethyl-L-phenylalaninate-hydrochloride (intermediate 19) were added. After having stirred the reaction composition overnight, the components thereof where directly separated by means of preparative HPLC. The yield was 26.1 mg (92% o. th.) of the title compound.

LC-MS (method 1): $R_t$=1.61 min; m/z=973 (M+H)$^+$.

Intermediate 21

N-(tert.-butoxycarbonyl)-N-methyl-L-valyl-N-[(3R,4S,5S)-3-methoxy-1-{(2S)-2-[(1R,2R)-1-methoxy-2-methyl-3-{[(2S)-1-(1-naphthylmethoxy)-1-oxo-3-phenylpropane-2-yl]amino}-3-oxopropyl]pyrrolidin-1-yl}-5-methyl-1-oxoheptan-4-yl]-N-methyl-L-valinamide

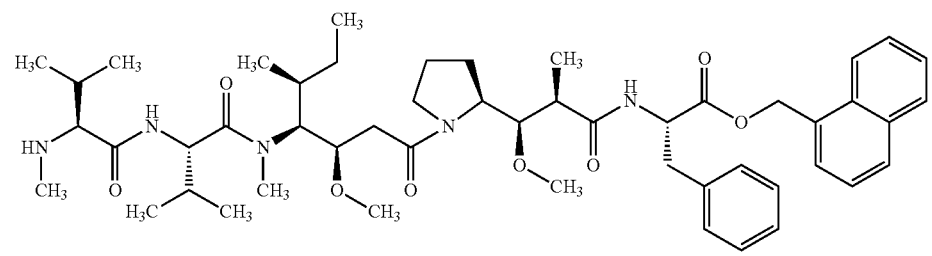

x CF$_3$COOH 26 mg (27 µmol) N-(tert.-Butoxycarbonyl)-N-methyl-L-valyl-N-[(3R,4S,5S)-3-methoxy-1-{(2S)-2-[(1R,2R)-1-methoxy-2-methyl-3-{[(2S)-1-(1-naphthylmethoxy)-1-oxo-3-phenylpropan-2-yl]amino}-3-oxopropyl]pyrrolidin-1-yl}-5-methyl-1-oxoheptan-4-yl]-N-methyl-L-valinamide (intermediate 20) were dissolved in 1 ml dichlormethane and mixed with 0.2 ml TFA. The reaction composition was stirred for 30 minutes at RT and then evaporated. The yield was 26.3 mg (99.7% o. th.) of the title compound.

LC-MS (method 1): $R_t$=1.02 min; m/z=873 (M+H)$^+$.

Intermediate 22

Adamantane-1-yl-N-(tert.-butoxycarbonyl)-L-phenylalaninate

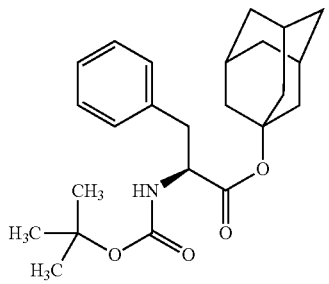 [SMILES: CC(C)(C)OC(=O)N[C@@H](Cc1ccccc1)C(=O)OC12CC3CC(CC(C3)C1)C2]

1192 mg (6.2 mmol) of EDC, 578 µl (4.1 mmol) of triethylamine, 345 mg (2.8 mmol) of DMAP, and 316 mg (2.1 mmol) of 1-adamantanol were added at RT to a solution of 500 mg (1.89 mmol) of N-Boc-L-phenylalanine in 25 ml dichlormethane. The reaction composition was stirred overnight, then diluted with 50 ml Dichlormethane and successively washed in a solution of 10% of aqueous citric acid, water, and saturated saline. The organic phase was dried over magnesium sulphate and then evaporated, and the residue purified with preparative HPLC. The yield was 336 mg (43% o. th.) of the title compound.

LC-MS (method 1): $R_t$=1.49 min; m/z=400 (M+H)$^+$.

Intermediate 23

Adamantane-1-yl-L-phenylalaninate-hydrochlorid

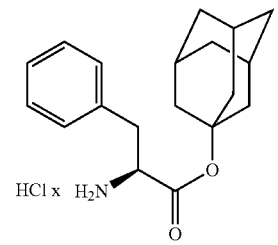 [SMILES: "HCl x" ; N[C@@H](Cc1ccccc1)C(=O)OC12CC3CC(CC(C3)C1)C2]

336 mg (840 µmol) of adamantane-1-yl-N-(tert.-butoxycarbonyl)-L-phenylalaninate (intermediate 22) were dissolved in 12 ml of a 4 N hydrogen chloride solution diluted in dioxane and stirred for 1 hour at RT. Then, the reaction composition was evaporated and the residue purified over preparative HPLC (gradient elution methanol/water+0.01% TFA). The yield was 228 mg (81% o. th.) of the title compound.

LC-MS (method 2): $R_t$=1.03 min; m/z=300 (M+H)$^+$.

Intermediate 24

N-(tert.-butoxycarbonyl)-N-methyl-L-valyl-N-[(3R,4S,5S)-1-{(2S)-2-[(1R,2R)-3-{[(2S)-1-(adamantane-1-yloxy)-1-oxo-3-phenylpropane-2-yl]amino}-1-methoxy-2-methyl-3-oxopropyl]pyrrolidine-1-yl}-3-methoxy-5-methyl-1-oxoheptan-4-yl]-N-methyl-L-valinamide

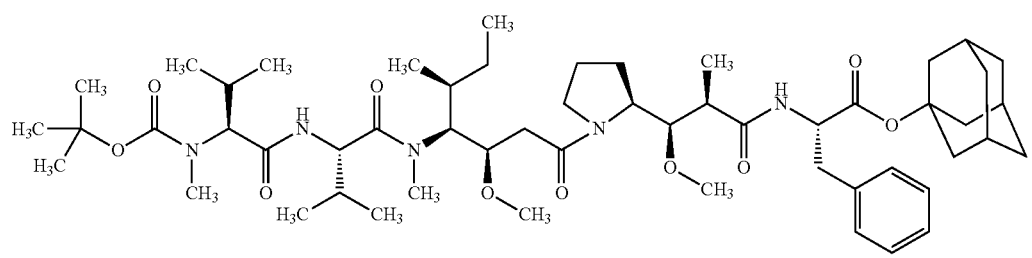 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC12CC3CC(CC(C3)C1)C2)OC)N(C)C(=O)[C@@H](NC(=O)[C@H](C(C)C)N(C)C(=O)OC(C)(C)C)C(C)C]

15.3 µl (88 µmol) of N,N-diisopropylethylamine, 6.7 mg (44 µmol) of HOBt, and 6.7 mg (35 µmol) of EDC were added to a solution of 20 mg (29 µmol) N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) in 1 ml DMF and the composition was then stirred for 30 minutes. Then, 9.6 mg (32 µmol) of 1-naphthylmethyl-L-phenylalaninate-hydrochloride (intermediate 23) were added. After having stirred the reaction composition overnight, the components thereof where directly separated by means of preparative HPLC. The yield was 15 mg (90% purity, 48% o. th.) of the title compound.

LC-MS (method 1): $R_t$=1.67 min; m/z=967 (M+H)$^+$.

Intermediate 25

N-methyl-L-valyl-N-[(3R,4S,5S)-1-{(2S)-2-[(1R,2R)-3-{[(2S)-1-(adamantane-1-yloxy)-1-oxo-3-phenylpropane-2-yl]amino}-1-methoxy-2-methyl-3-oxopropyl]pyrrolidine-1-yl}-3-methoxy-5-methyl-1-oxoheptan-4-yl]-N-methyl-L-valinamide sodium trifluoroacetate

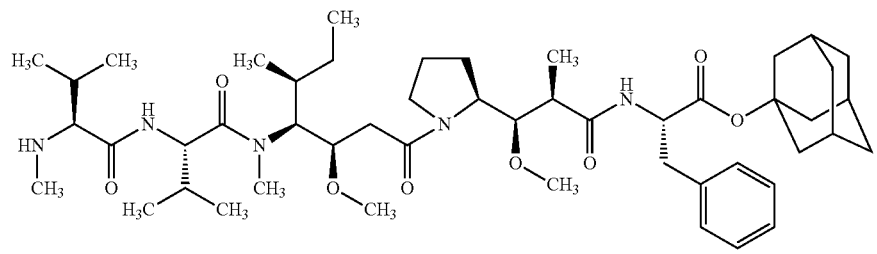

x CF₃COOH 15 mg (16 µmol) N-(tert.-butoxycarbonyl)-N-methyl-L-valyl-N-[(3R,4S,5S)-1-{(2S)-2-[(1R,2R)-3-{[(2S)-1-(adamantan-1-yloxy)-1-oxo-3-phenylpropan-2-yl]amino}-1-methoxy-2-methyl-3-oxo-propyl]pyrrolidin-1-yl}-3-methoxy-5-methyl-1-oxoheptan-4-yl]-N-methyl-L-valinamide (intermediate 24) were dissolved in 1 ml dichlormethane and mixed with 0.2 ml TFA. The reaction composition was stirred for 30 minutes at RT and then evaporated. The raw product was purified over preparative HPLC. The yield was 4.8 mg (32% o. th.) of the title compound.

LC-MS (method 1): $R_t$=1.10 min; m/z=867 (M+H)⁺.

Intermediate 26

Adamantane-1-ylmethyl-N-(tert.-butoxycarbonyl)-L-phenylalaninate

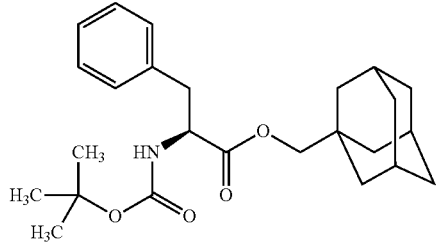 [SMILES: CC(C)(C)OC(=O)N[C@@H](Cc1ccccc1)C(=O)OCC12CC3CC(CC(C3)C1)C2]

1192 mg (6.2 mmol) of EDC, 578 µl (4.1 mmol) of triethylamine, 345 mg (2.8 mmol) of DMAP, and 345 mg (2.1 mmol) of 1-adamantylmethanol were added at RT to a solution of 500 mg (1.89 mmol) of N-Boc-L-phenylalanine in 25 ml dichlormethane. The reaction composition was stirred overnight, then diluted with 50 ml dichlormethane and successively washed in a solution of 10% of aqueous citric acid, water, and saturated saline. The organic phase was dried over magnesium sulphate and then evaporated, and the residue purified with preparative HPLC. The yield was 769 mg (90% o. th.) of the title compound.

LC-MS (method 2): $R_t$=1.84 min; m/z=414 (M+H)⁺.

Intermediate 27

Adamantan-1-ylmethyl-L-phenylalaninate-Hydrochloride

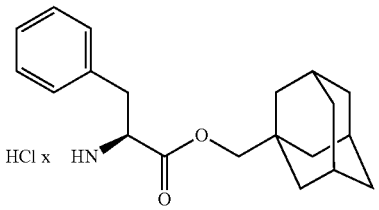 [SMILES: N[C@@H](Cc1ccccc1)C(=O)OCC12CC3CC(CC(C3)C1)C2]

769 mg (1.86 mmol) of adamantane-1-ylmethyl-N-(tert.-butoxycarbonyl)-L-phenylalaninate (intermediate 26) were dissolved in 25 ml of a 4 N hydrogen chloride solution diluted in dioxane and stirred for 1 hour at RT. Then the reaction composition was evaporated and the residue vacuum dried. The yield was 619 mg (95% o. th.) of the title compound.

LC-MS (method 1): $R_t$=0.82 min; m/z=314 (M+H)⁺.

Intermediate 28

N-(tert.-butoxycarbonyl)-N-methyl-L-valyl-N-[(3R,4S,5S)-1-{(2S)-2-[(1R,2R)-3-{[(2S)-1-(adamantane-1-ylmethoxy)-1-oxo-3-phenylpropane-2-yl]amino}-1-methoxy-2-methyl-3-oxopropyl]pyrrolidine-1-yl}-3-methoxy-5-methyl-1-oxoheptan-4-yl]-N-methyl-L-valinamide

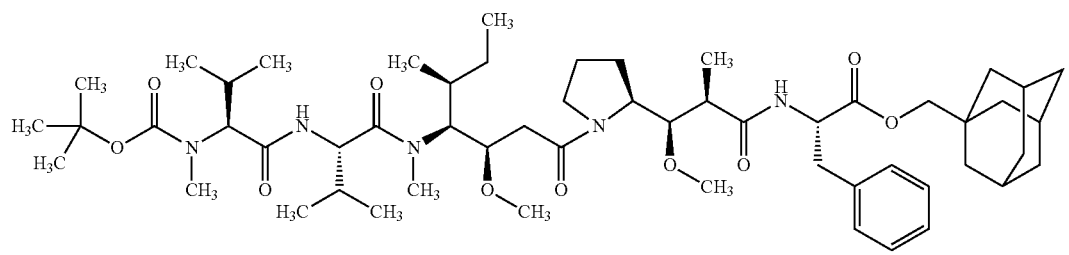 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCC12CC3CC(CC(C3)C1)C2)OC)N(C)C(=O)[C@@H](NC(=O)[C@H](C(C)C)N(C)C(=O)OC(C)(C)C)C(C)C]

15.3 μl (88 μmol) N,N-diisopropylethylamine, 6.7 mg (44 μmol) HOBt and 6.7 mg (35 μmol) EDC were added to a solution of 20 mg (29 μmol) N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) in 1 ml DMF and the composition was then stirred for 30 minutes. Then, 10.1 mg (32 μmol) of 1-naphthylmethyl-L-phenylalaninate-hydrochloride (intermediate 27) were added. After having stirred the reaction composition overnight, the components thereof where directly separated by means of preparative HPLC. The yield was 27.5 mg (93% o. th.) of the title compound.

LC-MS (method 1): $R_t$=1.70 min; m/z=980 (M+H)$^+$.

Intermediate 29

N-methyl-L-valyl-N-[(3R,4S,5S)-1-{(2S)-2-[(1R,2R)-3-{[(2S)-1-(adamantane-1-ylmethoxy)-1-oxo-3-phenylpropane-2-yl]amino}-1-methoxy-2-methyl-3-oxopropyl]pyrrolidine-1-yl}-3-methoxy-5-methyl-1-oxoheptan-4-yl]-N-methyl-L-valinamide sodium trifluoroacetate

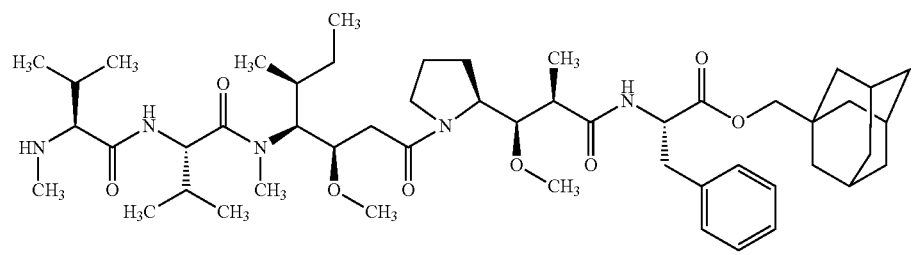

x CF$_3$COOH 27.5 mg (28 μmol) N-(tert.-butoxycarbonyl)-N-methyl-L-valyl-N-[(3R,4S,5S)-1-{(2S)-2-[(1R,2R)-3-{[(2S)-1-(adamantane-1-ylmethoxy)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide (intermediate 28) were dissolved in 1.8 ml dichloromethane and mixed with 361 μl ml TFA. The reaction composition was stirred for 30 minutes at RT and then evaporated. The residue was absorbed in water and lyophilized. The yield was 22.7 mg (81% o. th.) of the title compound.

LC-MS (method 1): $R_t$=1.14 min; m/z=880 (M+H)$^+$.

Intermediate 30 tert.-Butyl-[(2S)-1-(benzyloxy)-3-phenylpropan-2-yl]carbamate

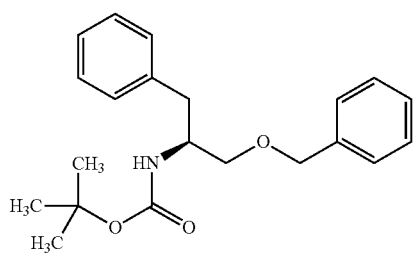 [SMILES: CC(C)(C)OC(=O)N[C@H](COCc1ccccc1)Cc1ccccc1]

500 mg (1.99 mmol) of N-Boc-L-phenylaninol were dissolved in 5 ml DMF and cooled down to 0° C. under argon atmosphere. Then 159 mg (3.98 mmol) of a 60% suspension of sodium hydride was added in liquid paraffin. The reaction composition then was stirred until completion of gas formation and then mixed with 260 μl (2.19 mmol) of benzyl bromide. The cooling bath was removed and the reaction composition stirred for 2 hours at RT. Afterwards, the batch was evaporated, the residue absorbed in ice water and the composition extracted with dichlormethane. The organic phase was washed with saturated saline, dried over magnesium sulphate and evaporated. The residue was purified by means of a preparative HPLC. The yield was 226 mg (33% o. th.) of the title compound.

LC-MS (method 1): $R_t$=1.28 min; m/z=342 (M+H)$^+$.

Intermediate 31

(2S)-1-(benzyloxy)-3-phenylpropane-2-amine-hydrochlorid

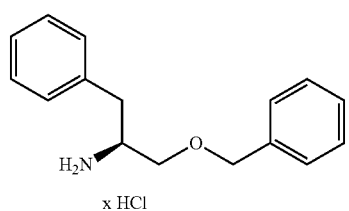 [SMILES: N[C@H](COCc1ccccc1)Cc1ccccc1]

x HCl 220 mg (644 μmol) of -tert.-butyl-[(2S)-1-(benzyloxy)-3-phenylpropane-2-yl]carbamate (intermediate 30) were dissolved in 11 ml of a 4 N hydrogen chloride solution diluted in dioxane and stirred for 1 hour at RT. Then, the batch was evaporated and the residue vacuum dried. The yield was 138 mg (77% o. th.) of the title compound.

LC-MS (method 1): $R_t$=0.65 min; m/z=242 (M+H)$^+$.

Intermediate 32

N-(tert.-butoxycarbonyl)-N-methyl-L-valyl-N-[(3R, 4S,5S)-1-{(2S)-2-[(1R,2R)-3-{[(2S)-1-(benzyloxy)-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide

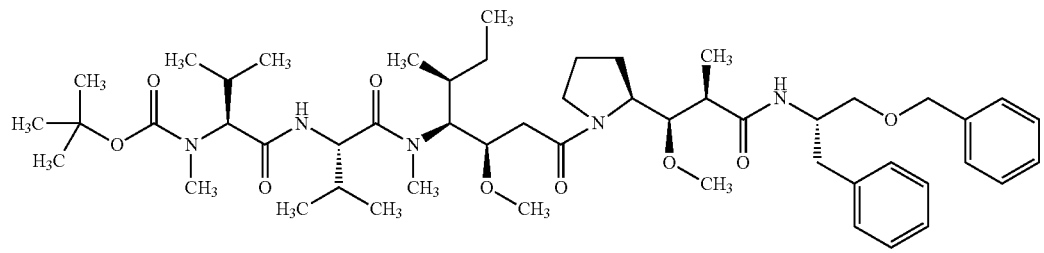 [SMILES: CC[C@H](C)[C@@H]([C@@H](CC(=O)N1CCC[C@H]1[C@H](OC)[C@@H](C)C(=O)N[C@H](COCc1ccccc1)Cc1ccccc1)OC)N(C)C(=O)[C@@H](NC(=O)[C@H](C(C)C)N(C)C(=O)OC(C)(C)C)C(C)C]

15.3 µl (88 µmol) of N,N-diisopropylethylamine, 6.7 mg (44 µmol) of HOBt, and 6.7 mg (35 µmol) of EDC were added to a solution of 20 mg (29 µmol) of N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) in 1 ml DMF and the composition was then stirred for 30 minutes. Then, 7.8 mg (32 µmol) of (2S)-1-(benzyloxy)-3-phenylpropane-2-amine-hydrochloride (intermediate 31) were added. After having stirred the reaction composition overnight, the components thereof where directly separated by means of preparative HPLC. The yield was 26 mg (98% o. th.) of the title compound.

LC-MS (method 1): $R_t$=1.51 min; m/z=909 (M+H)$^+$.

Intermediate 33

N-methyl-L-valyl-N-[(3R,4S,5S)-1-{(2S)-2-[(1R,2R)-3-{[(2S)-1-(benzyloxy)-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide sodium trifluoroacetate

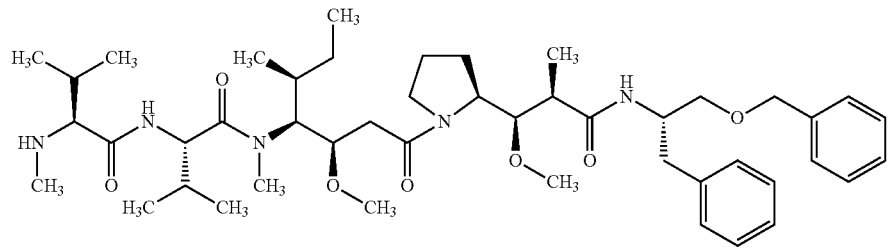

x CF$_3$COOH 26 mg (29 µmol) N-(tert.-butoxycarbonyl)-N-methyl-L-valyl-N-[(3R,4S,5S)-1-{(2S)-2-[(1R,2R)-3-{[(2S)-1-(benzyloxy)-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide (intermediate 32) were dissolved in 1.8 ml dichlormethane and mixed with 370 µl of TFA. The reaction composition was stirred for 30 minutes at RT and then evaporated. The residue was absorbed in water and lyophilized. The yield was 26.4 mg (quant.) of the title compound.

LC-MS (method 1): $R_t$=0.97 min; m/z=809 (M+H)$^+$.

Intermediate 34 tert.-butyl-[(2S)-1-(2-benzoylhydrazino)-1-oxo-3-phenylpropan-2-yl]carbamate

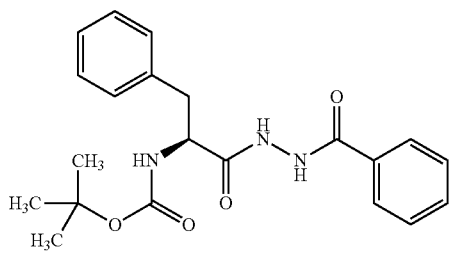 [SMILES: CC(C)(C)OC(=O)N[C@@H](Cc1ccccc1)C(=O)NNC(=O)c1ccccc1]

200 mg (754 µmol) of N-Boc-L-phenylalanine were dissolved in 8 ml of DMF mixed with 131 µl (754 µmol) of N,N-diisopropylethylamine, 346 mg (2261 µmol) of HOBt, 434 mg (2261 µmol) of EDC, and 411 mg (3015 µmol) of benzoyl hydrazine. The reaction composition was stirred at RT overnight, then evaporated, and the residue purified over preparative HPLC. The yield was 313 mg (95% purity, 100% o. th.) of the title compound.

LC-MS (method 1): $R_t$=0.94 min; m/z=384 (M+H)$^+$.

Intermediate 35

N'-[(2S)-2-amino-3-phenylpropanoyl]benzoylhydrazino-hydrochloride

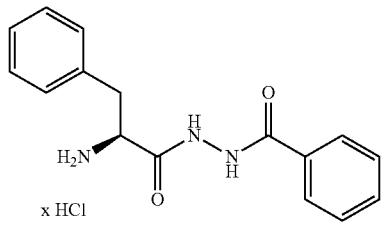 [SMILES: N[C@@H](Cc1ccccc1)C(=O)NNC(=O)c1ccccc1]

x HCl 313 mg (818 µmol) of tert.-butyl-[(2S)-1-(2-benzoylhydrazino)-1-oxo-3-phenylpropan-2-yl]carbamate (intermediate 34) were stirred in 13 ml of a 4 N hydrogen chloride solution diluted in dioxane and stirred for 1 hour at RT. Then the reaction composition was evaporated and the residue vacuum dried. The yield was 255 mg (92% o. th.) of the title compound.

LC-MS (method 1): $R_t$=0.44 min; m/z=284 (M+H)$^+$.

Intermediate 36 tert.-butyl-[(2S)-1-{[(2S)-1-{[(3R,4S,5S)-1-{(2S)-2-[(1R,2R)-3-{[(2S)-1-(2-benzoylhydrazino)-1-oxo-3-phenylpropane-2-yl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]amino}-3-methyl-1-oxobutan-2-yl]methylcarbamate

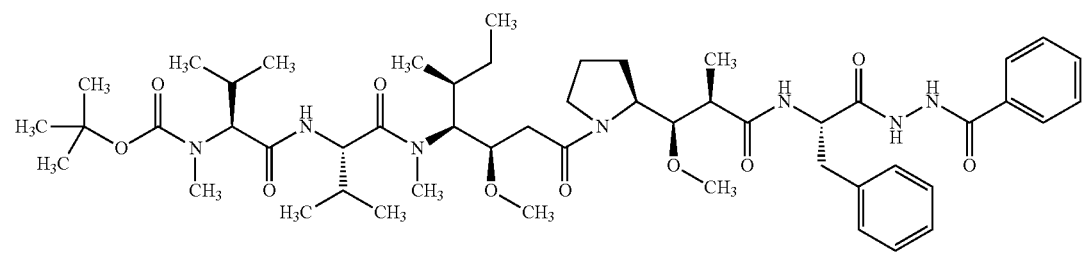

15.3 µl (88 µmol) of N,N-diisopropylethylamine, 6.7 mg (44 µmol) of HOBt, and 6.7 mg (35 µmol) of EDC were added to a solution of 20 mg (29 µmol) of N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) in 1 ml DMF and the composition was then stirred for 30 minutes. Then, 9.1 mg (32 µmol) of N'-[(2S)-2-amino-3-phenylpropanoyl]benzoylhydrazino-hydrochloride (intermediate 35) were added. After having stirred the reaction composition overnight, the components thereof where directly separated by means of preparative HPLC. The yield was 6.7 mg (24% o. th.) of the title compound.

LC-MS (method 1): $R_t$=1.32 min; m/z=951 (M+H)$^+$.

Intermediate 37

(2S)-N-[(3R,4S,5S)-1-{(2S)-2-[(1R,2R)-3-{[(2S)-1-(2-benzoylhydrazino)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N,3-dimethyl-2-{[(2S)-3-methyl-2-(methylamino)butanoyl]amino}butanamide sodium trifluoroacetate

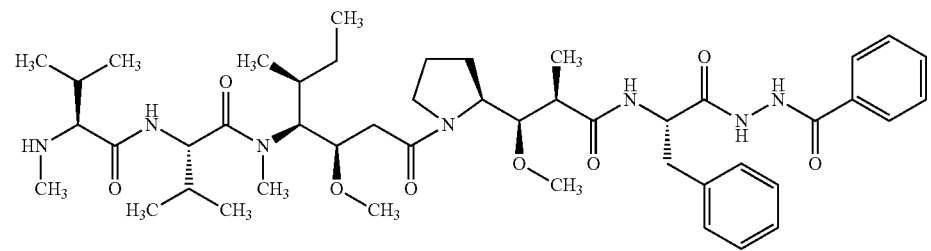

x CF$_3$COOH 6.7 mg (7 µmol) of tert.-butyl-[(2S)-1-{[(2S)-1-{[(3R,4S,5S)-1-{(2S)-2-[(1R,2R)-3-{[(2S)-1-(2-benzoylhydrazino)-1-oxo-3-phenylpropan-2-yl]amino}-1-methoxy-2-methyl-3-oxopropyl]pyrrolidin-1-yl}-3-methoxy-5-methyl-1-oxoheptan-4-yl](methyl)amino}-3-methyl-1-oxobutan-2-yl]amino}-3-methyl-1-oxobutan-2-yl]methylcarbamate (intermediate 36) were dissolved in 454 µl of dichlormethane and mixed with 91 µl of TFA. The reaction composition was stirred for 30 minutes at RT and then evaporated. The residue was absorbed in water and lyophilized. The yield was 6.8 mg (quant.) of the title compound.

LC-MS (method 1): $R_t$=0.80 min; m/z=851 (M+H)$^+$.

Intermediate 38

Benzyl-(1S,2R)-1-amino-2-phenylcyclopropancarboxylate sodium trifluoroacetate

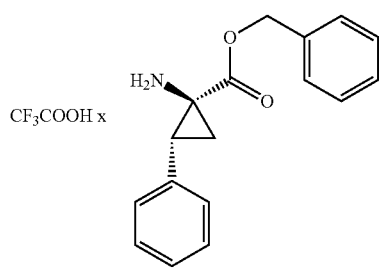 [SMILES: N[C@@]1(C(=O)OCc2ccccc2)C[C@@H]1c1ccccc1]

The latter was synthesized by esterification using standard procedures of commercially available (1S,2R)-1-[(tert.-butoxycarbonyl)amino]-2-phenylcyclopropancarbonic acid with benzyl alcohol and subsequent Boc cleavage using trifluoroacetic acid.

LC-MS (method 1): $R_t$=0.72 min; MS (ESIpos): m/z=268 (M+H)$^+$.

Intermediate 39

N-(tert.-butoxycarbonyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide

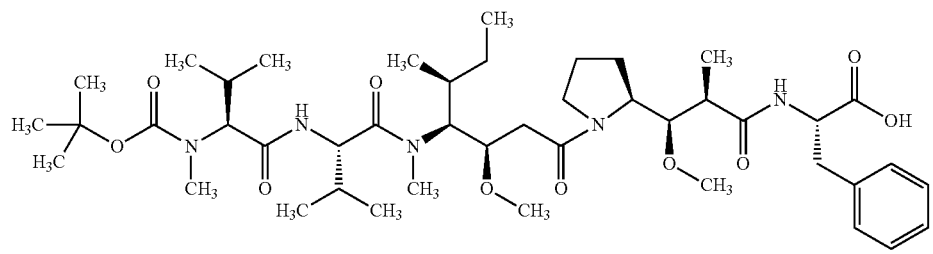 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)OC(C)(C)C)C(C)C]

383 mg (0.743 mmol) of N-(tert.-butoxycarbonyl)-N-methyl-L-valyl-N-[(2R,3S,4S)-1-carboxy-2-methoxy-4-methylhexan-3-yl]-N-methyl-L-valinamide (intermediate 5) were mixed with 485 mg (0.743 mmol) of benzyl-(2R,3R)-3-methoxy-2-methyl-3-[(2S)-pyrrolidin-2-yl]propanoyl}-L-phenylalaninate sodium trifluoroacetate (intermediate 8), 424 mg (1.114 mmol) of O-(7-Azabenzotriazol-1-yl)-N,N,N',N'-tetramethyluronium-hexafluorophosphate, and 388 µl N,N-diisopropylethylamine in 15 ml of DMF and stirred at RT for 10 minutes. Afterwards the solvent was evaporated under vacuum. The remaining residue was absorbed in ethyl acetate and successively extracted in 5% of lemon acid solution and saturated sodium hydrogen carbonate solution. The organic phase was isolated and the residue purified by means of preparative HPLC: The product fractions were combined, evaporated and the residue dried in a high vacuum. The yield was 335 mg (48% o. th.) of the benzyl ester intermediate in the form of a foam.

LC-MS (method 1): $R_t$=1.49 min; MS (ESIpos): m/z=922 (M+H)$^+$.

100 mg (0.11 mmol) of this intermediate were absorbed in 15 ml methanol and the benzyl ester-group was removed by way of hydration under normal pressure with a 10% Pd/C as catalyst. After 1 hour of stirring at RT the catalyst was filtered off and the filtrate was vacuum evaporated. Following lyophilization from dioxane, the yield was 85 mg (94% o. th.) of the title compound in the form of a white solid substance.

HPLC (method 5): $R_t$=2.4 min;
LC-MS (method 1): $R_t$=1.24 min; MS (ESIpos): m/z=832 (M+H)$^+$.

Intermediate 40

N-benzyl-L-tryptophanamide sodium trifluoroacetate

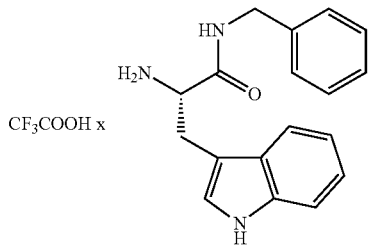 [SMILES: "CF3COOH x" ; N[C@@H](Cc1c[nH]c2ccccc12)C(=O)NCc1ccccc1]

202 mg (0.5 mmol) of 2,5-dioxopyrrolidin-1-yl-N-(tert.-butoxycarbonyl)-L-tryptophanate and 45 mg (0.42 mmol) of benzylamine were dissolved in 10 ml of DMF and mixed with 110 µl (630 µmol) of N,N-diisopropylethylamine. The batch was stirred for 3 hours at RT. Then, it was evaporated under vacuum and the residue was purified by means of flash chromatography with silica gel as the adsorbent (eluent: dichlormethane/methanol/17% of aq. ammonia 20:0.5:0.05). The appropriate fractions were mixed and evaporated. The residue resulting thereof was macerated with diethyl ether and then dried in high vacuum. The residue resulting thereof was then absorbed in 10 ml of dichlormethane and mixed with 3 ml of anhydrous trifluoroacetic acid. After 45 minutes of stirring at RT it was evaporated and the residue purified by means of preparative HPLC. After drying in high vacuum the 117 mg (57% o. th. over both stages) the title compound was yielded.
HPLC (method 5): $R_t$=1.6 min;
LC-MS (method 1): $R_t$=0.66 min; MS (ESIpos): m/z=294 (M+H)$^+$.

Intermediate 41

(1S,2R)-1-amino-2-phenylcyclopropancarboxamide sodium trifluoroacetate

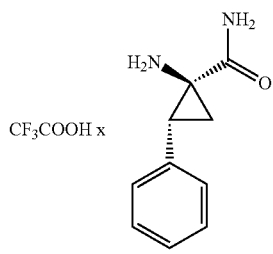 [SMILES: NC(=O)[C@]1(N)C[C@@H]1c1ccccc1]

50 mg (180 μmol) of commercially available (1S,2R)-1-[(tert.-butoxycarbonyl)amino]-2-phenylcyclopropane carbon acid were dissolved in 5 ml of DMF, mixed with 94 μl (541 μmol) of N,N-diisopropylethylamine, 31 mg (270 μmol) of N-hydroxysuccinimide, and 41.5 mg (216 μmol) of EDC and then stirred overnight at RT The reaction composition was then evaporated, the residue absorbed in dioxane, mixed with 71 mg (901 μmol) of ammonium hydrogen carbonate, and the batch left standing for 3 days at RT. The reaction composition was then diluted in a 1:1 mixture of ethyl acetate and water. The organic phase was then separated with saturated saline, dried over magnesium sulphate and evaporated. The residue resulting thereof was then absorbed in 3 ml of dichlormethane and mixed with 3 ml of anhydrous trifluoroacetic acid. After 1 hour of stirring it was evaporated. The residue was mixed with pentane, aspirated and lyophilized from dioxane. In this fashion 32 mg (62% o. th. over both stages) of the title compound was yielded.
HPLC (method 5): $R_t$=0.38 min;
LC-MS (method 1): $R_t$=0.20 min; MS (ESIpos): m/z=177 (M+H)$^+$.

Intermediate 42

N$^\alpha$-{(2R,3R)-3-Methoxy-2-methyl-3-[(2S)-pyrrolidin-2-yl]propanoyl}-L-tryptophanamide sodium trifluoroacetate

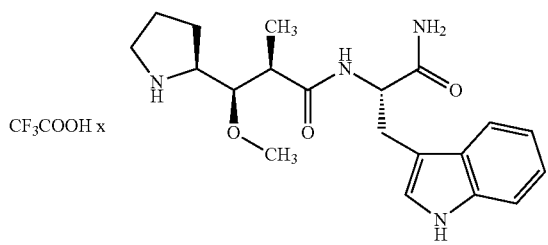 [SMILES: CO[C@@H]([C@@H]1CCCN1)[C@@H](C)C(=O)N[C@@H](Cc1c[nH]c2ccccc12)C(N)=O]

Analogous to the synthesis of intermediate 7, the title compound has been synthesized from starting compound 1 and L-tryptophanamide-hydrochloride.
HPLC (method 5): $R_t$=1.4 min;
LC-MS (method 1): $R_t$=0.92 min; MS (ESIpos): m/z=473 (M+H)$^+$.

Intermediate 43 tert.-butyl-4-(brommethyl)benzoate

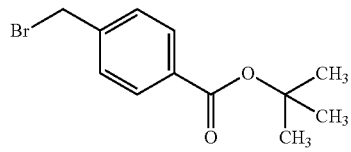

1000 mg (4.65 mmol) of 4-(brommethyl)benzoic acid were added to 6 ml of dichlormethane, then first 18 μl (0.23 mmol) of DMF were added and afterwards 811 μl (9.3 mmol) of oxalic acid chloride added drop wise. The batch was stirred for 15 min until gas formation was completed and the evaporated. The residue was absorbed in 10 ml of toluene and evaporated another time. Then, the benzoic acid chloride, thus obtained, was suspended in 30 ml of diethyl ether and mixed in portions with a suspension of 522 mg (4.65 mmol) of potassium.-tert.-butylate in 40 ml of diethyl ether. The reaction composition was stirred for 1 hour at RT and then evaporated. The filtrate was washed in water, saturated ammonium chloride, and saturated sodium chloride solution three times each, dried over magnesium sulphate and after filtration evaporated under vacuum. The raw product received was purified by means of flash chromatography over silica gel (eluent cyclohexane/ethyl acetate 10:1) The yield was 770 mg (51% o. th.) of the title compound.
MS (DCI): m/z=217 (M-54)+.

Intermediate 44

4-({[(2S)-2-amino-3-phenylpropyl]oxy}methyl)benzoic acid sodium trifluoroacetate

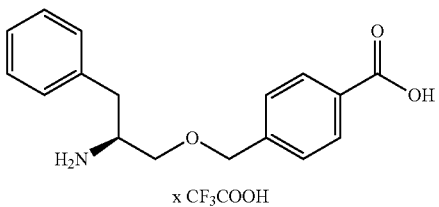 [SMILES: N[C@H](COCc1ccc(C(=O)O)cc1)Cc1ccccc1]

168.5 mg (0.67 mmol) of tert.-butyl-[(2S)-1-hydroxy-3-phenylpropane-2-yl]carbamate were added to 4.9 ml of DMF under argon and mixed with 53.6 mg (1.3 mmol) of sodium hydride (as 60% dispersion in liquid paraffin) at a temperature of 0° C. After 30 minutes 200 mg (0.74 mmol) of tert.-butyl-4-(brommethyl)benzoate was added at a temperature of 0° C. Following completion of measuring, the batch was stirred for 2 hours at RT. Afterwards, the batch was evaporated in the rotation steam boiler, the residue absorbed in ice water and the compound extracted with 50 ml of dichlormethane each. The organic phases were washed in saturated sodium hydride solution, dried over magnesium sulphate and evaporated in a vacuum. The raw product thus obtained is being purified by means of preparative HPLC. 50.2 mg (17% o. th.) of the intermediate of tert.-butyl-4-[({(2S)-2-[(tert.-butoxycarbonyl)amino]-3-phenylpropyl}oxy)methyl]benzoate were obtained.

HPLC (Method 10): $R_t$=4.06 min;
LC-MS (method 1): $R_t$=1.45 min; MS (ESIpos): m/z=442 (M+H)⁺.

50 mg (0.11 mmol) of this intermediate were dissolved at RT in 1.3 ml of trifluoroacetic acid and 6.4 ml of dichloromethane and stirred for 15 min. Then the batch was evaporated in the rotating steam boiler and the residue vacuum dried. The yield was 51.2 mg (99% o. th.) of the title compound.

HPLC (Method 10): $R_t$=2.40 min;
LC-MS (method 1): $R_t$=0.53 min; MS (ESIpos): m/z=286 (M+H)⁺.

Intermediate 45

Methyl-4-({[(2S)-2-amino-3-phenylpropyl]oxy}methyl)benzoate hydrochloride

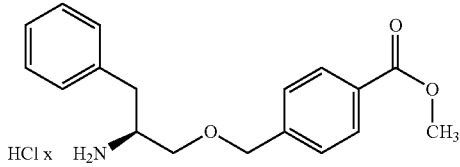 [SMILES: COC(=O)c1ccc(COC[C@@H](N)Cc2ccccc2)cc1]

51.2 mg (128 μmol) of 4-({[(2S)-2-amino-3-phenylpropyl]oxy}methyl)benzoic acid sodium trifluoracetate were added to 5 ml of methanol and mixed with 2.4 mg (13 μmol) of 4-toluenesulfonate acid monohydrate. The batch was stirred overnight under reflux. Then, 18.7 μl (256 μmol) of thionyl chloride were added and the composition heated again under reflux for 6 hours. Then the reaction composition was evaporated in the rotating steam boiler and the residue vacuum dried. Thus, 42.3 mg (80% purity, 88% o. th.) of the title compound were obtained which were used in the consecutive reaction without further purification.

HPLC (method 10): $R_t$=2.48 min;
LC-MS (method 1): $R_t$=0.68 min; MS (ESIpos): m/z=300 (M+H)⁺.

Intermediate 46

N-methyl-L-valyl-N-[(3R,4S,5S)-3-methoxy-1-{(2S)-2-[(1R,2R)-1-methoxy-3-{[(2S)-1-{[4-(methoxycarbonyl)benzyl]oxy}-3-phenylpropane-2-yl]amino}-2-methyl-3-oxopropyl]pyrrolidin-1-yl}-5-methyl-1-oxoheptan-4-yl]-N-methyl-L-valinamide sodium trifluoroacetate

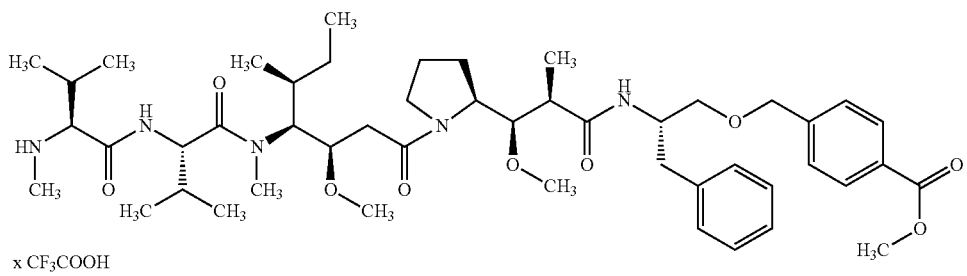 [SMILES: CC[C@H](C)[C@@H]([C@@H](CC(=O)N1CCC[C@H]1[C@H](OC)[C@@H](C)C(=O)N[C@H](COCc1ccc(C(=O)OC)cc1)Cc1ccccc1)OC)N(C)C(=O)[C@@H](NC(=O)[C@@H](NC)C(C)C)C(C)C]

20 mg (29 μmol) of N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) were added to 0.59 ml of DMF and mixed with 13.3 mg (35 μmol) of HATU and 20 μl (117 μmol) of N,N-diisopropylethylamine. After 30 minutes 9.6 mg (32 μmol) of methyl-4-({[(2S)-2-amino-3-phenylpropyl]oxy}methyl)benzoate hydrochloride (intermediate 45) were added. The reaction composition was stirred overnight and then, without further processing, directly separated into its components by means of preparative HPLC. A yield of 15.2 mg (54% o. th.) of the Boc protected intermediate of N-(tert.-butoxycarbonyl)-N-methyl-L-valyl-N-[(3R,4S,5S)-3-methoxy-1-{(2S)-2-[(1R,2R)-1-methoxy-3-{[(2S)-1-{[4-(methoxycarbonyl)benzyl]oxy}-3-phenylpropane-2-yl]amino}-2-methyl-3-oxopropyl]pyrrolidin-1-yl}-5-methyl-1-oxoheptan-4-yl]-N-methyl-L-valinamide was obtained.

LC-MS (method 1): $R_t$=1.49 min; MS (ESIpos): m/z=967 (M+H)⁺.

15.8 mg (99% o. th.) of the title compound were obtained, following cleavage of the Boc protection group with trifluoroacetic acid.

LC-MS (method 11): $R_t$=0.90 min; MS (ESIpos): m/z=867 (M+H)⁺.

Embodiments:

Example 1

N-(3-carboxypropyl)-N-methyl-L-valyl-N-[(3R,4S,5S)-3-methoxy-1-{(2S)-2-[(1R,2R)-1-methoxy-2-methyl-3-{[(2S)-1-(1-naphthylmethoxy)-1-oxo-3-phenylpropane-2-yl]amino}-3-oxopropyl]pyrrolidin-1-yl}-5-methyl-1-oxoheptan-4-yl]-N-methyl-L-valinamide

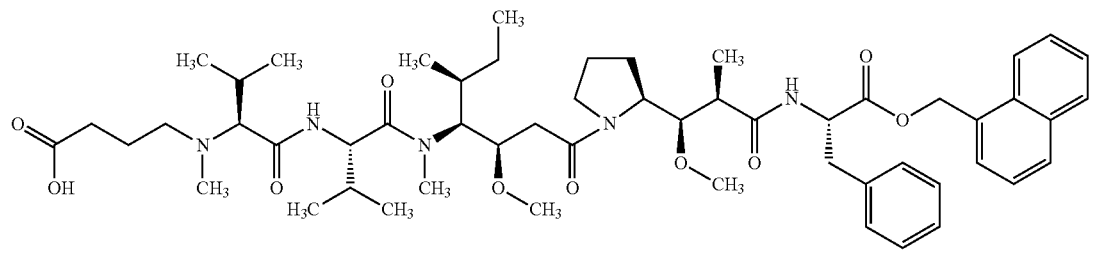 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCc1cccc2ccccc12)OC)N(C)C(=O)[C@@H](NC(=O)[C@H](C(C)C)N(C)CCCC(=O)O)C(C)C]

24 mg (24 μmol) of N-methyl-L-valyl-N-[(3R,4S,5S)-3-methoxy-1-{(2S)-2-[(1R,2R)-1-methoxy-2-methyl-3-{[(2S)-1-(1-naphthylmethoxy)-1-oxo-3-phenylpropane-2-yl]amino}-3-oxopropyl]pyrrolidin-1-yl}-5-methyl-1-oxoheptan-4-yl]-N-methyl-L-valinamide sodium trifluoroacetate (intermediate 21) and 31.5 μl of 15% aqueous amber aldehyde acid solution (49 μmol) were dissolved in 900 μl of a 1:1-dioxane/water composition and heated for 1 hour at a temperature of 100° C. After a short cooling period 1.7 mg (27 μmol) of sodium cyanoborohydride were added. The reaction composition was formulated with 0.1 of N hydrochloric acid to pH 3 and heated for 2 hours at a temperature of 100° C. It was reheated again for 2 hours at 100° C. after the same amounts of amber aldehyde acid solution, sodium cyanoborohydride, and hydrochloric acid had been added once again. Afterwards, the reaction composition had been separated directly by means of preparative HPLC. The yield was 20.1 mg (86% o. th.) of the title compound.

LC-MS (method 1): $R_t$=1.06 min; m/z=959 (M+H)$^+$.

$^1$H-NMR (500 MHz, DMSO-d$_6$): δ [ppm]=0.73-0.81 (m, 3H), 0.82-1.05 (m, 15H), 1.19-1.48 (m, 3H), 1.53-2.10 (m, 4H), 2.12-2.41 (m, 5H), 2.79 (d, 2H), 2.85-3.06 (m, 3H), 3.06-3.13 (m, 3H), 3.13-3.28 (m, 6H), 3.35-3.43 (m, 1H), 3.89-4.14 (m, 1H), 4.45-4.81 (m, 3H), 5.48-5.73 (m, 2H), 7.13-7.33 (m, 5H), 7.45-7.53 (m, 1H), 7.53-7.64 (m, 3H), 7.91-8.05 (m, 3H), 8.21-8.60 (m, 1H), 8.69-9.01 (m, 1H), 9.27-9.60 (m, 1H) [further signals hidden under peaks of solvent].

Example 2

N-(3-carboxypropyl)-N-methyl-L-valyl-N-[(3R,4S,5S)-1-{(2S)-2-[(1R,2R)-3-{[(2S)-1-(adamantane-1-yloxyy)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide

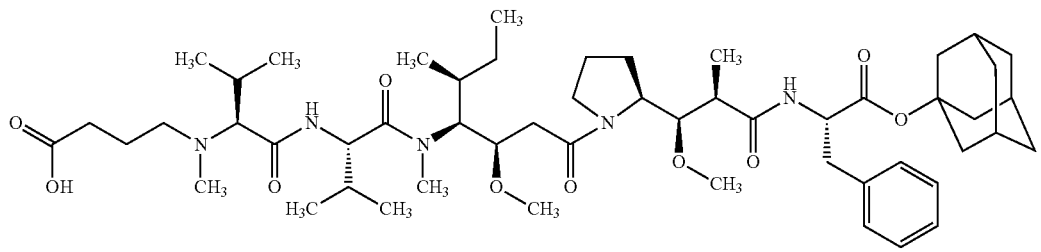 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC12CC3CC(CC(C3)C1)C2)OC)N(C)C(=O)[C@@H](NC(=O)[C@H](C(C)C)N(C)CCCC(=O)O)C(C)C]

4.8 mg (5 μmol) of N-methyl-L-valyl-N-[(3R,4S,5S)-1-{(2S)-2-[(1R,2R)-3-{[(2S)-1-(adamantane-1-yloxy)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide sodium trifluoroacetate (intermediate 25) and 6.3 μl of 15% aqueous amber aldehyde acid solution (10 μmol) were dissolved in 180 μl of a 1:1-dioxane/water composition and heated for 1 hour at a temperature of 100° C. After a short cooling period 0.34 mg (5 μmol) of sodium cyanoborohydride were added. The reaction composition was formulated with 0.1 of N hydrochloric acid to pH 3 and heated for 2 hours at a temperature of 100° C. It was reheated again for 2 hours at 100° C. after the same amounts of amber aldehyde acid solution, sodium cyanoborohydride, and hydrochloric acid had been added once again.

Afterwards, the reaction composition had been separated directly by means of preparative HPLC. The yield was 3.2 mg (69% o. th.) of the title compound.

LC-MS (method 1): $R_t$=1.14 min; m/z=952 (M+H)$^+$.

Example 3

N-(3-carboxypropyl)-N-methyl-L-valyl-N-[(3R,4S,5S)-1-{(2S)-2-[(1R,2R)-3-{[(2S)-1-(adamantane-1-ylmethoxy)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide

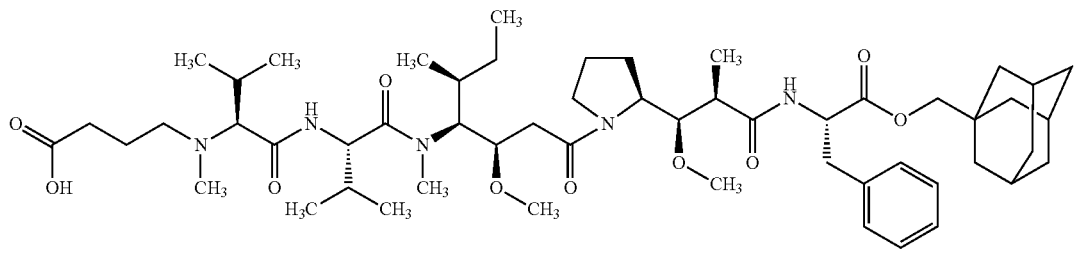 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCC12CC3CC(CC(C3)C1)C2)OC)N(C)C(=O)[C@@H](NC(=O)[C@H](C(C)C)N(C)CCCC(=O)O)C(C)C]

26 mg (26 µmol) of N-methyl-L-valyl-N-[(3R,4S,5S)-1-{(2S)-2-[(1R,2R)-3-{[(2S)-1-(adamantane-1-ylmethoxy)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide sodium trifluoroacetate (intermediate 29) and 33.9 µl of 15% aqueous amber aldehyde acid solution (53 µmol) were dissolved in 957 µl of a 1:1-dioxane/water composition and heated for 1 hour at a temperature of 100° C. After a short cooling period 1.81 mg (29 µmol) of sodium cyanoborohydride were added. The reaction composition was formulated with 0.1 of N hydrochloric acid to pH 3 and heated for 2 hours at a temperature of 100° C. It was reheated again for 2 hours at 100° C. after the same amounts of amber aldehyde acid solution, sodium cyanoborohydride, and hydrochloric acid had been added once again. Afterwards, the reaction composition had been separated directly by means of preparative HPLC. The yield was 18.5 mg (73% o. th.) of the title compound.

LC-MS (method 1): $R_t$=1.17 min; m/z=967 (M+H)$^+$.

Example 4

N-(3-carboxypropyl)-N-methyl-L-valyl-N-[(3R,4S,5S)-1-{(2S)-2-[(1R,2R)-3-{[(2S)-1-(benzyloxy)-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide

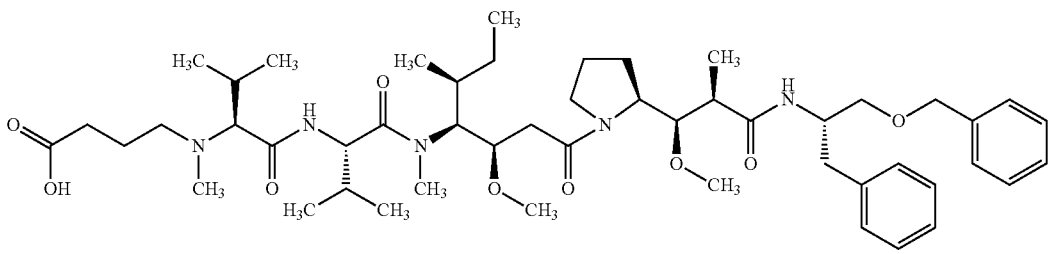 [SMILES: CC[C@H](C)[C@@H]([C@@H](CC(=O)N1CCC[C@H]1[C@H](OC)[C@@H](C)C(=O)N[C@H](COCc1ccccc1)Cc1ccccc1)OC)N(C)C(=O)[C@@H](NC(=O)[C@H](C(C)C)N(C)CCCC(=O)O)C(C)C]

24 mg (26 µmol) of N-methyl-L-valyl-N-[(3R,4S,5S)-1-{(2S)-2-[(1R,2R)-3-{[(2S)-1-(benzyloxy)-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide sodium trifluoroacetate (intermediate 33) and 33.7 µl of 15% aqueous amber aldehyde acid solution (52 µmol) were dissolved in 953 µl of a 1:1-dioxane/water composition and heated for 1 hour at a temperature of 100° C. After a short cooling period 1.80 mg (29 µmol) of sodium cyanoborohydride were added. The reaction composition was formulated with 0.1 of N hydrochloric acid to pH 3 and heated for 2 hours at a temperature of 100° C. It was reheated again for 2 hours at 100° C. after the same amounts of amber aldehyde acid solution, sodium cyanoborohydride, and hydrochloric acid had been added once again. Afterwards, the reaction composition had been separated directly by means of preparative HPLC. The yield was 15.2 mg (65% o. th.) of the title compound.

LC-MS (method 1): $R_t$=1.01 min; m/z=895 (M+H)$^+$.

$^1$H-NMR (500 MHz, DMSO-d$_6$): δ [ppm]=0.72-0.81 (m, 3H), 0.81-1.00 (m, 15H), 1.03 (dd, 3H), 1.12-1.56 (m, 3H), 1.62-2.45 (m, 10H), 2.61-2.73 (m, 1H), 2.78 (br. s, 2H), 2.84-3.07 (m, 3H), 3.11 (br. s, 2H), 3.17 (s, 1H), 3.21 (d, 3H), 3.26 (s, 3H), 3.30-3.35 (m, 2H), 3.51-3.94 (m, 4H), 4.00 (br. s, 1H), 4.08-4.35 (m, 1H), 4.50 (s, 1H), 4.53 (s, 1H), 4.55-4.78 (m, 2H), 7.12-7.16 (m, 1H), 7.16-7.25 (m, 4H), 7.30 (d, 1H), 7.33-7.42 (m, 4H), 7.76 and 8.01 (2d, 1H), 8.73-8.98 (m, 1H) [further signals hidden under peaks of solvent].

Example 5

N-(3-carboxypropyl)-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

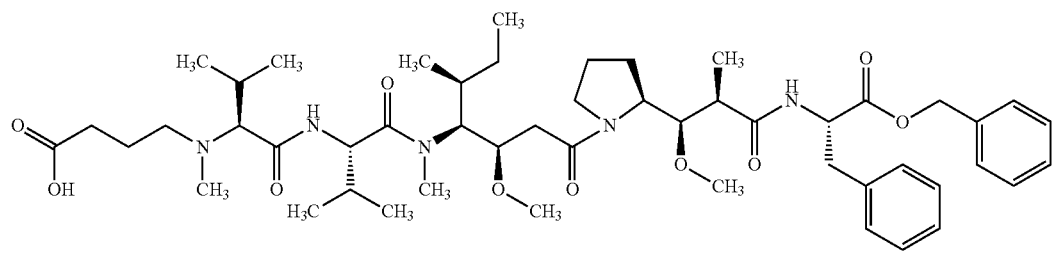 [SMILES: CC[C@H](C)[C@@H]([C@@H](CC(=O)N1CCC[C@H]1[C@H](OC)[C@@H](C)C(=O)N[C@@H](Cc1ccccc1)C(=O)OCc1ccccc1)OC)N(C)C(=O)[C@@H](NC(=O)[C@H](C(C)C)N(C)CCCC(=O)O)C(C)C]

53 mg (84 μmol) of N-[(9H-fluoren-9-ylmethoxy)carbonyl]-N-methyl-L-valyl-N-[(2R,3S,4S)-1-carboxy-2-methoxy-4-methylhexan-3-yl]-N-methyl-L-valinamide (intermediate 4) and 45 mg (84 μmol) of benzyl-N-{(2R,3R)-3-methoxy-2-methyl-3-[(2S)-pyrrolidin-2-yl]propanoyl}-L-phenylalaninate sodium trifluoracetate (intermediate 8) were absorbed in 2 ml of DMF, mixed with 19 μl of N,N-diisopropylethylamine, 14 mg (92 μmol) of HOBt, and 17.6 mg (92 μmol) of EDC and then stirred overnight at RT. Then, the reaction composition was evaporated and the residue purified by means of preparative HPLC. This way, 59 mg (68% o. th.) of Fmoc protected intermediate of N-[(9H-fluoren-9-ylmethoxy)carbonyl]-N-methyl-L-valyl-N-[(3R,4S,5S)-1-{(2S)-2-[(1R,2R)-3-{[(2S)-1-(benzyloxy)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained.

LC-MS (method 1): $R_t$=1.55 min; m/z=1044 (M+H)$^+$.

57 mg (0.055 mmol) of this intermediate were treated with 1.2 ml of piperidine in 5 ml Dichlormethane for elimination of the Fmoc protection group. Following evaporation and purification with the help of HPLC, 39 mg (76% o. th.) of the free amine intermediate of N-methyl-L-valyl-N-[(3R,4S,5S)-1-{(2S)-2-[(1R,2R)-3-{[(2S)-1-(benzyloxy)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide was obtained as sodium trifluoracetate.

HPLC (method 5): $R_t$=1.9 min;

LC-MS (method 1): $R_t$=1.01 min; m/z=822 (M+H)$^+$.

37 mg (0.045 mmol) of this intermediate were dissolved in 5 ml of dioxane/water (1:1) and treated in analogy producing example 6 with 15% aqueous solution of 4-ketobutyric acid in the presence of sodium cyanoborohydride. 16 mg (39% o. th.) of the title compound were obtained as a colorless foam.

HPLC (Method 5): $R_t$=2.1 min;

LC-MS (method 1): $R_t$=1.01 min; MS (ESIpos): m/z=908 (M+H)$^+$.

Example 6

N-(3-carboxypropyl)-N-methyl-L-valyl-N-[(3R,4S,5S)-1-{(2S)-2-[(1R,2R)-3-{[(2S,3S)-1-(benzyloxy)-1-oxo-3-phenylbutane-2-yl]amino}-1-methoxy-2-methyl-3-oxopropyl]pyrrolidin-1-yl}-3-methoxy-5-methyl-1-oxoheptan-4-yl]-N-methyl-L-valinamide

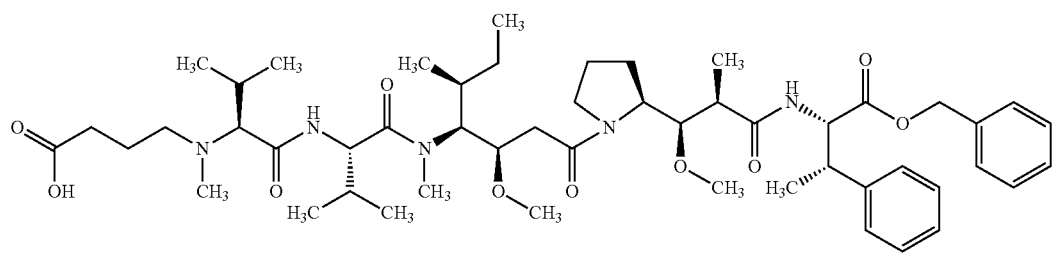 [SMILES: CC[C@H](C)[C@@H]([C@@H](CC(=O)N1CCC[C@H]1[C@H](OC)[C@@H](C)C(=O)N[C@H](C(=O)OCc1ccccc1)[C@@H](C)c1ccccc1)OC)N(C)C(=O)[C@@H](NC(=O)[C@H](C(C)C)N(C)CCCC(=O)O)C(C)C]

In the beginning the amine compound N-methyl-L-valyl-N-[(3R,4S,5S)-1-{(2S)-2-[(1R,2R)-3-{[(2S,3S)-1-(benzyloxy)-1-oxo-3-phenylbutane2-yl]amino}-1-methoxy-2-methyl-3-oxopropyl]pyrrolidin-1-yl}-3-methoxy-5-methyl-1-oxoheptan-4-yl]-N-methyl-L-valinamide analogous to the synthesis as described in example 5 on the basis of the intermediates 4 and 7 was produced.

30 mg (0.032 mmol) of this compound were dissolved in 6 ml of dioxane/water (1:1) and mixed with 41 μl (0.063 mmol) of 15% aqueous 4-ketobutyric acid solution. The batch was then stirred for 1 hour at 100° C. After cooling the mixture at RT, 2.2, mg (0.035 mmol) of sodium cyanoboro hydride were added and the composition adjusted to a pH value of 3 by adding approximately 300 μl 0.1 N hydrochloric acid. The batch was then stirred for 2 hours at 100° C. After cooling 41 μl (0.063 mmol) of 15% of 4-ketobutyric acid solution was added again and the batch stirred again for 1 hour at 100° C. Then another 2.2 mg (0.035 mmol) of sodium cyanoborohydride were added and then again adjusted to a pH value of 3 with 300 μl 0.1 N hydrochloric acid. Again, batch was stirred for 2 hours at 100° C. If the treatment was incomplete, this procedure was repeated a third time. The batch finally was evaporated and the raw product purified by means of preparative HPLC. 24 mg (82% o. th.) of the title compound were obtained as a colorless foam.

HPLC (method 5): $R_t$=1.9 min;

LC-MS (method 9): $R_t$=5.15 min; MS (ESIpos): m/z=922 $(M+H)^+$.

Example 7

N-(3-carboxypropyl)-N-methyl-L-valyl-N-[(3R,4S,5 S)-3-methoxy-1-{(2S)-2-[(1R,2R)-1-methoxy-2-methyl-3-{[(2S)-1-(1-naphthylmethoxy)-1-oxo-3-phenylpropane-2-yl]amino}-2-oxopropyl]pyrrolidin-1-yl}-5-methyl-1-oxoheptan-4-yl]-N-methyl-L-valinamide In the beginning, the amine compound N-methyl-L-valyl-N-[(3R,4S,5S)-3-methoxy-1-{(2S)-2-[(1R,2R)-1-methoxy-3-{[(2S)-1-methoxy-1-oxo-3-phenylpropane-2-yl]amino}-2-methyl-3-oxopropyl]pyrrolidin-1-yl}-5-methyl-1-oxoheptan-4-yl]-N-methyl-L-valinamide analogous to the synthesis as described in example 5 on the basis of the intermediates 4 and 11 was produced. Out of 7 mg (0.009 mmol) of this compound 2 mg (22% o. th.) of the title compound were obtained in analogy to the production of example 6, treated with 4-ketobutyric acid in the presence of sodium cyanoborohydride.

HPLC (method 5): $R_t$=1.9 min;

LC-MS (method 2): $R_t$=1.06 min; MS (ESIpos): m/z=832 $(M+H)^+$.

Example 8

N-(3-carboxypropyl)-N-methyl-L-valyl-N-[(3R,4S,5S)-1-{(2S)-2-[(1R,2R)-3-{[(2S)-1-(benzyloxy)-3-(1H-indol-3-yl)-1-oxopropane-2-yl]amino}-1-methoxy-2-methyl-3-oxopropyl]pyrrolidin-1-yl}-3-methoxy-5-methyl-1-oxoheptan-4-yl]-N-methyl-L-valinamide

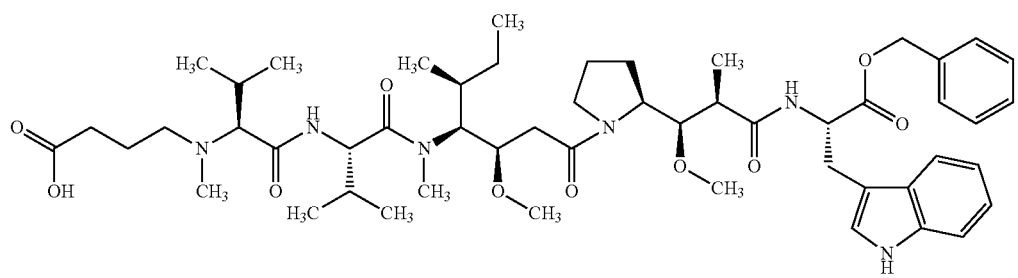

212 mg (411 μmol) of N-(tert.-butoxycarbonyl)-N-methyl-L-valyl-N-[(2R,3S,4S)-1-carboxy-2-methoxy-4-methyl-hexan-3-yl]-N-methyl-L-valinamide (intermediate 5) and 237 mg (411 μmol) of benzyl-N-{(2R,3R)-3-methoxy-2-methyl-3-[(2S)-pyrrolidin-2-yl]propanoyl}-L-tryptophanate sodium trifluoracetate (intermediate 12) were absorbed in 30 ml of DMF and mixed with 188 mg (493 μmol) of 0-(7-azabenzotriazol-1-yl)-N,N,N',N'-tetramethyluronium-hexafluorophosphate and 215 μl of N,N-diisopropylethylamine. The batch was stirred for 20 hours at RT, then evaporated under vacuum, and the residue purified by means of preparative HPLC. The product fractions were combined, evaporated and the residue dried in a high vacuum. A yield of 315 mg (80% o. th.) of the Boc protected intermediate of N-(tert.-butoxycarbonyl)-N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxo-

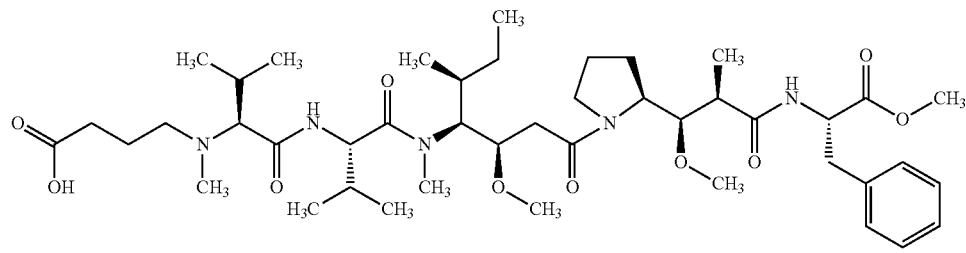 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@H](C(C)C)N(C)CCCC(=O)O)C(C)C]

propyl]pyrrolidin-1-yl}-3-methoxy-5-methyl-1-oxoheptan-4-yl]-N-methyl-L-valinamide was obtained as colorless foam.

LC-MS (method 1): $R_t$=1.45 min; m/z=961 $(M+H)^+$.

50 mg (52 μmol) of this intermediate were treated with 1 ml of piperidine in 9 ml of dichlormethane for cleavage of the Fmoc protection group. Following evaporation and purification with the help of HPLC, 29 mg (57% o. th.) of the free amine intermediate of N-methyl-L-valyl-N-[(3R,4S,5S)-1-{(2S)-2-[(1R,2R)-3-{[(2S)-1-(benzyloxy)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide was obtained as sodium trifluoracetate.

LC-MS (method 1): R=0.99 min; m/z=861 (M+H)⁺.

29 mg (0.03 mmol) of this intermediate were dissolved in 6 ml of dioxane/water (1:1) and mixed with 39 µl (0.059 mmol) of 15% aqueous 4-ketobutyric acid solution. The batch was then stirred for 1 hour at 100° C. After cooling the mixture at RT, 2 mg (0.033 mmol) of sodium cyanoboro hydride were added and the mixture adjusted to a pH value of 3 by adding approximately 300 µl 0.1 N hydrochloric acid. The batch was then stirred for 2 hours at 100° C. After cooling 39 µl (0.059 mmol) of 15% of 4-ketobutyric acid solution was added again and the batch stirred again for 1 hour at 100° C. Then another 2 mg (0.033 mmol) of sodium cyanoborohydride were added and then again adjusted to a pH value of 3 with 300 µl 0.1 N hydrochloric acid. The composition was then stirred for 2 hours at 100° C. Then the batch was poured on a 1:1 mixture of semi-saturated aqueous ammonium chloride solution and ethyl acetate. The organic phase was separated, scrubbed with saturated sodium hydride solution, dried over sodium hydride and evaporated. The residue was lyophilized from water/acetonitrile. 27 mg (94% o. th.) of the title compound were obtained as a colorless foam.

HPLC (method 5): $R_t$=2.2 min;

LC-MS (method 9): $R_t$=5.04 min; MS (ESIpos): m/z=947 (M+H)⁺.

Example 9

N-(3-carboxypropyl)-N-methyl-L-valyl-N-[(3R,4S,5S)-1-{(2S)-2-[(1R,2R)-3-({(2S)-1-[benzyl(methyl)amino]-1-oxo-3-phenylpropane-2-yl}amino)-1-methoxy-2-methyl-3-oxopropyl]pyrrolidin-1-yl}-3-methoxy-5-methyl-1-oxoheptan-4-yl]-N-methyl-L-valinamide

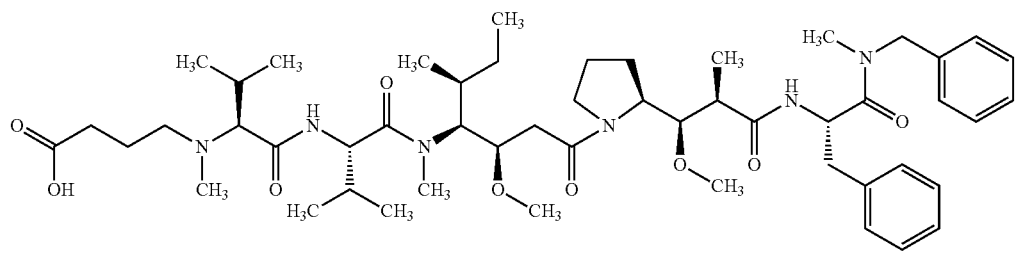 [SMILES: CC[C@H](C)[C@@H]([C@@H](CC(=O)N1CCC[C@H]1[C@H](OC)[C@@H](C)C(=O)N[C@@H](Cc1ccccc1)C(=O)N(C)Cc1ccccc1)OC)N(C)C(=O)[C@@H](NC(=O)[C@H](C(C)C)N(C)CCCC(=O)O)C(C)C]

In the beginning, the amine compound N-methyl-L-valyl-N-[(3R,4S,5S)-1-{(2S)-2-[(1R,2R)-3-({(2S)-1-[benzyl(methyl)amino]-1-oxo-3-phenylpropane-2-yl}amino)-1-methoxy-2-methyl-3-oxopropyl]pyrrolidin-1-yl}-3-methoxy-5-methyl-1-oxoheptan-4-yl]-N-methyl-L-valinamide analogous to the synthesis as described in example 5 on the basis of the intermediates 4 and 10 was produced. Out of 25 mg (0.026 mmol) of this compound 13 mg (54% o. th.) of the title compound were then obtained in analogy to the production of example 6 by means of treatment with 4-ketobutyric acid in the presence of sodium cyanoborohydride.

HPLC (method 5): $R_t$=2.2 min;

LC-MS (method 9): $R_t$=5.01 min; MS (ESIpos): m/z=921 (M+H)⁺.

Example 10

N-(3-carboxypropyl)-N-methyl-L-valyl-N-[(3R,4S,5S)-1-{(2S)-2-[(1R,2R)-3-({(1S,2R)-1-[(benzyloxy)carbonyl]-2-phenylcyclopropyl}amino)-1-methoxy-2-methyl-3-oxopropyl]pyrrolidin-1-yl}-3-methoxy-5-methyl-1-oxoheptan-4-yl]-N-methyl-L-valinamide

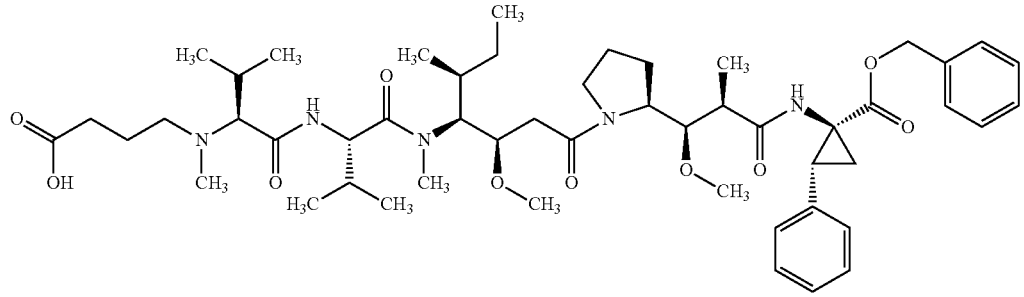 [SMILES: CC[C@H](C)[C@@H]([C@@H](CC(=O)N1CCC[C@H]1[C@H](OC)[C@@H](C)C(=O)N[C@@]1(C(=O)OCc2ccccc2)C[C@@H]1c1ccccc1)OC)N(C)C(=O)[C@@H](NC(=O)[C@H](C(C)C)N(C)CCCC(=O)O)C(C)C]

50 mg (73 µmol) of N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) and 28 mg (73 µmol) of benzyl-(1S,2R)-1-amino-2-phenyl-cyclopropancarboxylate sodium trifluoroacetate (intermediate 38) were absorbed in 5 ml of DMF and mixed with 42 mg (110 µmol) of O-(7-Azabenzotriazol-1-yl)-N,N,N',N'-tetramethyluronium-hexafluorophosphate and 38 µl of N,N-diisopropylethylamine. The batch was stirred for 5 hours at RT, then evaporated under vacuum, and the residue purified by means of preparative HPLC. The product fractions were mixed and evaporated. After lyophilization with dioxane/water, 35 mg (51% o. th.) of the Boc protected intermediate of N-(tert.-butoxycarbonyl)-N-methyl-L-valyl-N-[(3R,4S,5S)-1-{(2S)-2-[(1R,2R)-3-({(1S,2R)-1-[(benzyloxy)carbonyl]-2-phenylcyclopropyl}amino)-1-methoxy-2-methyl-3-oxopropyl]pyrrolidin-1-yl}-3-methoxy-5-methyl-1-oxoheptan-4-yl]-N-methyl-L-valinamide were obtained in the form of a colorless foam.

LC-MS (method 1): $R_t$=1.52 min; m/z 934 (M+H)$^+$.

35 mg of this intermediate were treated with 1 mg of sodium trifluoroacetate in 5 ml of dichlormethane for cleavage of the Boc protection group. Following evaporation and lyophilization with dioxane/water 34 mg (97% o. Th.) of the free amine intermediate of N-methyl-L-valyl-N-[(3R,4S,5S)-1-{(2S)-2-[(1R,2R)-3-({(1S,2R)-1-[(benzyloxy)carbonyl]-2-phenylcyclopropyl}amino)-1-methoxy-2-methyl-3-oxopropyl]pyrrolidin-1-yl}-3-methoxy-5-methyl-1-oxoheptan-4-yl]-N-methyl-L-valinamide were obtained as sodium trifluoroacetate.

LC-MS (method 1): $R_t$=0.91 min; m/z=834 (M+H)$^+$.

Out of 11 mg (0.011 mmol) of this intermediate 2.5 mg (24% o. th.) of the title compound were obtained in the form of a colorless foam in analogy to the production of example 6, by means of treatment with 4-ketobutyric acid in the presence of sodium cyanoborohydride.

HPLC (method 5): $R_t$=2.2 min;

LC-MS (method 9): $R_t$=5.1 min; MS (ESIpos): m/z=920 (M+H)$^+$.

Example 11

N-(3-carboxypropyl)-N-methyl-L-valyl-N-[(3R,4S,5S)-3-methoxy-1-{(2S)-2-[(1R,2R)-1-methoxy-2-methyl-3-oxo-3-{[(1S,2R)-2-phenyl-1-(propylcarbamoyl)cyclopropyl]amino}propyl]pyrrolidin-1-yl}-5-methyl-1-oxoheptan-4-yl]-N-methyl-L-valinamide

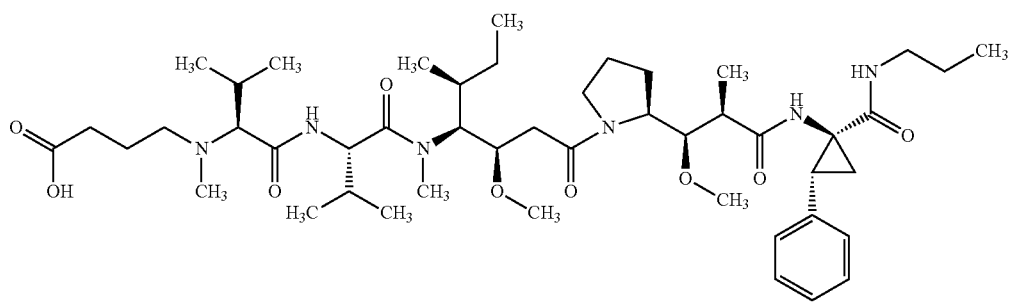 [SMILES: CCCNC(=O)[C@]1(NC(=O)[C@H](C)[C@@H](OC)[C@@H]2CCCN2C(=O)C[C@@H](OC)[C@H]([C@@H](C)CC)N(C)C(=O)[C@@H](NC(=O)[C@H](C(C)C)N(C)CCCC(=O)O)C(C)C)C[C@@H]1c1ccccc1]

First, the amine compound N-methyl-L-valyl-N-[(3R,4S,5S)-3-methoxy-1-{(2S)-2-[(1R,2R)-1-methoxy-2-methyl-3-oxo-3-{[(1S,2R)-2-phenyl-1-(propylcarbamoyl)cyclopropyl]amino}propyl]pyrrolidin-1-yl}-5-methyl-1-oxoheptan-4-yl]-N-methyl-L-valinamide was produced as sodium trifluoroacetate, analogous to the synthesis described in example 10 by means of coupling N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) with (1S,2R)-1-Amino-2-phenyl-N-propylcyclopropancarboxamide sodium trifluoroacetate (intermediate 16) in the presence of O-(7-Azabenzotriazol-1-yl)-N,N,N',N'-tetramethyluronium-hexafluorophosphate, followed by cleavage of the Boc protected group with the help of trifluoroacetic acid. Out of 14 mg (0.016 mmol) of this compound 11.3 mg (83% o. th.) of the title compound were obtained in analogy to the production of example 6, treated with 4-ketobutyric acid in the presence of sodium cyanoborohydride.

HPLC (method 5): $R_t$=1.9 min;

LC-MS (method 2): $R_t$=1.27 min; MS (ESIpos): m/z=871 (M+H)$^+$.

Example 12

N-(3-carboxypropyl)-N-methyl-L-valyl-N-[(3R,4S,5S)-1-{(2S)-2-[(1R,2R)-3-{[(1S,2R)-1-(ethoxycarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

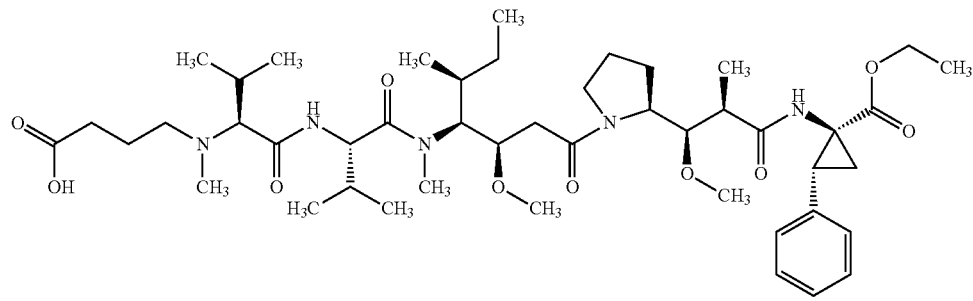 [SMILES: CCOC(=O)[C@]1(NC(=O)[C@H](C)[C@@H](OC)[C@@H]2CCCN2C(=O)C[C@@H](OC)[C@H]([C@@H](C)CC)N(C)C(=O)[C@@H](NC(=O)[C@H](C(C)C)N(C)CCCC(=O)O)C(C)C)C[C@@H]1c1ccccc1]

First, the amine compound N-methyl-L-valyl-N-[(3R,4S,5S)-1-{(2S)-2-[(1R,2R)-3-{[(1S,2R)-1-(ethoxycarbonyl)-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide was produced as sodium trifluoroacetate, analogous to the synthesis described in example 10 by means of coupling N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) with ethyl-(1S,2R)-1-amino-2-phenylcyclopropancarboxylate sodium trifluoroacetate (intermediate 17) in the presence of O-(7-Azabenzotriazol-1-yl)-N,N,N',N'-tetramethyluronium-hexafluorophosphate, followed by cleavage of the Boc protected group with the help of trifluoroacetic acid. Out of 70 mg (0.079 mmol) of this compound 46 mg (68% o. th.) of the title compound were obtained in analogy to the production of example 6, by means of treatment with 4-ketobutyric acid in the presence of sodium cyanoborohydride.

HPLC (method 5): $R_f$=1.9 min;

LC-MS (method 2): $R_f$=1.28 min; MS (ESIpos): m/z=858 (M+H)$^+$.

$^1$H-NMR (500 MHz, DMSO-d$_6$): δ=8.95 and 8.8 (2m, 1H), 8.85 and 8.7 (2s, 1H), 7.4-7.1 (m, 5H), 4.8 and 4.65 (2m, 1H), 4.55 (m, 1H), 4.12-3.95 (m, 2H), 3.9-3.8 (m, 1H), 3.8-3.4 (m, 5H), 3.35, 3.30, 3.20, 3.15, 3.10, 3.00, 2.81 and 2.79 (8s, 12H), 2.85-2.7 (m, 2H), 2.7-2.6 (m, 1H), 2.4-2.2 (m, 3H), 2.1-1.6 (m, 9H), 1.5-1.2 (m, 3H), 1.2-0.7 (m, 24H) [further signals hidden under peaks of solvent].

Example 13

N-(3-carboxypropyl)-N-methyl-L-valyl-N-[(3R,4S,5S)-1-{(2S)-2-[(1R,2R)-3-{[(2S)-1-amino-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

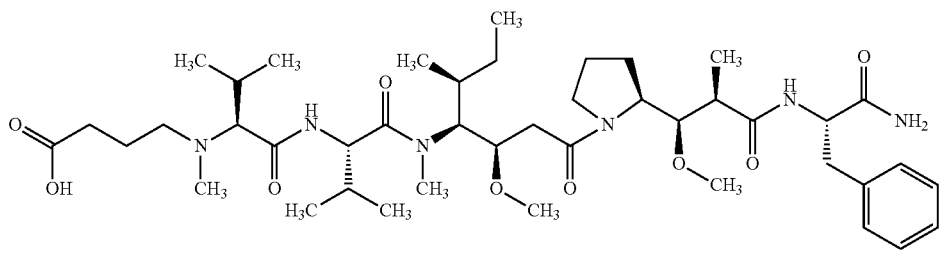 [SMILES: CC[C@H](C)[C@@H]([C@@H](CC(=O)N1CCC[C@H]1[C@H](OC)[C@@H](C)C(=O)N[C@@H](Cc1ccccc1)C(N)=O)OC)N(C)C(=O)[C@@H](NC(=O)[C@H](C(C)C)N(C)CCCC(=O)O)C(C)C]

First, the amine compound N-methyl-L-valyl-N-[(3R,4S,5S)-1-{(2S)-2-[(1R,2R)-3-{[(2S)-1-tert.-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide was produced as sodium trifluoroacetate, analogous to the synthesis described in example 10, by means of coupling N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) with L-phenylalaninamide-hydrochloride in the presence of O-(7-Azabenzotriazol-1-yl)-N,N,N',N'-tetramethyluronium-hexafluorophosphate, followed by cleavage of the Boc protected group with the help of trifluoroacetic acid. Out of 47 mg (0.049 mmol) of this compound 39 mg (96% o. th.) of the title compound were obtained in analogy to the production of example 6, treated with 4-ketobutyric acid in the presence of sodium cyanoborohydride.

HPLC (method 5): $R_f$=1.7 min;

LC-MS (method 9): $R_f$=4.44 min; MS (ESIpos): m/z=817 (M+H)$^+$.

$^1$H-NMR (500 MHz, DMSO-d$_6$): δ=8.95 and 8.8 (2m, 1H), 8.25 and 8.0 (2d, 1H), 7.45, 7.35 and 7.0 (3s, wide, 2H), 7.3-7.1 (m, 5H), 4.8-4.4 (2m, 3H), 3.95 (m, 1H), 3.82 (m, 1H), 3.72 (d, 1H), 3.22, 3.18, 3.15, 3.05 and 3.00 (5s, 9H), 2.85-2.7 (m, 4H), 2.45-1.6 (m, 12H), 1.5-1.2 (m, 3H), 1.1-0.7 (m, 21H) [further signals hidden under peaks of solvent].

Example 14

(3R,4S,7S,10S)-3-(2-{(2S)-2-[(1R,2R)-3-{[(2S)-1-(2-benzoylhydrazino)-1-oxo-3-phenylpropane-2yl]amino}-1-methoxy-2-methyl-3-oxopropyl]pyrrolidin-1-yl}-2-oxoethyl)-4-[(2S)-butane-2-yl]-7,10-diisopropyl-5,11-dimethyl-6,9-dioxo-2-oxa-5,8,11-triazapentadecan-15-acid

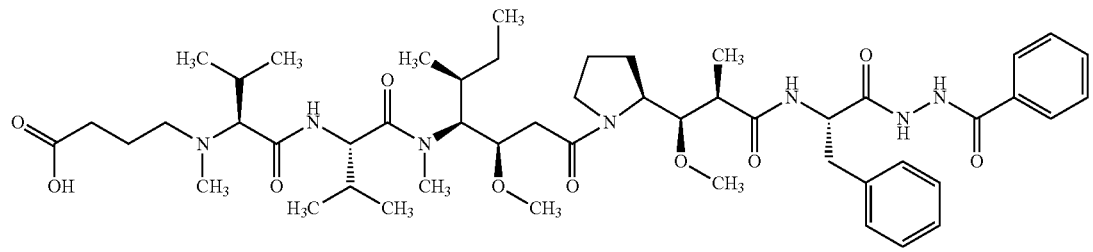 [SMILES: CC[C@H](C)[C@@H]([C@@H](CC(=O)N1CCC[C@H]1[C@H](OC)[C@@H](C)C(=O)N[C@@H](Cc1ccccc1)C(=O)NNC(=O)c1ccccc1)OC)N(C)C(=O)[C@@H](NC(=O)[C@H](C(C)C)N(C)CCCC(=O)O)C(C)C]

6.2 mg (6 µmol) of (2S)-N-[(3R,4S,5S)-1-{(2S)-2-[(1R,2R)-3-{[(2S)-1-(2-benzoylhydrazino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N,3-dimethyl-2-{[(2S)-3-methyl-2-(methylamino)butanoyl]amino}butanamide sodium trifluoroacetate (intermediate 37) and 8.3 µl of 15% aqueous amber aldehyde acid solution (13 µmol) were dissolved in 235 µl of a 1:1-dioxane/water composition and heated at a temperature of 100° C. After a short cooling period 0.5 mg (7 µmol) of sodium cyanoborohydride were added. The reaction composition was formulated with 0.1 of N hydrochloric acid to pH 3 and heated for 2 hours at a temperature of 100° C. It was reheated again for 2 hours at 100° C. after the same amounts of amber aldehyde acid solution, sodium cyanoborohydride, and hydrochloric acid had been added once again. Afterwards, the reaction composition had been separated directly by means of preparative HPLC. The yield was 4.1 mg (68% o. th.) of the title compound.

LC-MS (method 1): $R_t$=0.86 min; m/z=936 (M+H)$^+$.

$^1$H-NMR (500 MHz, DMSO-d$_6$): δ [ppm]=0.71-0.81 (m, 3H), 0.82-1.02 (m, 15H), 1.05 (d, 2H), 1.19-1.51 (m, 3H), 1.56-1.89 (m, 3H), 1.89-2.12 (m, 2H), 2.18-2.44 (m, 5H), 2.71-2.90 (m, 3H), 2.94-3.28 (m, 10H), 3.36-3.67 (m, 3H), 3.71-4.02 (m, 1H), 4.53-4.91 (m, 3H), 7.14-7.20 (m, 1H), 7.24 (dd, 2H), 7.31 (d, 1H), 7.35 (d, 1H), 7.52 (dd, 2H), 7.60 (dd, 1H), 7.92 (d, 2H), 8.24 and 8.46 (2d, 1H), 10.2-10.3 (m, 1H), 10.44-10.52 (m, 1H) [further signals hidden under peaks of solvent].

Example 15

N-(3-carboxypropyl)-N-methyl-L-valyl-N-[(3R,4S,5S)-1-{(2S)-2-[(1R,2R)-3-{[(2S)-1-(benzylamino)-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide

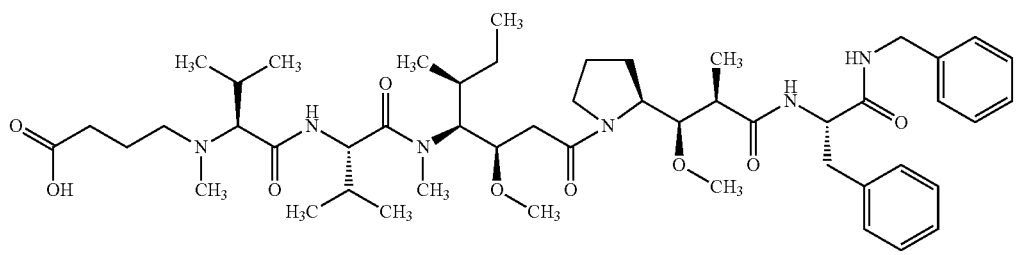 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCc1ccccc1)OC)N(C)C(=O)[C@@H](NC(=O)[C@H](C(C)C)N(C)CCCC(=O)O)C(C)C]

36 mg (43 µmol) of N-(tert.-butoxycarbonyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (intermediate 39) and 4.6 mg (43 µmol) of benzyl amine were absorbed in 5 ml of DMF, mixed with 7.5 µl (88 µmol) of N,N-diisopropylethylamine, 10 mg (65 µmol) of HOBt as well as 10 mg (52 µmol) of EDC, and then stirred over night at RT. Then, the reaction composition was evaporated and the residue purified by means of preparative HPLC. This way, 29 mg (73% o. th.) of Fmoc protected intermediate of N-(tert.-butoxycarbonyl)-N-methyl-L-valyl-N-[(3R,4S,5S)-1-{(2S)-2-[(1R,2R)-3-{[(2S)-1-(benzylamino)-1-oxo-3-phenylpropane-2-yl]amino}-1- methoxy-2-methyl-3-oxopropyl]pyrrolidin-1-yl}-3-methoxy-5-methyl-1-oxoheptan-4-yl]-N-methyl-L-valinamide were obtained.

LC-MS (method 1): $R_t$=1.43 min; m/z=921 (M+H)$^+$.

29 mg of this intermediate were treated with 1 mg of sodium trifluoracetate in 6 ml of dichlormethane for cleavage of the Boc protection group. Following evaporation and lyophilization with dioxane/water, 30 mg (quant.) of the free amine intermediate of N-methyl-L-valyl-N-[(3R,4S,5S)-1-{(2S)-2-[(1R,2R)-3-{[(2S)-1-(benzylamino)-1-oxo-3-phenylpropane-2-yl]amino}-1-methoxy-2-methyl-3-oxopropyl]pyrrolidin-1-yl}-3-methoxy-5-methyl-1-oxoheptan-4-yl]-N-methyl-L-valinamide were obtained as sodium trifluoracetate.

LC-MS (method 1): $R_t$=0.95 min; m/z=821 (M+H)$^+$.

Out of 17 mg (0.018 mmol) of this intermediate 13 mg (80% o. th.) of the title compound were obtained in the form of a colorless foam in analogy to the production of example 6, treated with 4-ketobutyric acid in the presence of sodium cyanoborohydride.

HPLC (method 6): $R_t$=1.7 min;

LC-MS (method 9): $R_t$=4.97 min; MS (ESIpos): m/z=907 (M+H)$^+$.

Example 16

N-(3-carboxypropyl)-N-methyl-L-valyl-N-[(3R,4S,5S)-1-{(2S)-2-[(1R,2R)-3-{[(2S)-1-(benzyl-amino)-3-(1H-indol-3-yl)-1-oxopropane-2-yl]amino}-1-methoxy-2-methyl-3-oxopropyl]pyrrolidin-1-yl}-3-methoxy-5-methyl-1-oxoheptan-4-yl]-N-methyl-L-valinamide

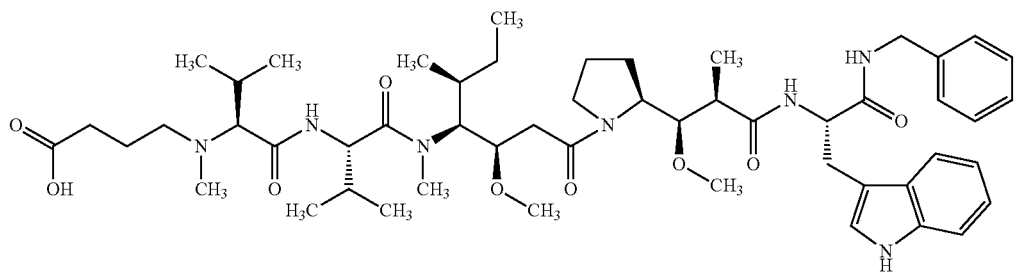 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)NCc1ccccc1)OC)N(C)C(=O)[C@@H](NC(=O)[C@H](C(C)C)N(C)CCCC(=O)O)C(C)C]

First, the amine compound N-Methyl-L-valyl-N-[(3R,4S,5S)-1-{(2S)-2-[(1R,2R)-3-{[(2S)-1-(benzylamino)-3-(1H-indol-3-yl)-1-oxopropane-2-yl]amino}-1-methoxy-2-methyl-3-oxo-propyl]pyrrolidin-1-yl}-3-methoxy-5-methyl-1-oxoheptan-4-yl]-N-methyl-L-valinamide was produced as sodium trifluoroacetate, analogous to the synthesis described in example 10 by means of coupling N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide sodium trifluoroacetate (intermediate 15) with N-benzyl-L-tryptophanamide (intermediate 40) in the presence of O-(7-Azabenzotriazol-1-yl)-N,N,N',N'-tetramethyluronium-hexafluorophosphate, followed by cleavage of the Boc protected group with the help of trifluoroacetic acid. Out of 10 mg (0.01 mmol) of this compound 2.5 mg (26% o. th.) of the title compound were obtained in analogy to the production of example 6, by means of treatment with 1-ketobutyric acid in the presence of sodium cyanoborohydride.

HPLC (method 6): $R_t$=1.7 min;

LC-MS (method 2): $R_t$=1.13 min; MS (ESIpos): m/z=946 (M+H)$^+$.

Example 17

N-(3-carboxypropyl)-N-methyl-L-valyl-N-[(3R,4S,5S)-1-{(2S)-2-[(1R,2R)-3-{[(1S,2R)-1-carbamoyl-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide

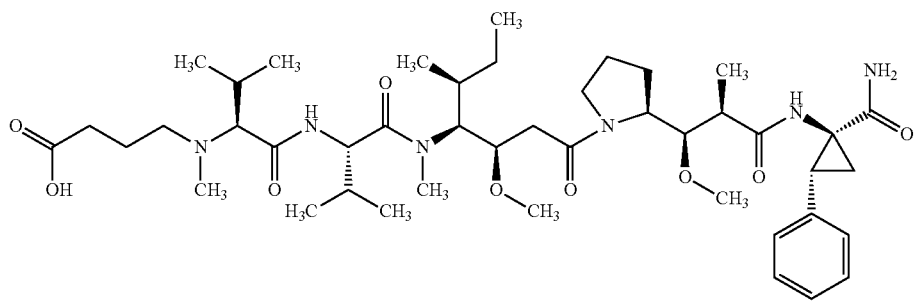 [SMILES: CC[C@H](C)[C@@H]([C@@H](CC(=O)N1CCC[C@H]1[C@H](OC)[C@@H](C)C(=O)N[C@@]1(C(N)=O)C[C@@H]1c1ccccc1)OC)N(C)C(=O)[C@@H](NC(=O)[C@H](C(C)C)N(C)CCCC(=O)O)C(C)C]

First, the amine compound N-methyl-L-valyl-N-[(3R,4S,5S)-1-{(2S)-2-[(1R,2R)-3-{[(1S,2R)-1-carbamoyl-2-phenylcyclopropyl]amino}-1-methoxy-2-methyl-3-oxopropyl]pyrrolidin-1-yl}-3-methoxy-5-methyl-1-oxoheptan-4-yl]-N-methyl-L-valinamide was produced as sodium trifluoroacetate, analogous to the synthesis described in example 10 by means of coupling N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) with (1S,2R)-1-amino-2-phenylcyclopropancarboxamide sodium trifluoroacetate (intermediate 41) in the presence of O-(7-Azabenzotriazol-1-yl)-N,N,N',N'-tetramethyluronium-hexafluorophosphate, followed by cleavage of the Boc protected group with the help of trifluoroacetic acid. Out of 15 mg (0.0175 mmol) of this compound 11 mg (76% o. th.) of the title compound were obtained in analogy to the production of example 6, by means of treatment with 4-ketobutyric acid in the presence of sodium cyanoborohydride.

HPLC (method 5): $R_t$=1.7 min;

LC-MS (method 9): $R_t$=4.66 min; MS (ESIpos): m/z=829 (M+H)$^+$.

Example 18

N-(3-carboxypropyl)-N-methyl-L-valyl-N-[(3R,4S,5S)-1-{(2S)-2-[(1R,2R)-3-{[(2S)-1-amino-3-(1H-indol-3-yl)-1-oxopropane2-yl]amino}-1-methoxy-2-methyl-3-oxopropyl]pyrrolidin-1-yl}-3-methoxy-5-methyl-1-oxoheptan-4-yl]-N-methyl-L-valinamide

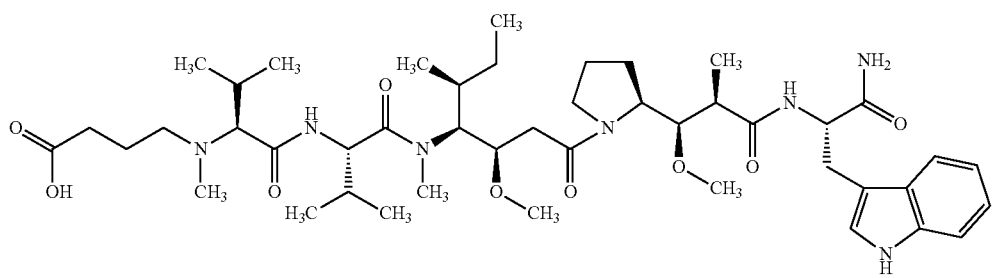 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCC(=O)O)C(C)C]

First, the amine compound N-methyl-L-valyl-N-[(3R,4S,5S)-1-{(2S)-2-[(1R,2R)-3-{[(2S)-1-amino-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide was produced as sodium trifluoroacetate analogous to the syntheses described in the examples 5 and 10 by means of coupling N-[(9H-fluoren-9-ylmethoxy)carbonyl]-N-methyl-L-valyl-N-[(2R,3S,4S)-1-carboxy-2-methoxy-4-methylhexane-3-yl]-N-methyl-L-valinamide (intermediate 4) and N$^\alpha$-{(2R,3R)-3-methoxy-2-methyl-3-[(2S)-pyrrolidin-2-yl]propanoyl}-L-tryptophanamide sodium trifluoroacetate (intermediate 42) in the presence of O-(7-Azabenzotriazol-1-yl)-N,N,N',N'-tetramethyluronium-hexafluorophosphate, followed by cleavage of the Fmoc protected group with the help of piperidine. Out of 78 mg (0.088 mmol) of this compound 68 mg (90% o. th.) of the title compound were obtained in analogy to the production of example 6, by means of treatment with 4-ketobutyric acid in the presence of sodium cyanoborohydride.

HPLC (method 6): $R_t$=1.8 min;

LC-MS (method 9): $R_t$=4.49 min; MS (ESIpos): m/z=856 (M+H)$^+$.

Example 19

N-(5-carboxypropyl)-N-methyl-L-valyl-N-[(3R,4S,5S)-1-{(2S)-2-[(1R,2R)-3-{[(2S)-1-amino-3-(1H-indol-3-yl)-1-oxopropane2-yl]amino}-1-methoxy-2-methyl-3-oxopropyl]pyrrolidin-1-yl}-3-methoxy-5-methyl-1-oxoheptan-4-yl]-N-methyl-L-valinamide

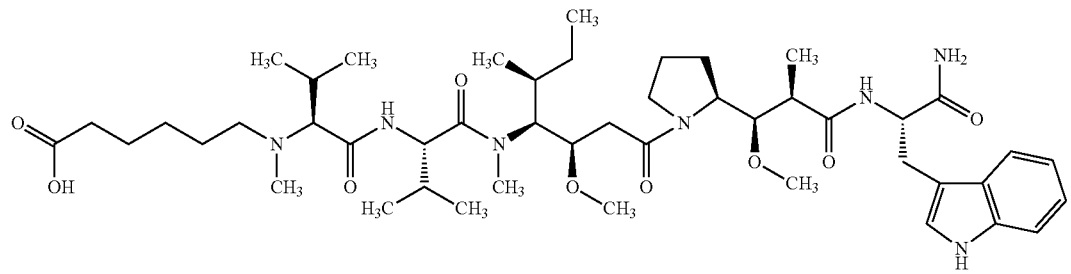 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(N)=O)OC)N(C)C(=O)[C@@H](NC(=O)[C@H](C(C)C)N(C)CCCCCC(=O)O)C(C)C]

The title compound was produced analogous to the synthesis of example 18 of 20 mg (26 μmol) of N-methyl-L-valyl-N-[(3R,4S,5S)-1-{(2S)-2-[(1R,2R)-3-{[(2S)-1-amino-3-(1H-indol-3yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide sodium trifluoroacetate with 6-oxohexan-acid in the presence of sodium cyanoborohydride.

Yield: 5 mg (25% o. th.)

HPLC (method 6): $R_t$=1.6 min;

LC-MS (method 11): $R_t$=0.72 min; MS (ESIpos): m/z=884 (M+H)$^+$.

Example 20

N-(3-carboxypropyl)-N-methyl-L-valyl-N-[(3R,4S,5S)-1-{(2S)-2-[(1R,2R)-3-{[(2S)-1-tert.-butoxy-1-oxo-3-phenylpropane2-yl]amino}-1-methoxy-2-methyl-3-oxopropyl]pyrrolidin-1-yl}-3-methoxy-5-methyl-1-oxoheptan-4-yl]-N-methyl-L-valinamide

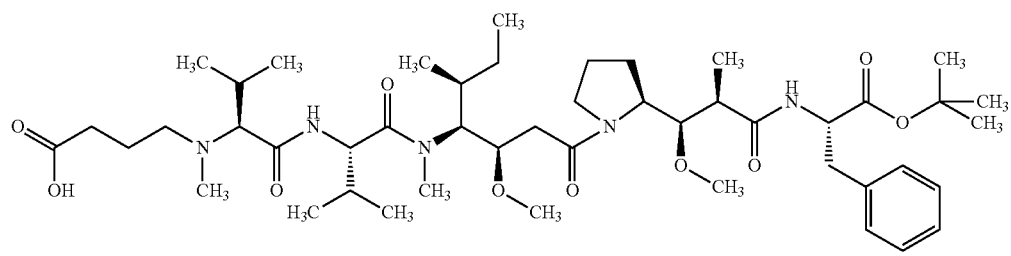 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC(C)(C)C)OC)N(C)C(=O)[C@@H](NC(=O)[C@H](C(C)C)N(C)CCCC(=O)O)C(C)C]

First, the amine compound N-methyl-L-valyl-N-[(3R,4S,5S)-1-{(2S)-2-[(1R,2R)-3-{[(2S)-1-tert.-butoxy-1-oxo-3-phenylpropan-2-yl]amino}-1-methoxy-2-methyl-3-oxopropyl]pyrrolidin-1-yl}-3-methoxy-5-methyl-1-oxoheptan-4-yl]-N-methyl-L-valinamide was produced as sodium trifluoroacetate, analogous to the synthesis described in example 16, by means of coupling N-(tert-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) with tert-Butyl-L-phenylalaninate-hydrochloride in the presence of O-(7-Azabenzotriazol-1-yl)-N,N,N',N'-tetramethyluronium-hexafluorophosphate, followed by careful cleavage of the Boc protected group with the help of trifluoroacetic acid and maintaining the tert-butyl ester group (stirring it for 40 minutes at RT with 10% sodium trifluoroacetate in dichlormethane). Out of 22 mg (0.02 mmol, 80% purity) of this compound 16 mg (94% o. th.) of the title compound were obtained in analogy to the production of example 1, treated with 4-ketobutyric acid in the presence of sodium cyanoborohydride.

HPLC (method 5): $R_t$=2.0 min;

LC-MS (method 9): $R_t$=5.05 min; MS (ESIpos): m/z=874 (M+H)$^+$.

Example 21

N-(3-carboxypropyl)-N-methyl-L-valyl-N-[(3R,4S,5S)-1-{(2S)-2-[(1R,2R)-3-{[(2S)-1-tert.-butoxy-3-(1H-indol-3-yl)-1-oxopropane-2-yl]amino}-1-methoxy-2-methyl-3-oxopropyl]pyrrolidin-1-yl}-3-methoxy-5-methyl-1-oxoheptan-4-yl]-N-methyl-L-valinamide

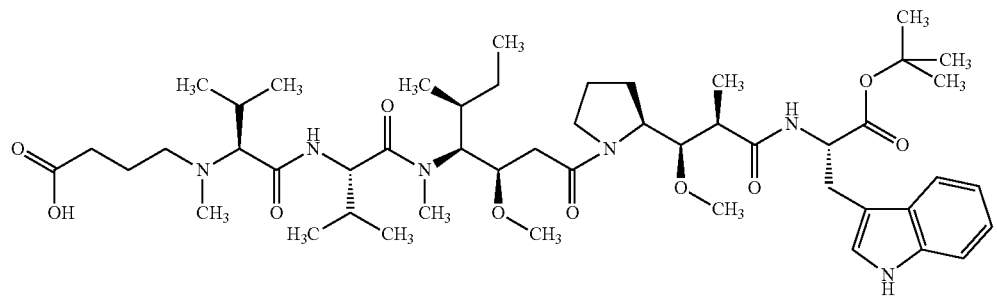 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)OC(C)(C)C)OC)N(C)C(=O)[C@@H](NC(=O)[C@H](C(C)C)N(C)CCCC(=O)O)C(C)C]

The title compound was produced over three stages in analogy to the synthesis described in example 20, based on 230 mg (336 μmol) of N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) and tert.-butyl-L-tryptophanate-hydrochloride.

Yield: 95 mg (31% o. th. over three stages)
HPLC (method 5): $R_t$=2.0 min;
LC-MS (method 9): $R_t$=5.05 min; MS (ESIpos): m/z=913 (M+H)$^+$.

Example 22

N-(3-carboxypropyl)-N-methyl-L-valyl-N-[(3R,4S,5S)-1-{(2S)-2-[(1R,2R)-3-{[(1S)-1-carboxy-2-(1H-indol-3-yl)ethyl]amino}-1-methoxy-2-methyl-3-oxopropyl]pyrrolidin-1-yl}-3-methoxy-5-methyl-1-oxoheptan-4-yl]-N-methyl-L-valinamide

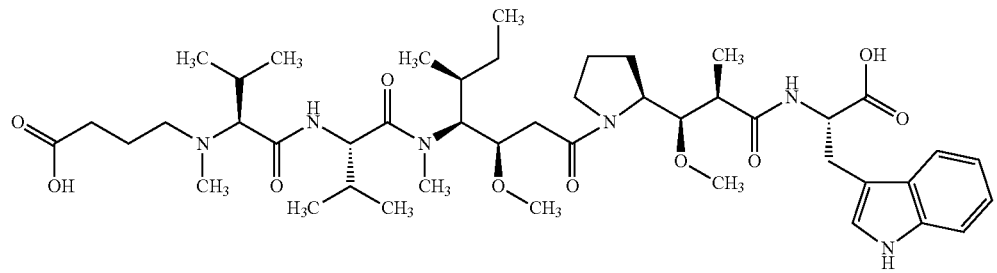 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)O)OC)N(C)C(=O)[C@@H](NC(=O)[C@H](C(C)C)N(C)CCCC(=O)O)C(C)C]

8 mg (9 μmol) of the compound of example 21 were stirred for 4 hours with 1 ml of trifluoroacetic acid in 3 ml of dichlormethane at RT. After the batch had been evaporated under vacuum, the raw product was purified by means of preparative HPLC.

Yield: 3 mg (37% o. th.)
LC-MS (method 1): $R_t$=0.77 min; MS (ESIpos): m/z=857 (M+H)$^+$.

Example 23

N-(3-carboxypropyl)-N-methyl-L-valyl-N-[(3R,4S, 5S)-3-methoxy-1-{(2S)-2-[(1R,2R)-1-methoxy-2-methyl-3-{[(2S)-1-(morpholin-4-yl)-1-oxo-3-phenyl-propane-2-yl]amino}-3-oxopropyl]pyrrolidin-1-yl}-5-methyl-1-oxoheptan-4-yl]-N-methyl-L-valinamide

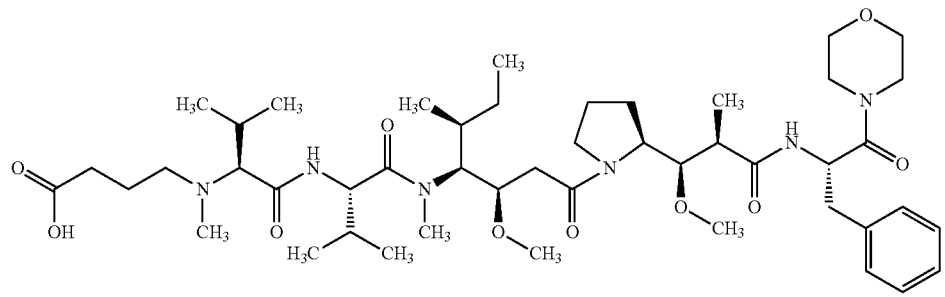 [SMILES: CC[C@H](C)[C@@H]([C@@H](CC(=O)N1CCC[C@H]1[C@H](OC)[C@@H](C)C(=O)N[C@@H](Cc1ccccc1)C(=O)N1CCOCC1)OC)N(C)C(=O)[C@@H](NC(=O)[C@H](C(C)C)N(C)CCCC(=O)O)C(C)C]

First, the amine compound N-methyl-L-valyl-N-[(3R,4S, 5S)-3-methoxy-1-{(2S)-2-[(1R,2R)-1-methoxy-2-methyl-3-{[(2S)-1-(morpholin-4-yl)-1-oxo-3-phenylpropane-2-yl]amino}-3-oxopropyl]pyrrolidin-1-yl}-5-methyl-1-oxoheptan-4-yl]-N-methyl-L-valinamide was produced as sodium trifluoroacetate, analogous to the synthesis described in example 15 by means of coupling N-(tert.-butoxycarbonyl)-N-methyl-L-valyl-N-[(3R,4S,5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-N-methyl-L-valinamide (intermediate 39) with morpholine in the presence of EDC and HOBt, followed by cleavage of the Boc-protected group with the help of trifluoroacetic acid. Out of 30 mg (0.033 mmol) of this compound 22 mg (76% o. th.) of the title compound were then obtained in analogy to the production of example 1, by means of treatment with 4-ketobutyric acid in the presence of sodium cyanoborohydride.

HPLC (method 6): $R_t$=1.6 min;
LC-MS (method 9): $R_t$=4.58 min; MS (ESIpos): m/z=887 $(M+H)^+$.

Example 24

N-(3-carboxypropyl)-N-methyl-L-valyl-N-[(3R,4S, 5S)-1-{(2S)-2-[(1R,2R)-3-{[(1S)-1-carboxy-2-phenylethyl]amino}-1-methoxy-2-methyl-3-oxopropyl]pyrrolidin-1-yl}-3-methoxy-5-methyl-1-oxoheptan-4-yl]-methyl-L-valinamide

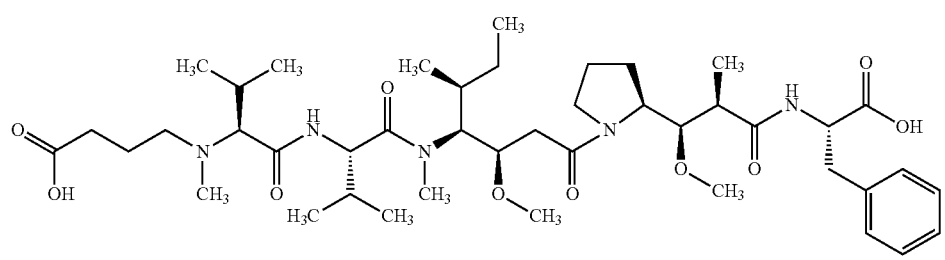 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)CCCC(=O)O)C(C)C]

0.4 mg (0.5 μmol) of the compound of example 20 were absorbed in 1 ml of dichlormethane and mixed with 1 ml of trifluoroacetic acid. After 1 hour of stirring at RT the formulation was evaporated and the residue lyophilized with dioxane/water. 0.37 mg (99% o. th.) of the title compound were obtained as a colorless foam.

HPLC (method 5): $R_t$=1.6 min;
LC-MS (method 1): $R_t$=0.8 min; MS (ESIpos): m/z=818 (M+H)$^+$.

Example 25

N-(3-carboxypropyl)-N-methyl-L-valyl-N-[(3R,4S,5S)-1-{(2S)-2-[(1R,2R)-3-{[(2S,3R)-1-(benzylamino)-3-hydroxy-1-oxobutane-2-yl]amino}-1-methoxy-2-methyl-3-oxopropyl]pyrrolidin-1-yl}-3-methoxy-5-methyl-1-oxoheptan-4-yl]-N-methyl-L-valinamide

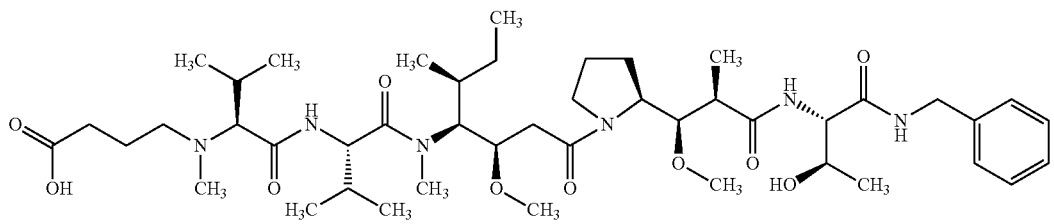 [SMILES: CC[C@H](C)[C@@H]([C@@H](CC(=O)N1CCC[C@H]1[C@H](OC)[C@@H](C)C(=O)N[C@H](C(=O)NCc1ccccc1)[C@@H](C)O)OC)N(C)C(=O)[C@@H](NC(=O)[C@H](C(C)C)N(C)CCCC(=O)O)C(C)C]

First, the amine compound N-methyl-L-valyl-N-[(3R,4S,5S)-1-{(2S)-2-[(1R,2R)-3-{[(2S,3R)-1-(benzylamino)-3-hydroxy-1-oxobutan-2-yl]amino}-1-methoxy-2-methyl-3-oxopropyl]pyrrolidin-1-yl}-3-methoxy-5-methyl-1-oxoheptan-4-yl]-N-methyl-L-valinamide was produced as sodium trifluoroacetate, in analogy to the synthesis described in example 16 by means of coupling N-(tert.-butoxycarbonyl)-N-methyl-L-valyl-N-[(3R,4S,5S)-1-{(2S)-2-[(1R,2R)-2-carboxy-1-methoxypropyl]pyrrolidin-1-yl}-3-methoxy-5-methyl-1-oxoheptan-4-yl]-N-methyl-L-valinamide (intermediate 15) with N-benzyl-L-threoninamide sodium trifluoroacetate in the presence of O-(7-Azabenzotriazol-1-yl)-N,N,N',N'-tetramethyluronium-hexafluorophosphate, followed by cleavage of the Boc protected group with the help of trifluoroacetic acid. Out of 21 mg (0.024 mmol) of this compound 20 mg (97% o. th.) of the title compound were obtained in analogy to the production of example 1, by means of treatment with 4-ketobutyric acid in the presence of sodium cyanoborohydride.

HPLC (method 5): $R_t$=1.5 min;
LC-MS (method 9): $R_t$=4.49 min; MS (ESIpos): m/z=861 (M+H)$^+$.

Example 26

N-(3-carboxypropyl)-N-methyl-L-valyl-N-[(3R,4S,5S)-3-methoxy-1-{(2S)-2-[(1R,2R)-1-methoxy-3-{[(2S)-1-{[4-(methoxycarbonyl)benzyl]oxy}-3-phenylpropane-2-yl]amino}-2-methyl-3-oxopropyl]pyrrolidin-1-yl}-5-methyl-1-oxoheptan-4-yl]-N-methyl-L-valinamide

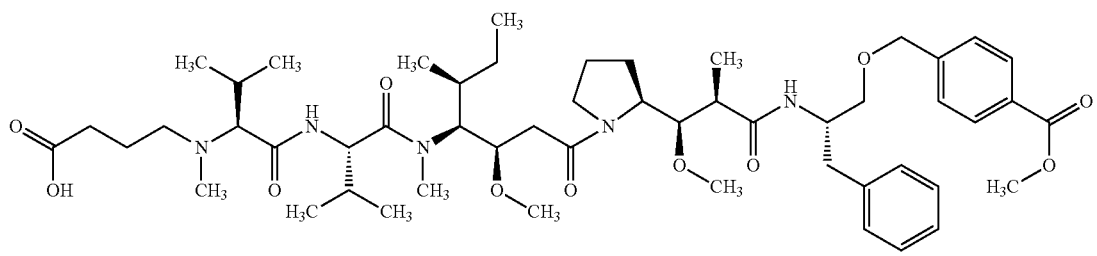 [SMILES: CC[C@H](C)[C@@H]([C@@H](CC(=O)N1CCC[C@H]1[C@H](OC)[C@@H](C)C(=O)N[C@H](COCc1ccc(C(=O)OC)cc1)Cc1ccccc1)OC)N(C)C(=O)[C@@H](NC(=O)[C@H](C(C)C)N(C)CCCC(=O)O)C(C)C]

11.5 mg (12 µmol) of N-methyl-L-valyl-N-[(3R,4S,5S)-3-methoxy-1-{(2S)-2-[(1R,2R)-1-methoxy-3-{[(2S)-1-{[4-(methoxycarbonyl)benzyl]oxy}-3-phenylpropane-2-yl]amino}-2-methyl-3-oxopropyl]pyrrolidin-1-yl}-5-methyl-1-oxoheptan-4-yl]-N-methyl-L-valinamide sodium trifluoroacetate (intermediate 46) were dissolved in 0.7 ml of dioxane/water (1:1) and treated in analogy to example 1 with aqueous solution of 4-ketobutyric acid in the presence of sodium cyanoborohydride. Following lyophilization from dioxane, the yield was 8.3 mg (74% o. th.) of the title compound in the form of a white solid substance.

LC-MS (method 1): R$_t$=0.95 min; MS (ESIpos): m/z=953 (M+H)$^+$.

Example 27

N-(3-carboxypropyl)-N-methyl-L-valyl-N-[(3R,4S,5S)-1-{(2S)-2-[(1R,2R)-3-({(2S)-1-[(4-carboxybenzyl)oxy]-3-phenylpropane-2-yl}amino)-1-methoxy-2-methyl-3-oxopropyl]pyrrolidin-1-yl}-3-methoxy-5-methyl-1-oxoheptan-4-yl]-N-methyl-L-valinamide

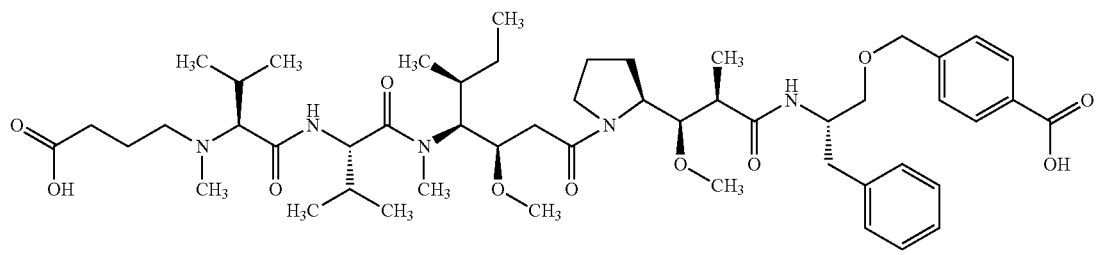 [SMILES: CC[C@H](C)[C@@H]([C@@H](CC(=O)N1CCC[C@H]1[C@H](OC)[C@@H](C)C(=O)N[C@H](COCc1ccc(C(=O)O)cc1)Cc1ccccc1)OC)N(C)C(=O)[C@@H](NC(=O)[C@H](C(C)C)N(C)CCCC(=O)O)C(C)C]

7.5 mg (8 µmol) of N-(3-carboxypropyl)-N-methyl-L-valyl-N-[(3R,4S,5S)-3-methoxy-1-{(2S)-2-[(1R,2R)-1-methoxy-3-{[(2S)-1-{[4-(methoxycarbonyl)benzyl]oxy}-3-phenylpropane-2-yl]amino}-2-methyl-3-oxopropyl]pyrrolidin-1-yl}-5-methyl-1-oxoheptan-4-yl]-N-methyl-L-valinamide (example 26) were dissolved in 0.25 ml of THF/water (1:1). 0.8 mg (32 µmol) of lithium hydroxide were added and the batch stirred for 3 hours at RT. Then, the reaction composition was acidized with 1 N hydrochloric acid and extracted three times with 5 ml of ethyl acetate each. The organic phases were dried over magnesium sulphate and evaporated in a vacuum. Following lyophilization from dioxane, the yield was 2.3 mg (71% purity, 22% o. th.) of the title compound in the form of a white solid substance.

LC-MS (method 1): R$_t$=0.91 min; MS (ESIpos): m/z=939 (M+H)$^+$.

Example 28

N-(5-carboxypentyl)-N-methyl-L-valyl-N-[(3R,4S,5S)-1-{(2S)-2-[(1R,2R)-3-{[(2S)-1-(benzylamino)-3-(1H-indol-3-yl)-1-oxopropane-2-yl]amino}-1-methoxy-2-methyl-3-oxopropyl]pyrrolidin-1-yl}-3-methoxy-5-methyl-1-oxoheptan-4-yl]-N-methyl-L-valinamide

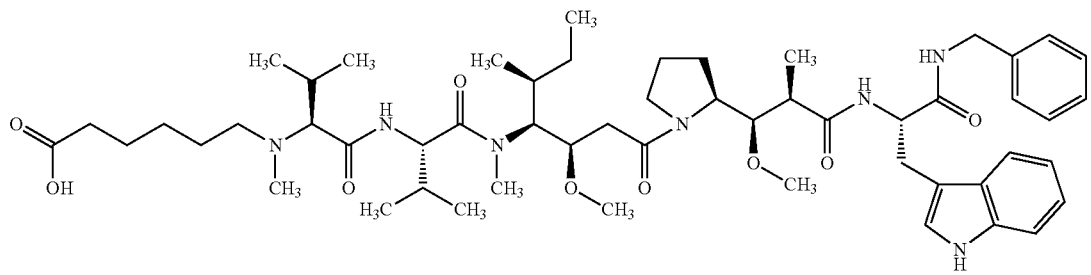 [SMILES: CC[C@H](C)[C@@H]([C@@H](CC(=O)N1CCC[C@H]1[C@H](OC)[C@@H](C)C(=O)N[C@@H](Cc1c[nH]c2ccccc12)C(=O)NCc1ccccc1)OC)N(C)C(=O)[C@@H](NC(=O)[C@H](C(C)C)N(C)CCCCCC(=O)O)C(C)C]

The title compound was produced analogous to the synthesis of example 16 by treatment of 100 mg (103 µmol) of N-methyl-L-valyl-N-[(3R,4S,5S)-1-{(2S)-2-[(1R,2R)-3-{[(2S)-1-(benzylamino)-3-(1H-indol-3-yl)-1-oxopropan-2-yl]amino}-1-methoxy-2-methyl-3-oxopropyl]pyrrolidin-1-yl}-3-methoxy-5-methyl-1-oxoheptan-4-yl]-N-methyl-L-valinamide sodium trifluoroacetate with 6-oxohexan-acid in the presence of sodium cyanoborohydride.

Yield: 40 mg (40% o. th.)

HPLC (method 5): $R_t$=1.9 min;

LC-MS (method 1): $R_t$=0.92 min; MS (ESIpos): m/z=974 (M+H)$^+$.

B. Evaluation of Biological Efficacy

The biological activity of the innovative compounds can be demonstrated by means of in vitro and in vivo studies, as known by the average experts. The pharmacological and pharmacokinetic properties of the inventive compounds, for instance, can be determined by means of the following assays:

B-1. Determination of Anti-proliferative Effects of Renal Cell Carcinoma 786-0 Cell Line:

A defined number of cells of the human renal carcinoma cell line 786-0 were cultured in a 96 well micro titer plate in rich medium (2500 or 7.000 cells/well) and then incubated over night at 37° C./5% CO2. After 18 hours the seed medium was replaced by a serum free medium or medium with 2% FCS. The treatment began with measuring out the respective test substances in varying concentrations ($10^{-5}$ M to $10^{-14}$ M). Incubation times of between 48 hours and 96 hours were chosen. The proliferation was determined by means of the MTT assay (ATCC, Manassas, Va., USA, catalogue no. 30-1010K). After completion of incubation period the MTT reagent was incubated with the cells for 4 hours before lysis occurred over night by measuring out the detergent. The created stain was detected at 570 nm. The proliferation of the cells, which were treated identically to the other cells but without the test substance was defined as the 100% value. The data obtained from this test represent triple determinations and at least two experiments had been carried out independently of each other.

The IC50 values of representative embodiments of this assay are listed in table 1 as follows:

TABLE 1

| embodiment | IC$_{50}$ [nM] |
|---|---|
| 1 | 1.1 |
| 2 | 2.2 |
| 3 | 0.7 |
| 4 | 0.8 |
| 5 | 0.2 |
| 6 | 1.1 |
| 8 | 5.2 |
| 9 | 53 |
| 10 | 81 |
| 11 | 6.7 |
| 12 | 13 |
| 13 | 12.5 |
| 14 | 59 |
| 15 | 0.9 |
| 16 | 12 |
| 18 | 173 |
| 20 | 0.3 |
| 25 | 164 |
| 26 | 10 |

Monomethylauristatin F (MMAF), in comparison, demonstrates an IC50 value in this test of 260 nM.

B-2. Determination of Anti-proliferative Effects of HT-29 wt Cell Line:

A defined number of cells of the human renal carcinoma cell line 786-0 were cultured in a 96 well micro titer plate in rich medium (2500 or 7.000 cells/well) and then incubated over night at 37° C./5% CO2. After 18 hours the seed medium was replaced by a fresh medium with 10% FCS. The treatment started with measuring out the respective test substance. The dose-response curves were determined of the investigative substances with a concentration of $10^{-5}$ M to $10^{-14}$ M (1:10 dilutions). Incubation times of between 48 hours and 96 hours were chosen. The proliferation was detected by means of the MTT assay (ATCC, Manassas, Va., USA, catalogue no. 30-1010K). After completion of selected incubation period the MTT reagent was incubated with the cells for 4 hours before lysis occurred over night by measuring out the detergent. The created stain was detected at 570 nm. The proliferation of the cells, which were treated identically to the other cells but without the test substance, was defined as the 100% value. The data obtained from this test represent triple determinations and at least two experiments had been carried out independently of each other.

The IC50 values of representative embodiments of this assay are listed in table 2 as follows:

TABLE 2

| embodiment | IC$_{50}$ [nM] |
|---|---|
| 1 | 0.1 |
| 4 | 0.1 |
| 6 | 0.4 |
| 8 | 0.5 |
| 9 | 4.4 |
| 11 | 0.8 |
| 13 | 1.0 |
| 16 | 0.1 |
| 18 | 16 |
| 25 | 1.5 |
| 26 | 1.5 |
| 28 | 1.3 |

Monomethylauristatin F (MMAF), in comparison, demonstrates an IC50 value in this test of 10 nM.

B-3. Determination of Impact on Tubulin Polymerization:

Cancer cells are degenerate cells which very often also cause tumor formation by increased cell division. Microtubuli form spindle fibers of a spindle apparatus and are an essential component of the cell cycle. The coordinated composition and decomposition of microtubuli enable exact distribution of chromosomes to the daughter nuclei and form a continuous dynamic process. A disruption of this dynamic cycle leads to faulty cell division and ultimately to cell death. The increased cell division makes cancer cells also particularly susceptible to spindle fiber toxins which are an integral part of the chemotherapy. Spindle fiber toxins such as paclitaxel or epothilones lead to a highly increased speed of polymerization of microtubuli whereas vinca alkaloids or also monomethylauristatin E (MMAE) significantly reduce the speed of polymerization of microtubuli. In both cases the necessary dynamics of the cell cycle is considerably disrupted. The compounds studied in present invention lead to a reduced speed of polymerization of microtubuli.

For studying the polymerization of tubuli the fluorescence-based Microtubule Polymerization Assay Kit" of the company Cytoskeleton (Denver, Colo., USA; order number: BK011) was used. In this assay the unpolymerized tubulin GTP was added for triggering spontaneous polymerization. The assay is based on the bonding of 4',6-diamidino-2-phenylindol (DAPI) of the fluorophor to tubulin. Free and bonded DAPI can be distinguished because of the different emission spectra. Because DAPI has a significantly higher affinity to polymerized tubulin as opposed to unpolymerized tubulin, the tubulin polymerization can be observed as the fluorescence bound DAPI fluorophores increase.

In order to carry out this assay the test substances which were dissolved in DMSO were diluted in water from their initial concentration of 10 nM to 1 µM. In addition to buffer control an assay control with polymerization enhancing paclitaxel was conducted and for the other a control with polymerization inhibiting vinblastine was carried out. 96-well perforated plates with half floor space were used for measuring. The kinetics of tubulin polymerization of 1 hour duration at 37° C. were monitored with a fluorimeter. The excitation wave length was 355 nm, emission was observed at 460 nm. For the area of linear increase within the first 10 minutes the fluorescence alteration per minute (AF/min), which is the speed of polymerization of micro tubuli, was calculated. The potency of the test substances was quantified by means of the respective speed reduction of polymerization.

B-4. Determination of Plasma Stability in vitro:
Method A:

1 mg of the respective test substance was dissolved in 0.5 ml acetonitrile/MSO (9:1) 20 µl of this solution were extracted and added to 1 ml of rat plasma and human plasma respectively which were heated to 37° C. (plasma of male wistar rats with li-heparin, Fa. Harlan & Winkelmann, and human leukocyte-depleted fresh plasma from whole blood draw respectively). From this plasma solution which had been shaken well an aliquot of 100 µl was extracted immediately after adding the sample (basic value as reference value) and then 100 µl aliquot each after 5, 10, 30, 60, 120, 180, and 240 minutes and, if needed, after 24 hours, and added to 300 µl of acetonitrile. The precipitated plasma proteins were centrifuged for 10 minutes at 5000 rpm and 30 µl of the supernatant were analyzed with respect to concentration of unaltered test substance by means of HPLC. Quantification was done by way of area percent of the individual peaks.

HPLC Method for Rat Plasma:

Instrument: Agilent 1200 with DAD, binary pump, auto sampler, column oven, and thermostat, column: Kromasil 100 C18, 250 mm×4 mm, 5 µm; column temperature: 45° C.; Eluent A: 5 ml perchloric acid/L water, Eluent B: acetonitrile; gradient: 0-8 min 98% A, 2% B; 8-15 min 56% A, 44% B; 15-20 min 10% A, 90% B; 20-21 min 10% A, 90% B; 21-23 min 98% A, 2% B; 23-25 min 98% A, 2% B; flow rate: 2 ml/min; UV detection: 220 nm.

HPLC Method for Human Plasma:

Instrument: Agilent 1100 with DAD, binary pump, auto sampler, column oven, and thermostat, column: Kromasil 100 C18, 250 mm×4 mm, 5 µm; column temperature: 45° C.; Eluent A: 5 ml perchloric acid/L water, Eluent B: acetonitrile; gradient: 0-3 min 98% A, 2% B; 3-10 min 65% A, 35% B; 10-15 min 40% A, 60% B; 15-21 min 10% A, 90% B; 21-22 min 10% A, 90% B; 22-24 min 98% A, 2% B; 24-26 min 98% A, 2% B; flow rate: 2 ml/min; UV detection: 220 nm.

Method B:

The corresponding test substance was incubated in rat plasma and human plasma respectively at 37° C. while lightly stirring it for 5 hours. At various points in time (0, 2, 5, 10, 20, 30, 60, 120, 180, and 300 minutes) 100 µl aliquot were extracted. Following addition of internal standard (10 µl), the proteins were precipitated by adding 200 µl of acetonitrile and the compound was centrifuged with a laboratory centrifuge for 5 minutes. After adding a buffer solution of 150 µl of ammonium acetate pH 3 to 150 µl of the supernatant the concentration of unaltered test substance was analyzed by means of LC/MSMS.

B-5. Determination of Cell Permeability:

The cell permeability of a substance can be analyzed by means of in vitro tests in a flux assay using Caco-2-cells [M. D. Troutman and D. R. Thakker, Pharm. Res. 20 (8), 1210-1224 (2003)]. For this analysis the cells were cultured on 24 membrane filter plates for 15 to 16 days. In order to determine permeation the test substance in question was given either apical (A) to a HEPES buffer or basal (B) on the cells and incubated for 2 hours. The samples were withdrawn after 0 and 2 hours from the cis and trans compartments. The samples were separated by means of HPLC (Agilent 1200, Böblingen, Germany) using reverse-phase columns. The HPLC system was coupled to a triple quadropol mass spectrometer API 4000 (Applied Biosystems Applera, Darmstadt, Germany) via a turbo ion spray. The permeability was evaluated by means of the $P_{app}$ value which was calculated with the help of the formula published by Schwab et al. [D. Schwab et al., J. Med. Chem. 46, 1716-1725 (2003)]. A substance was classified as active if the ratio of $P_{app}$ (B-a) to $P_{app}$ (A-B) was >2 or <0.5.

The permeability from B to A [$P_{app}^{(B-A)}$] is particularly important for toxophores which are being released intracellular: The lower the permeability the longer the residence time of the substance in the cell after intracellular release and, consequently, the more time available for interaction with the biochemical target (here: tubulin).

The permeability data of representative embodiments of this assay are listed in table 3 as follows:

TABLE 3

| embodiment | $P_{app}$ (B-A) [nm/s] |
|---|---|
| 7 | 18 |
| 8 | 22 |
| 11 | 11 |
| 12 | 15 |
| 13 | 10 |
| 14 | 3 |
| 17 | 2 |
| 18 | 2 |
| 19 | 2 |
| 23 | 2 |

In comparison monomethylauristatin E (MMAE) and monomethylauristatin F (MMAF) demonstrate in this test a $P_{app}$ (B-A)-value of 89 nm/s and 73 nm/s respectively.

B-6. Determination of Substrate Characteristics for P-Glycoprotein (P-gp (P-gp):

Many tumor cells express transport proteins for drugs, often involving the development of resistance to cytostatica. Substances which are no substrates of such transport proteins, as for instance P-glycoprotein (P-gp) or BCRP, could therefore exhibit an improved efficacy.

The substrate characteristics of a substance for P-gp (ABCB1) were determined by means of a flux assay, using LLC-PK$_1$ cells which over express P-gp (L-MDR$_1$ cells) [A. H. Schinkel et al., J. Clin. Invest. 96, 1698-1705 (1995)]. For this analysis LLC-PK1 or LMDR1 cells were cultured on 96 membrane filter plates for 3 to 4 days. In order to determine the permeation the appropriate test substance alone or in the presence of an inhibitor (such as for example ivermectin or verpamil) was added to a HEPES buffer solution on the cells either apical (A) or basal (B) and incubated for 2 hours. The samples were withdrawn after 0 hour and 2 hours from the cis and trans compartments. The samples were separated by means of HPLC, using reverse phase columns. The HPLC system was coupled to a triple quadropol mass spectrometer API 3000 (Applied Biosystems Applera, Darmstadt, Germany) via a turbo ion spray. The permeability was evaluated by means of the $P_{app}$ value which was calculated with the help of the formula published by Schwab et al. [D. Schwab et al., J. Med. Chem. 46, 1716-1725 (2003)]. A substance was classified as active if the ratio of $P_{app}$(B-A) and $P_{app}$(A-B) was >2.

Further criteria for evaluation of P-gp substrate characteristics can be the comparison of the efflux ratios in L-MDR1- and LLC-PK1 cells or comparison of the efflux ratio of presence or absence of an inhibitor. If the values differ by more than factor 2, then the substance in question is a Pgp substrate.

C. Embodiments of Pharmaceutical Compounds

The inventive compounds can be translated as follows:
Tablets:
Composition:
100 mg of compound according to invention, 50 mg of lactose (monohydrate), 50 mg of corn starch (native), 10 mg of polyvinylpyrrolidone (PVP 25) (Fa. BASF, Ludwigshafen, Germany), and 2 mg of magnesium stearate.

Tablet weight 212 mg, diameter 8 mm, curved radius 12 mm.
Production:
The composition consisting of the compound according to invention, lactose, and starch will be granulated with a 5% solution (m/m) of PVPs in water. After drying, the granulate material will be mixed with magnesium stearate for 5 minutes. The mixture will be compressed with a conventional tablet press (in the form of a tablet as described before). A pressing force 15 kN will be used as indicative value for the compression.
Oral Suspensions:
Composition:
1000 mg of the compound according to invention, 1000 mg of ethanol (96%), 400 mg of Rhodigel® (Xanthan gum from the company FMC, Pennsylvania, USA), and 99 g of water.

A single dose of 100 mg of the compound according to invention corresponds with 10 ml of oral suspension.
Production:
The Rhodigel will be suspended in ethanol, the compound according to invention will be added to the suspension. Water will be added while stirring. Stirring will be continued for approximately 6 hours until maceration of the Rhodigel is completed.
Oral Solution:
Composition:
500 mg of the compound according to invention, 2.5 g of polysorbate, and 97 g of polyethylene glycol 400. A single dose of 100 mg of the compound according to invention corresponds with 20 g of oral suspension.
Production:
The compound according to invention will be stirred into a composition of polyethylene glycol and polysorbate. Stirring continues until the compound according to invention is completely dissolved.
IV Solution:
The compound according to invention will be dissolved in a concentrate below saturation solubility in a physiologically tolerable solvent (e.g. isotonic saline solution, glucose solution 5% and/or PEG 400 solution 30%). The solution will be filtered and then filled into aseptic and pyro-gene free injection containers.

The invention claimed is:
1. A compound of formula (I)

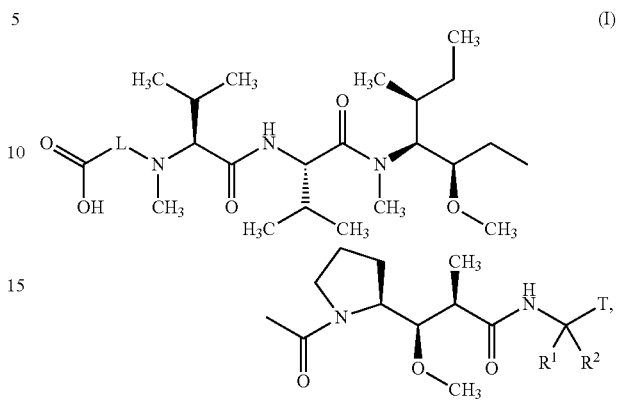

or a salt or solvate thereof, wherein
L is a straight-chain ($C_1$-$C_{12}$)-alkandiyl, optionally substituted with methyl up to four times and in which (a) two carbon atoms is optionally connected to each other in 1,2-, 1,3-, or 1,4 relation, if necessary including carbon atoms that are located between them to form a ($C_3$-$C_6$)-cycloalkyl-ring or a phenyl ring or (b) up to three $CH_2$ groups not adjacent to each other are optionally substituted for an O,
$R^1$ is hydrogen or methyl,
$R^2$ is isopropyl, isobutyl, sec.-butyl, tert.-butyl, 1-hydroxyethyl, phenyl, benzyl, 4-hydroxybenzyl, 1-phenylethyl, diphenylmethyl, 1H-imidazol-4-ylmethyl, or 1H-indol-3-ylmethyl,
or
$R^1$ and $R^2$, together with the carbon atom to which they are both connected, form a 2-phenylcyclopropan-1,1-diyl group of the formula

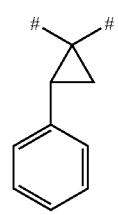

wherein
marks the points of attachment with other parts of the molecule,
and
T is a group with formula —C(=O)—$OR^3$, —C(=O)—$NR^4R^5$, —C(=O)—NH—NH—$R^6$, or —$CH_2$—O—$R^7$ in which
$R^3$ is hydrogen, ($C_1$-$C_6$)-alkyl or ($C_3$-$C_{10}$)-cycloalkyl, wherein ($C_1$-$C_6$)-alkyl is optionally substituted with phenyl, naphthyl, or ($C_3$-$C_{10}$)-cycloalkyl,
$R^4$ is hydrogen or ($C_1$-$C_6$)-alkyl,
$R^5$ is hydrogen, ($C_1$-$C_6$)-alkyl, or ($C_3$-$C_{10}$)-cycloalkyl, wherein ($C_1$-$C_6$)-alkyl is optionally substituted with phenyl,
or
$R^4$ and $R^5$ are connected to each other and, together with the nitrogen atom they are attached to, form a 5- to 7-membered, saturated aza-heterocyclic compound, which may optionally contain a further ring-heteroatom selected from the group consisting of >N—H, >N—CH$_3$, or —O—; and wherein said further ring-heteroatom is located either at the 1,3- or 1,4-location in relation to the aforementioned nitrogen atom, $R^6$ is (C$_1$-C$_6$)-alkyl, (C$_1$-C$_6$)-alkylcarbonyl, phenyl, or benzoyl, and $R^7$ is (C$_1$-C$_6$)-alkyl, optionally substituted with phenyl, where phenyl is optionally substituted with (C$_1$-C$_6$)-alkoxycarbonyl or carboxyl.

2. The compound of claim 1 or a salt or solvate thereof, wherein

L is a straight-chain (C$_1$-C$_8$)-alkandiyl, in which (a) two carbon atoms are optionally linked to each other in 1,3 or 1,4 relation including one or two carbon atoms located between them to form a phenyl ring or (b) up to two CH$_2$ groups not adjacent to each other which is optionally substituted for an O, $R^1$ is hydrogen, $R^2$ is benzyl, 4-hydroxybenzyl, 1-phenylethyl, or 1H-indol-3-ylmethyl, or $R^1$ and $R^2$, together with the carbon atom to which they are both connected, form a 2-phenylcyclopropan-1,1-diyl group of the formula

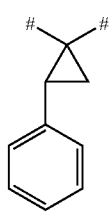

wherein marks the points of attachment with other parts of the molecule, and

T is a group with formula —C(=O)—OR$^3$, —C(=O)—NR$^4$R$^5$, —C(=O)—NH—NH—R$^6$, or —CH$_2$—O—R$^7$ in which $R^3$ is hydrogen or (C$_1$-C$_4$)-alkyl, which is optionally substituted with phenyl, naphthyl, or (C$_3$-C$_{10}$)-cycloalkyl, $R^4$ is hydrogen or methyl, $R^5$ is hydrogen or (C$_1$-C$_4$)-alkyl, which is optionally substituted with phenyl, or $R^4$ and $R^5$ are connected to each other and together with the nitrogen atom they are attached to, form a piperidine- or morpholine ring, $R^6$ is (C$_1$-C$_4$)-alkylcarbonyl or benzoyl, and $R^7$ is (C$_1$-C$_4$)-alkyl or benzyl, which, in the phenyl group, is optionally substituted with (C$_1$-C$_4$)-alkoxycarbonyl or carboxyl.

3. The compound of claim 1 or a salt or solvate thereof, wherein

L is a straight-chain (C$_1$-C$_6$)-alkandiyl, $R^1$ is hydrogen, $R^2$ is benzyl, 1-phenylethyl or 1-H-indol-3-ylmethyl, or $R^1$ and $R^2$, together with the carbon atom they are both attached to, form a (1S,2R)-2-phenylcyclopropan-1,1-diyl group of the formula

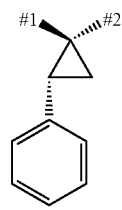

wherein

1 marks the point of attachment with the adjacent nitrogen atom and

2 marks the point of attachment of group T, and

T is a group with formula —C(=O)—OR$^3$, —C(=O)—NR$^4$R$^5$, —C(=O)—NH—NH—R$^6$, or —CH$_2$—O—R$^7$ in which $R^3$ is hydrogen, methyl, ethyl, n-propyl, benzyl, or adamantylmethyl, $R^4$ is hydrogen or methyl, $R^5$ is hydrogen, methyl, ethyl, n-propyl, or benzyl, $R^6$ is benzoyl, and $R^7$ is benzyl, which is optionally substituted with methoxycarbonyl or carboxyl in the phenyl group.

4. The compound of claim 1 or a salt or solvate thereof, wherein said compound has the formula (IA)

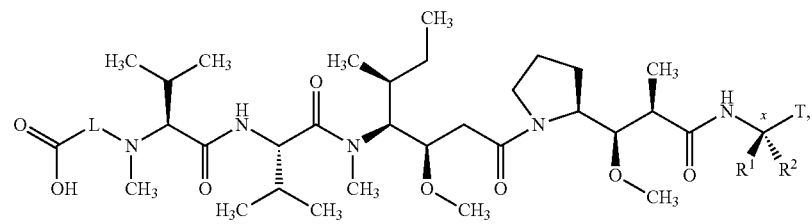

(I-A)

wherein L, $R^1$, $R^2$, and T have the meaning indicated in claim 1, and the radicals $R^1$ and $R^2$ supporting $C^X$-carbon atom has the pictured configuration.

5. A method for producing the compound of claim 1, the method comprising providing a compound of formula (II)

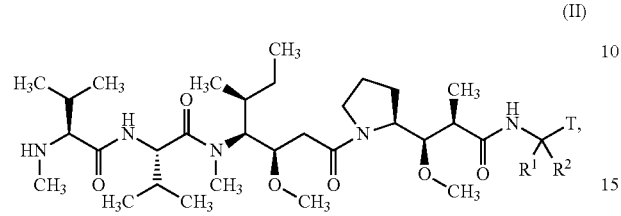

(II)

wherein $R^1$, $R^2$, and T have the meaning indicated in claim 1;

and coupling in an inert solvent the compound of formula (II) either by
[A] base-induced alkylation with a compound of formula (III)

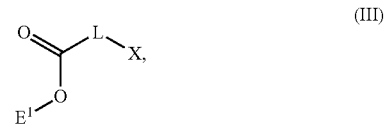

(III)

wherein
L has the meaning indicated in claim 1,
$E^1$ is hydrogen, $(C_1-C_4)$-alkyl, or benzyl,
and
X is a leaving group selected from the group consisting of chloride, bromide, iodide, mesylate, triflate, and tosylate,
to produce a compound of formula (IV)

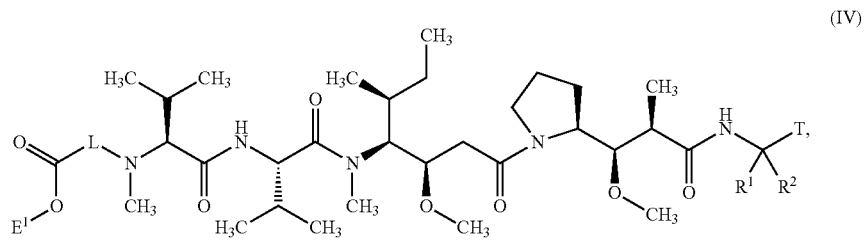

(IV)

wherein $E^1$, L, $R^1$, $R^2$, and T are defined as above,
and wherein, should $E^1$ stand for $(C_1-C_4)$-alkyl or benzyl, the ester radical is removed, thereby producing a hydrogen at $E^1$ in (III), thus producing the carboxylic acid according to formula (I);
or
[B] treatment with a compound of formula (V)

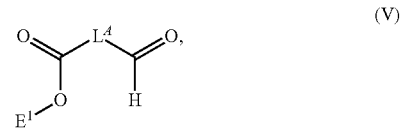

(V)

wherein
$E^1$ is hydrogen, $(C_1-C_4)$-alkyl, or benzyl,
and
$L^A$ has the meaning indicated in claim 1, however, with the alkyl chain-length shortened by one $CH_2$-unit,
in the presence of a suitable reducing agent to produce a compound of formula (VI)

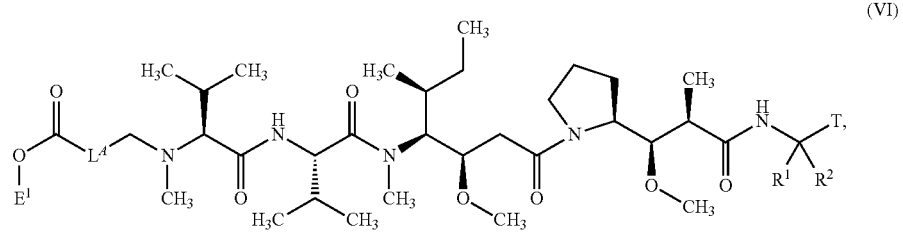

(VI)

wherein $E^1$, $L^4$, $R^1$, $R^2$, and T are defined as above, and wherein, should $E^1$ stand for $(C_1$-$C_4)$-alkyl or benzyl, the ester radical is removed, thereby producing a hydrogen at $E^1$, thus producing the carboxylic acid of formula (I-B);

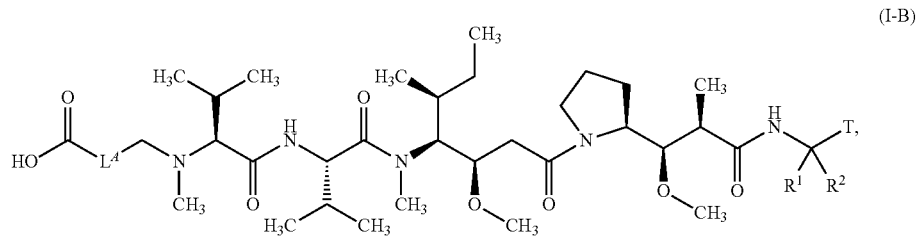

(I-B)

in which $L^4$, $R^1$, $R^2$, and T are defined as above.

6. A pharmaceutical composition comprising a compound as defined in claim 1, and further comprising one or more inert, non-toxic, pharmaceutically suitable agents.

7. The pharmaceutical composition of claim 6, further comprising one or more additional cytostatic or cytotoxic agents.

8. A method for treatment of cancer or tumor diseases in humans or animals, said method comprising administering to a subject an effective amount of at least one compound of claim 1.

9. A method for treatment of cancer or tumor diseases in humans or animals, said method comprising administering to a subject an effective amount of at least one pharmaceutical composition of claim 6.

10. The compound of claim 1, wherein said compound is selected from the group consisting of:

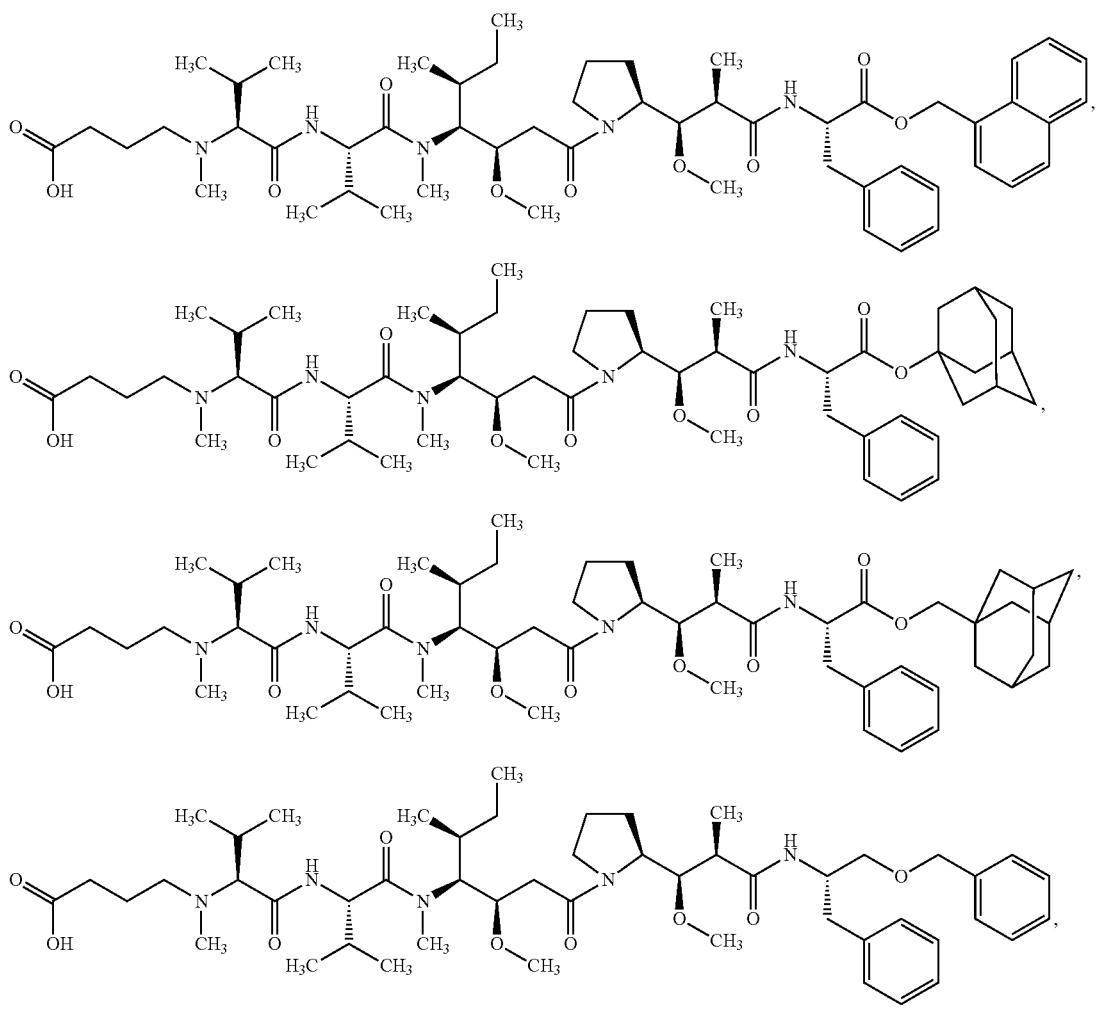

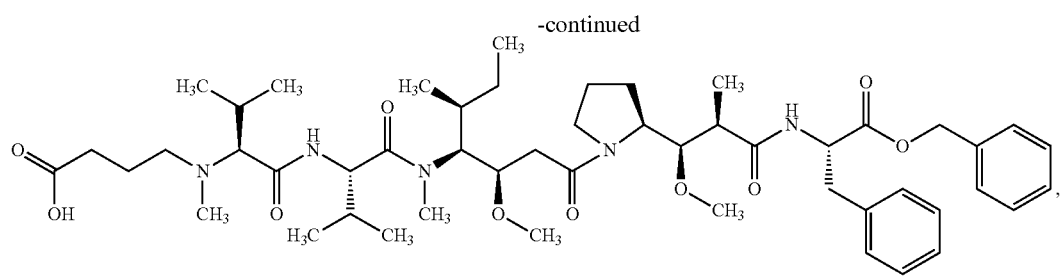,
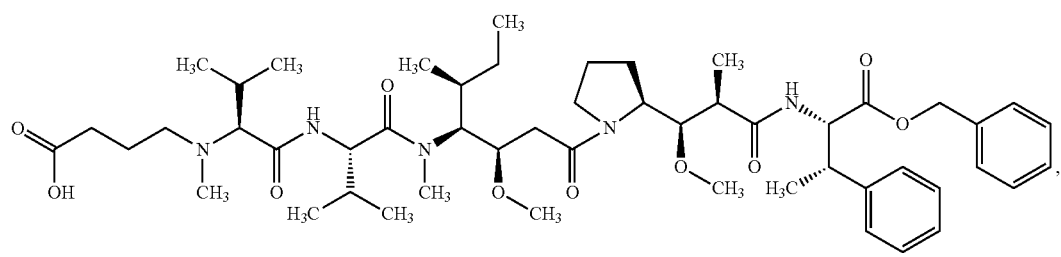,
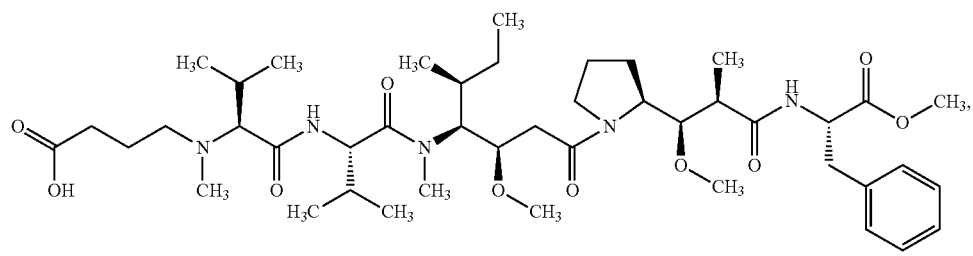,
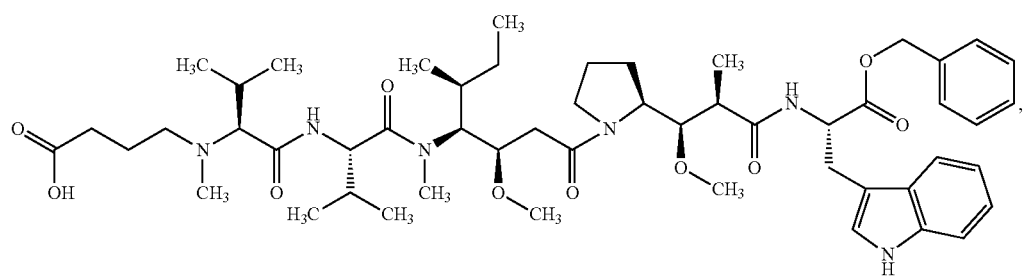,
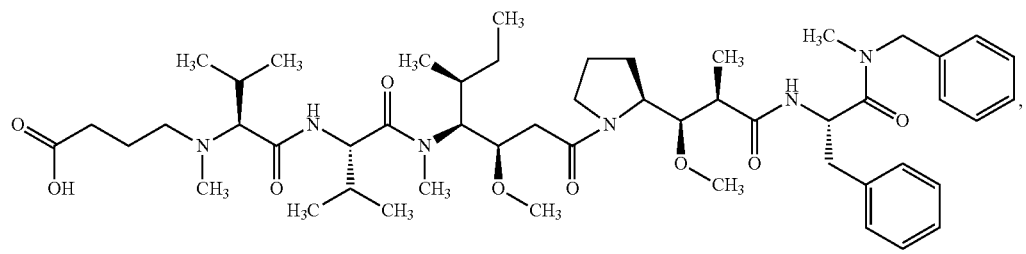,
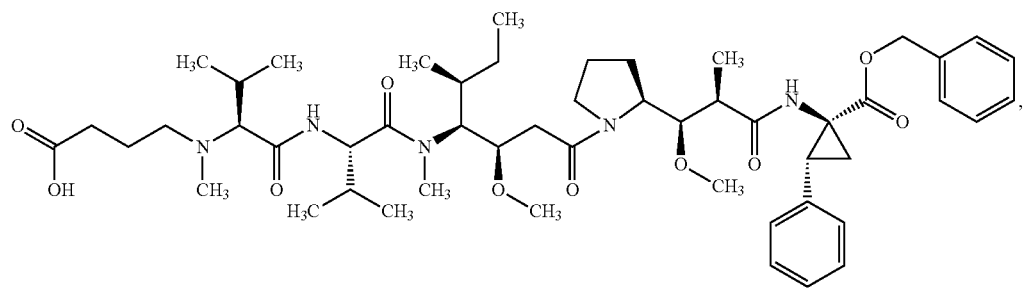,

-continued
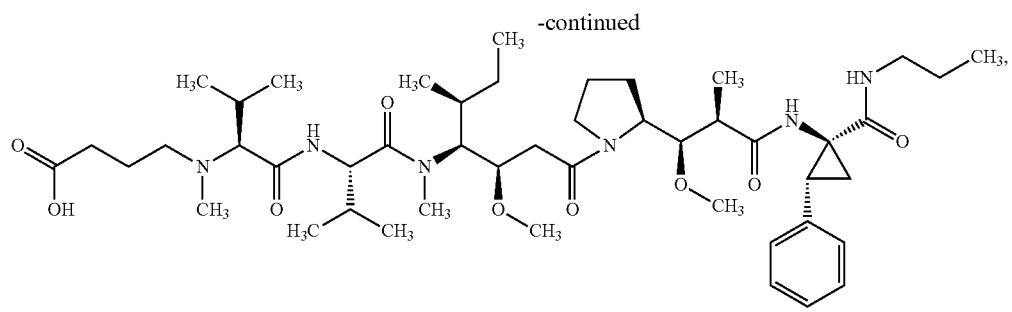
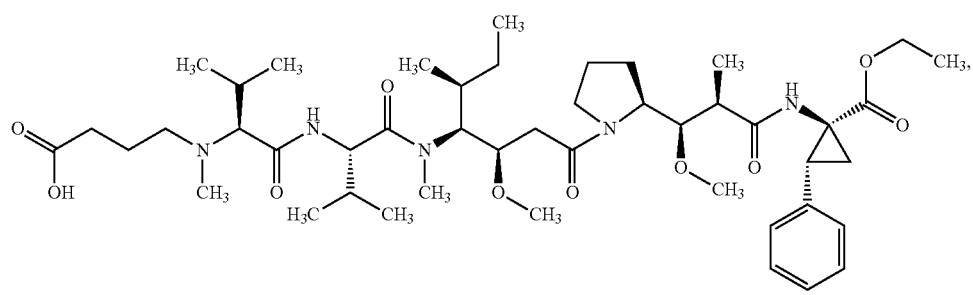
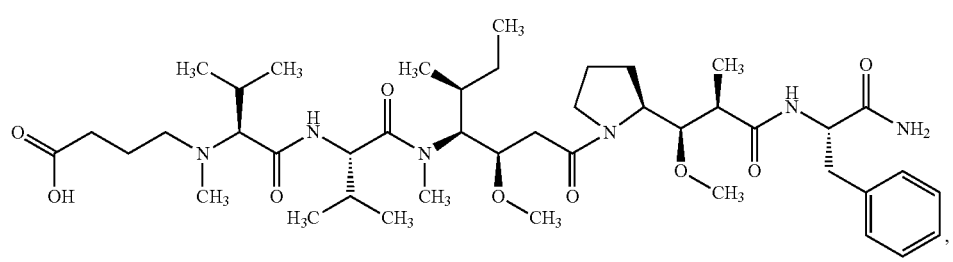
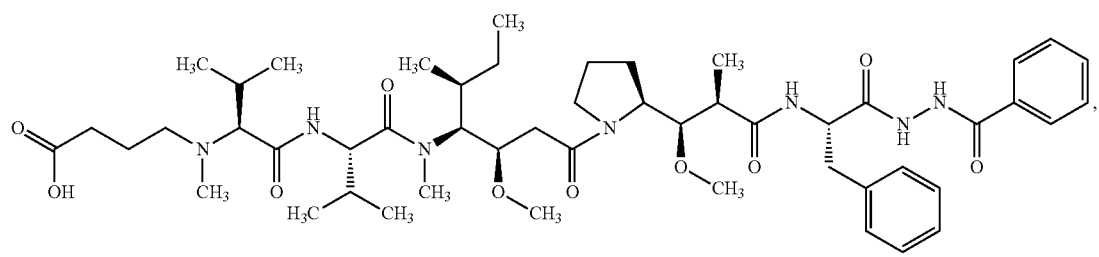
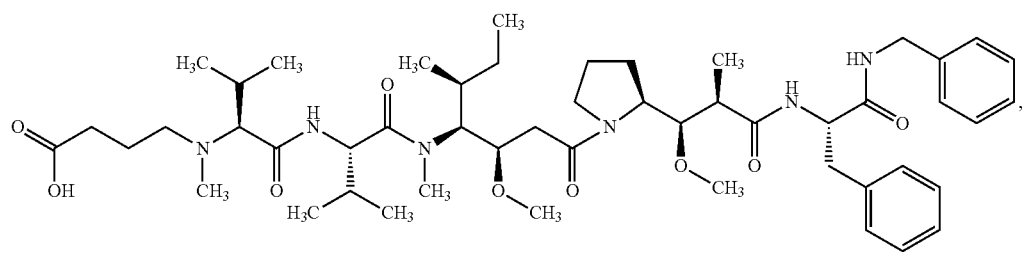
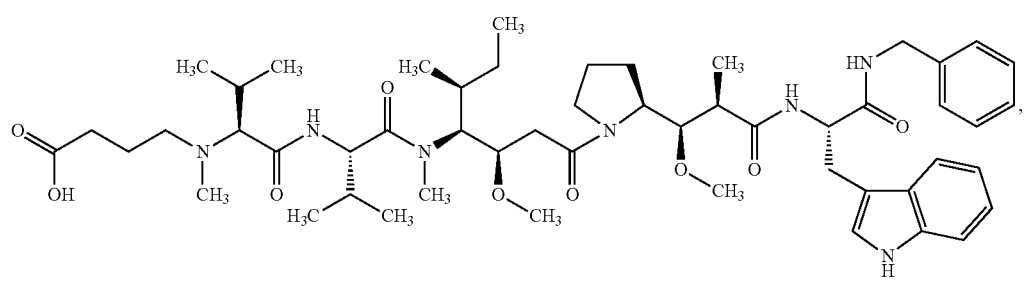

-continued
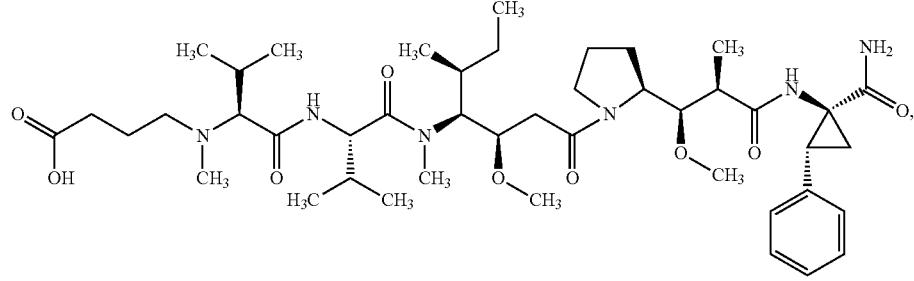
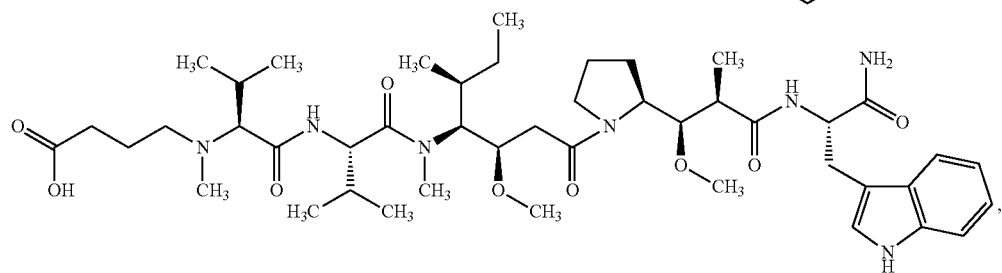
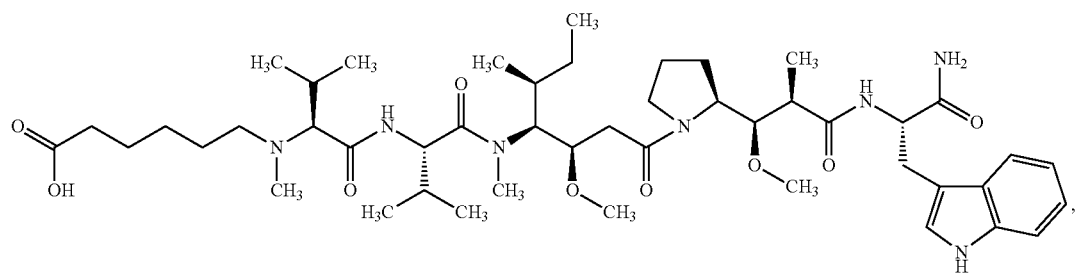
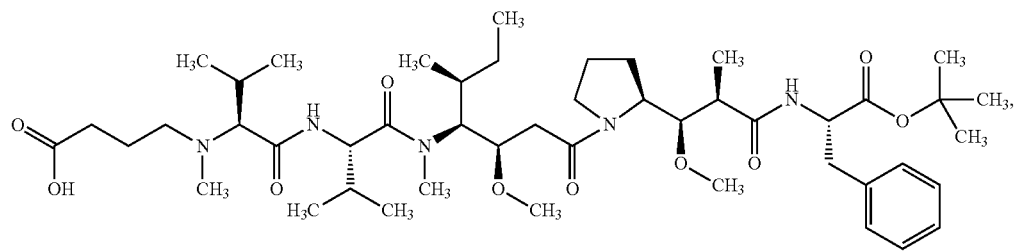
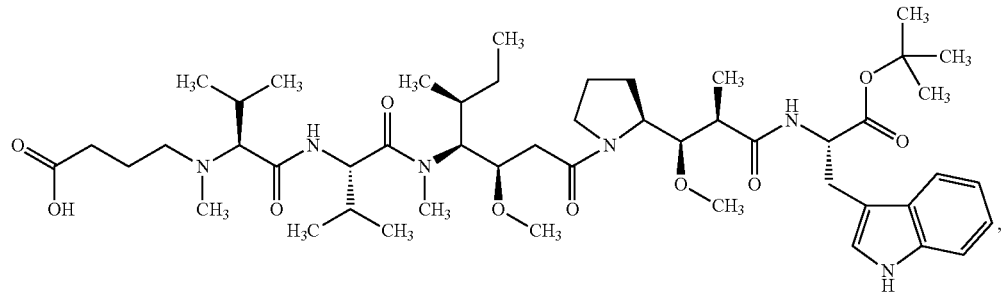
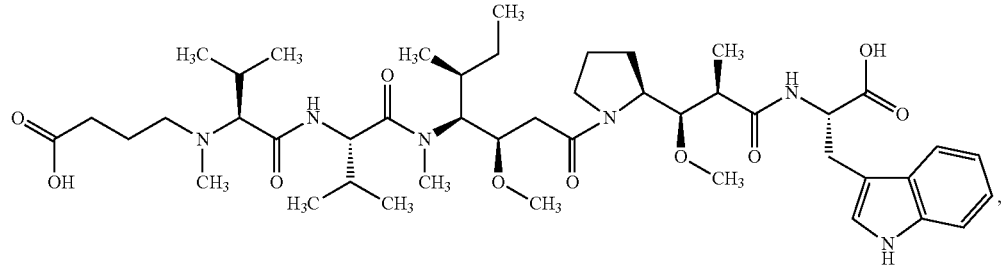

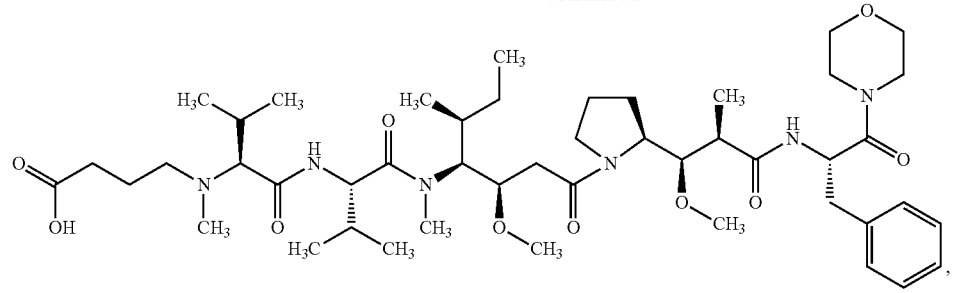
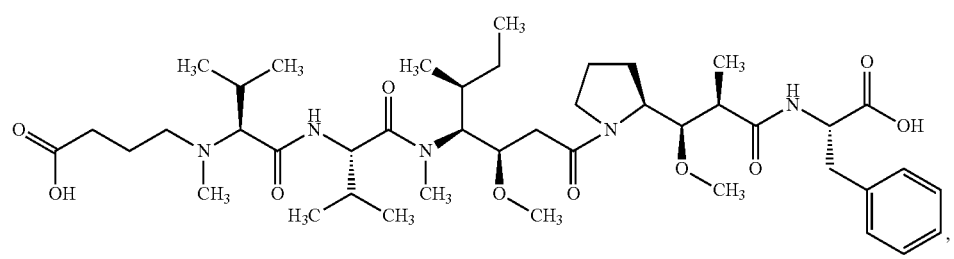
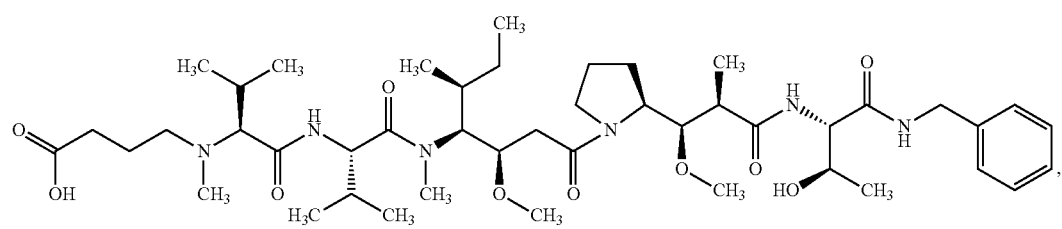
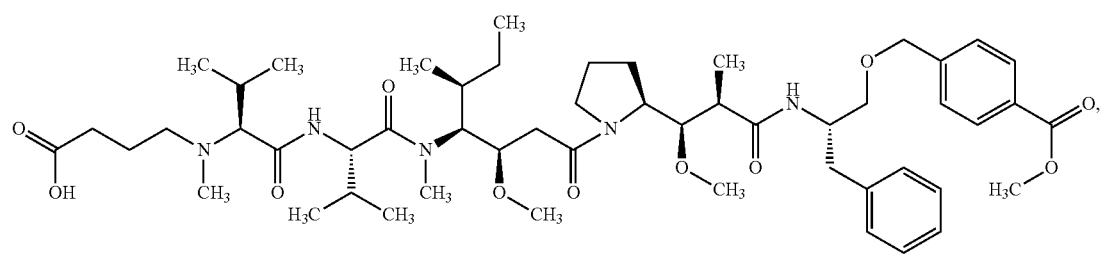
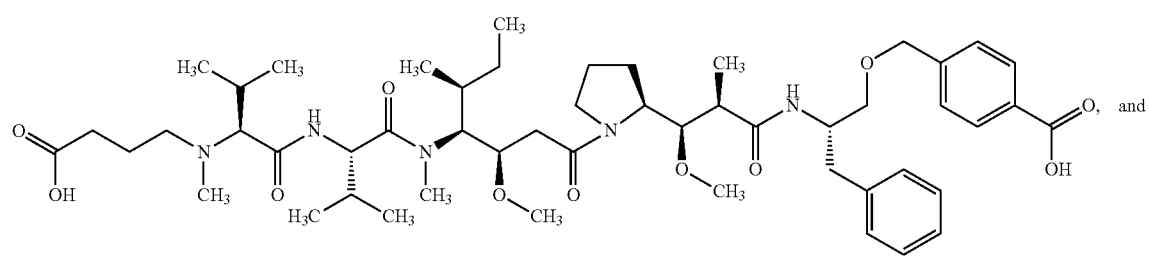

-continued
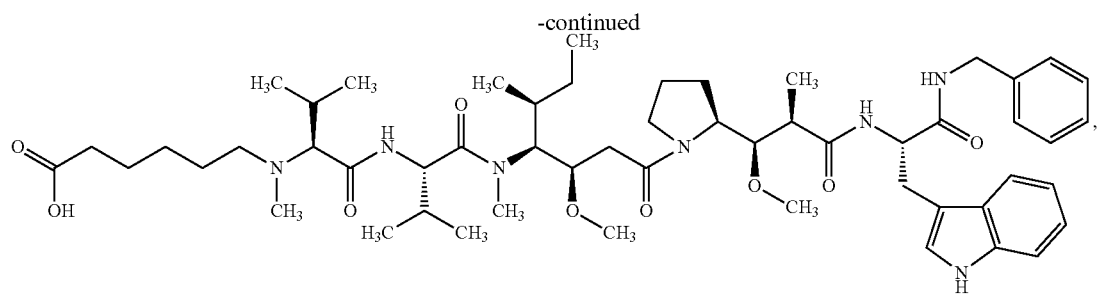
or a salt or solvate thereof.
11. The compound of claim 10, wherein said compound is selected from the group consisting of:
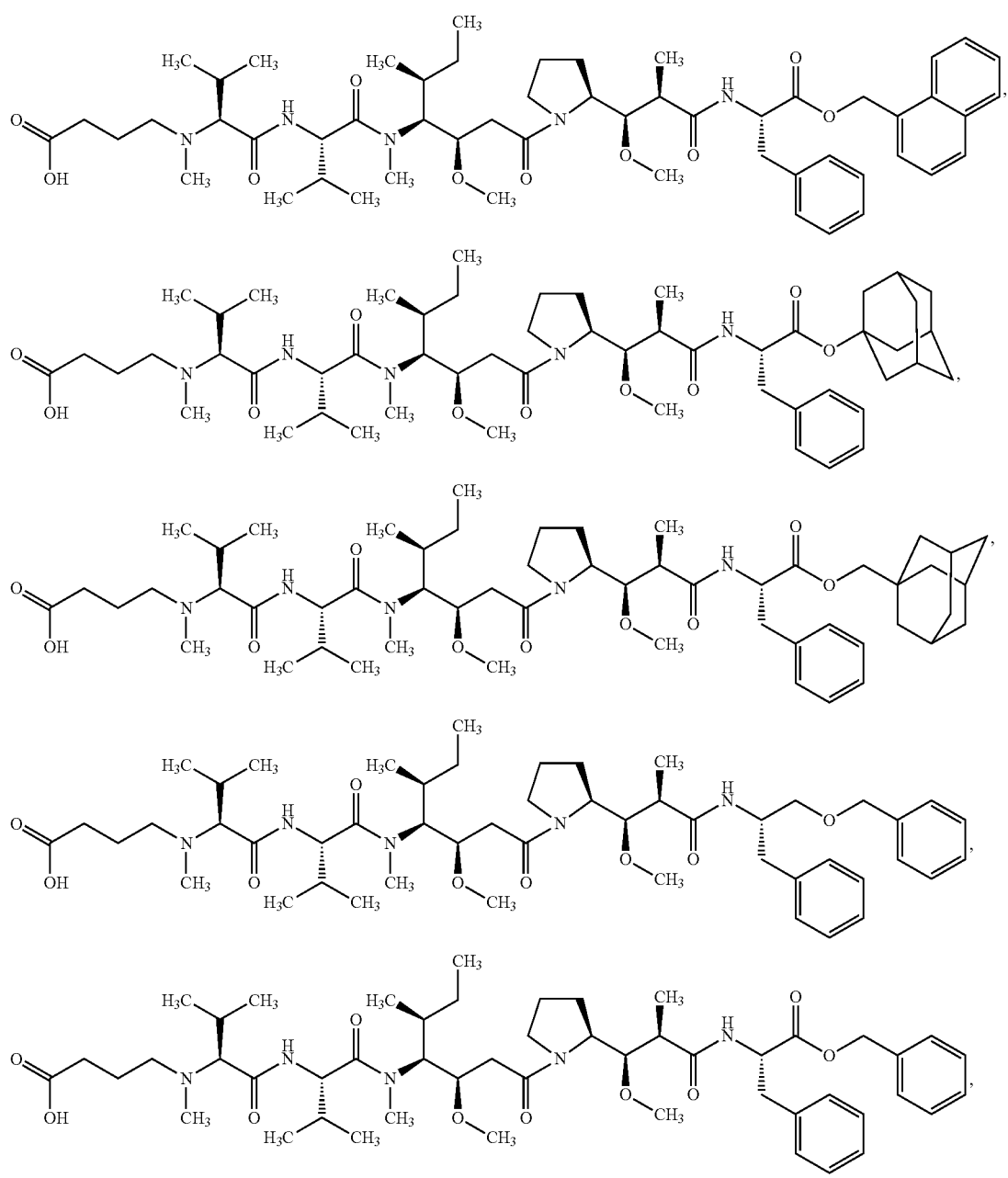

-continued
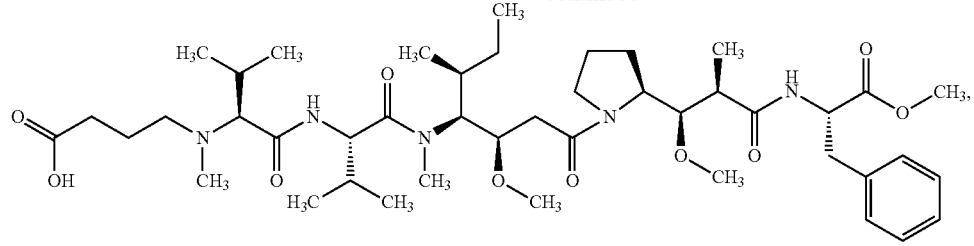
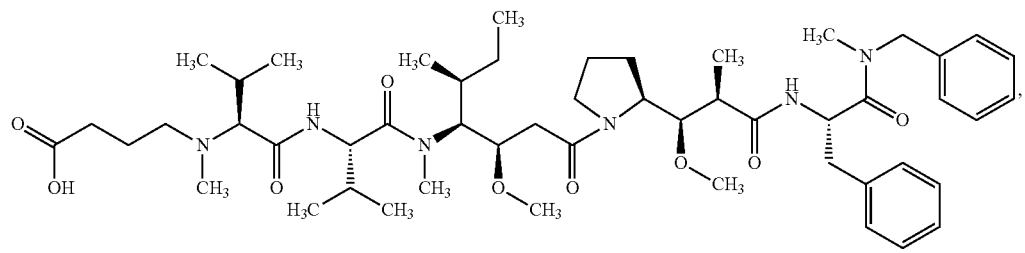
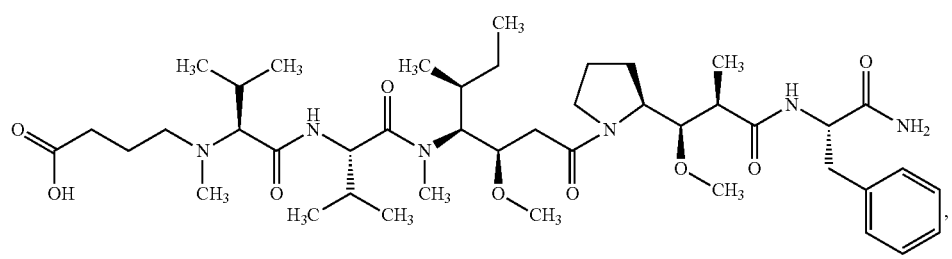
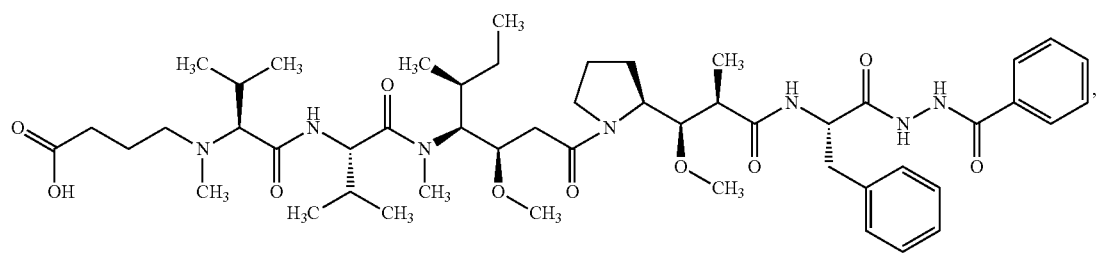
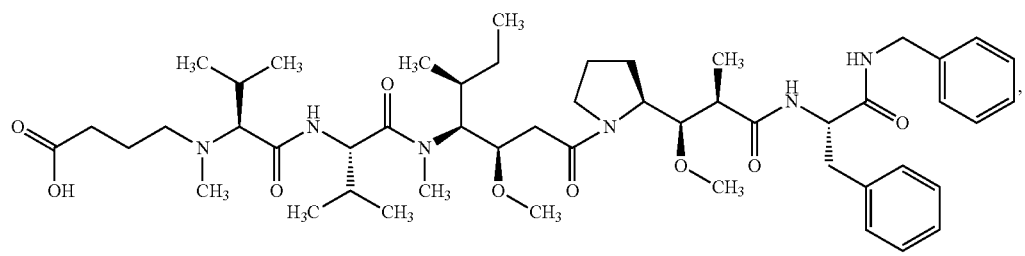
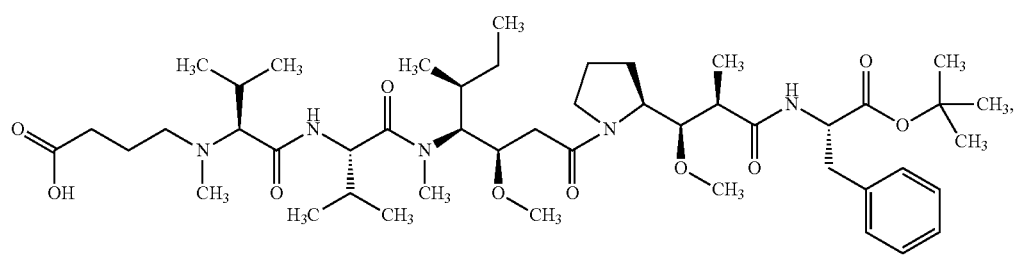

-continued
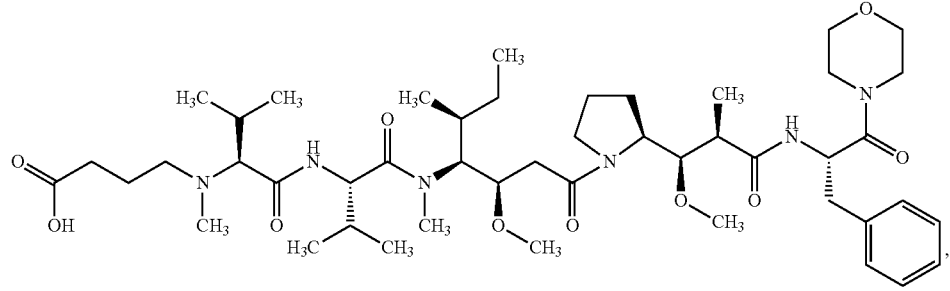
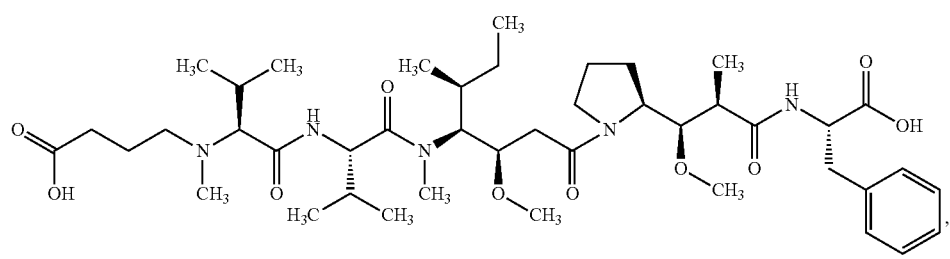
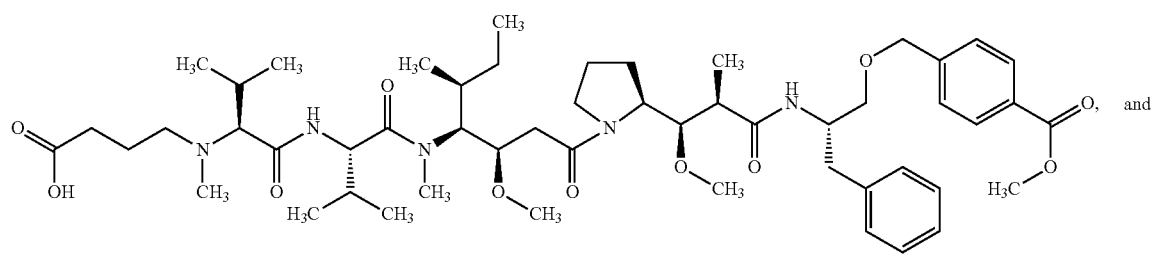
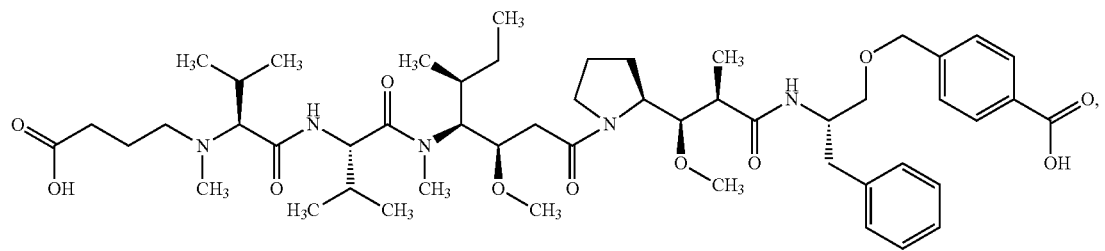
or a salt or solvate thereof.
12. The compound of claim 10, wherein said compound is selected from the group consisting of:
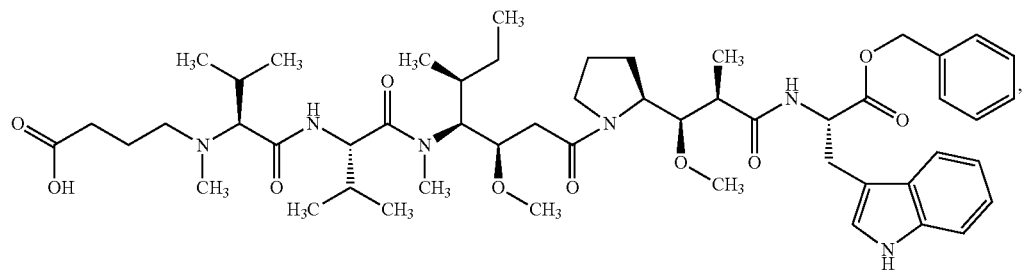

-continued
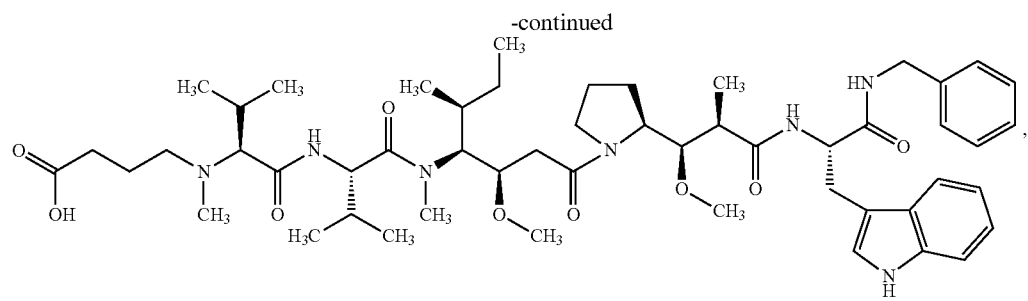
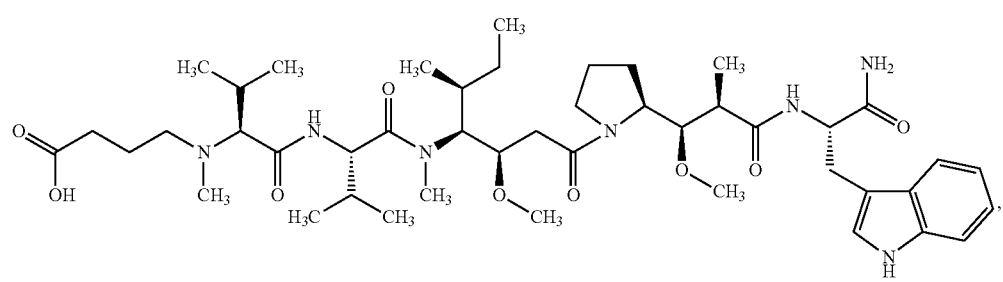
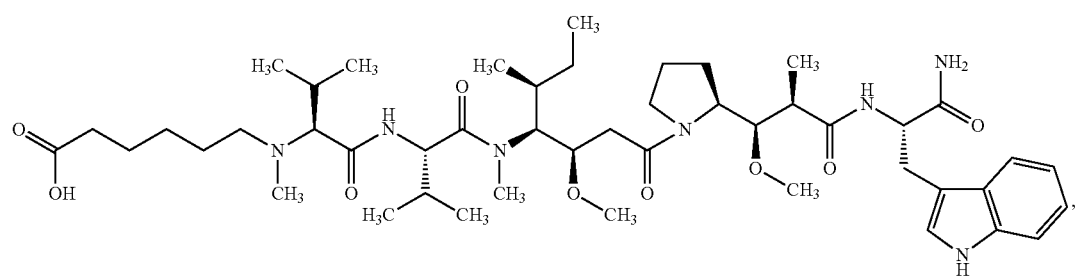
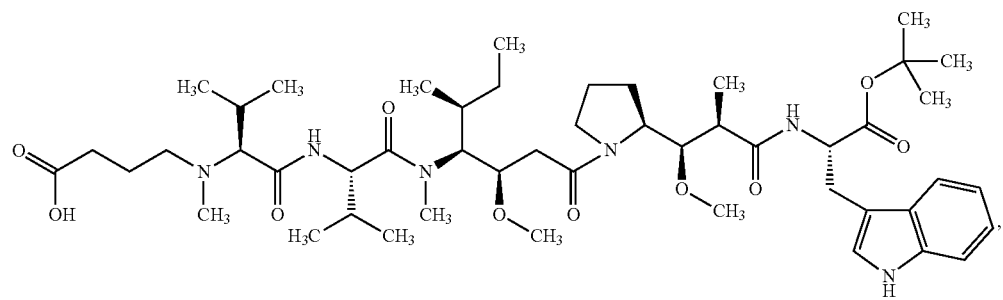
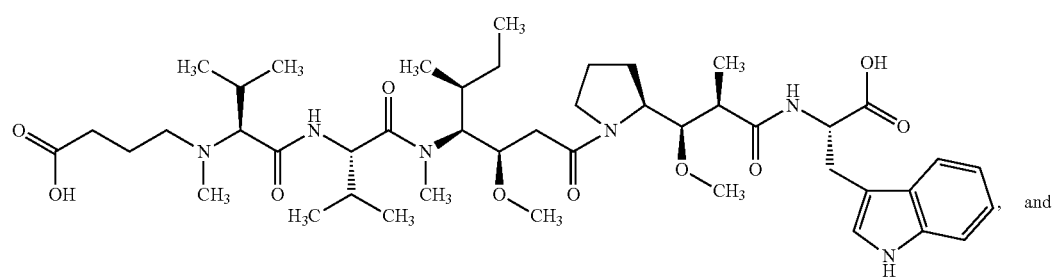, and

-continued
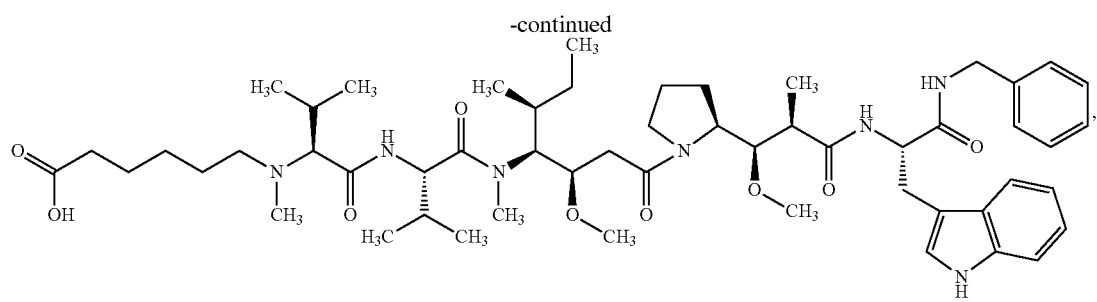
or a salt or solvate thereof.
13. The compound of claim 10, wherein said compound is selected from the group consisting of:
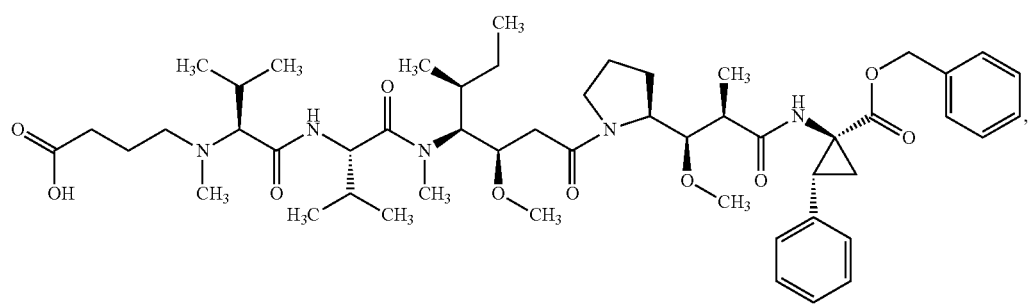
,
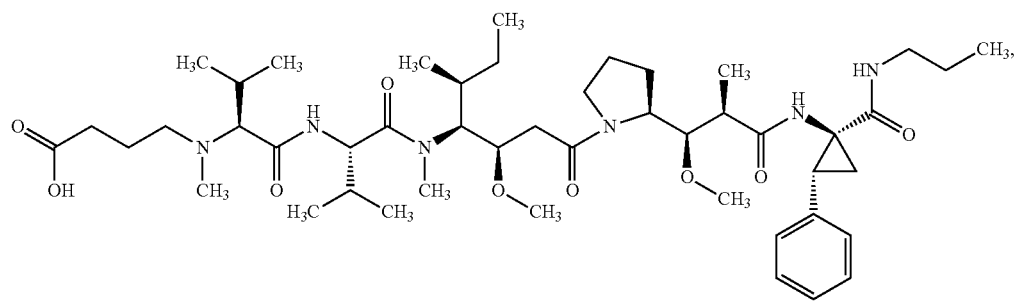
,
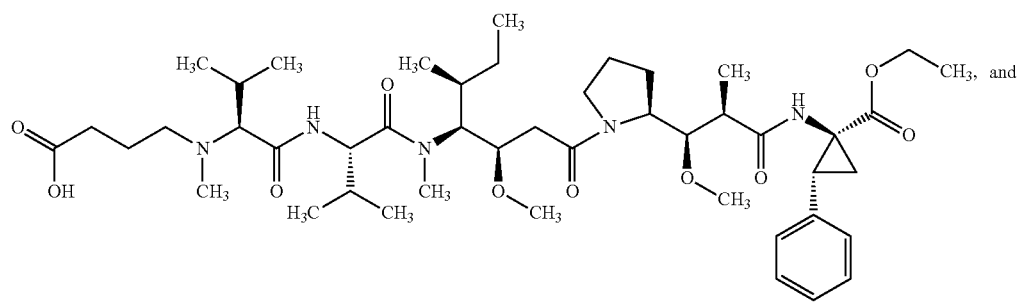
and -continued
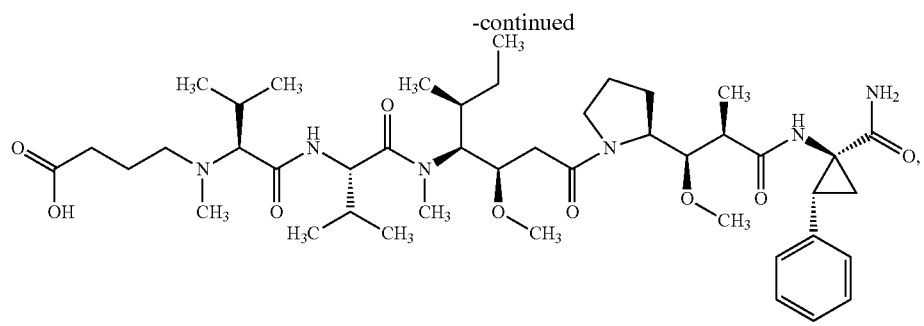
or a salt or solvate thereof.
14. The compound of claim 10, wherein said compound is selected from the group consisting of:
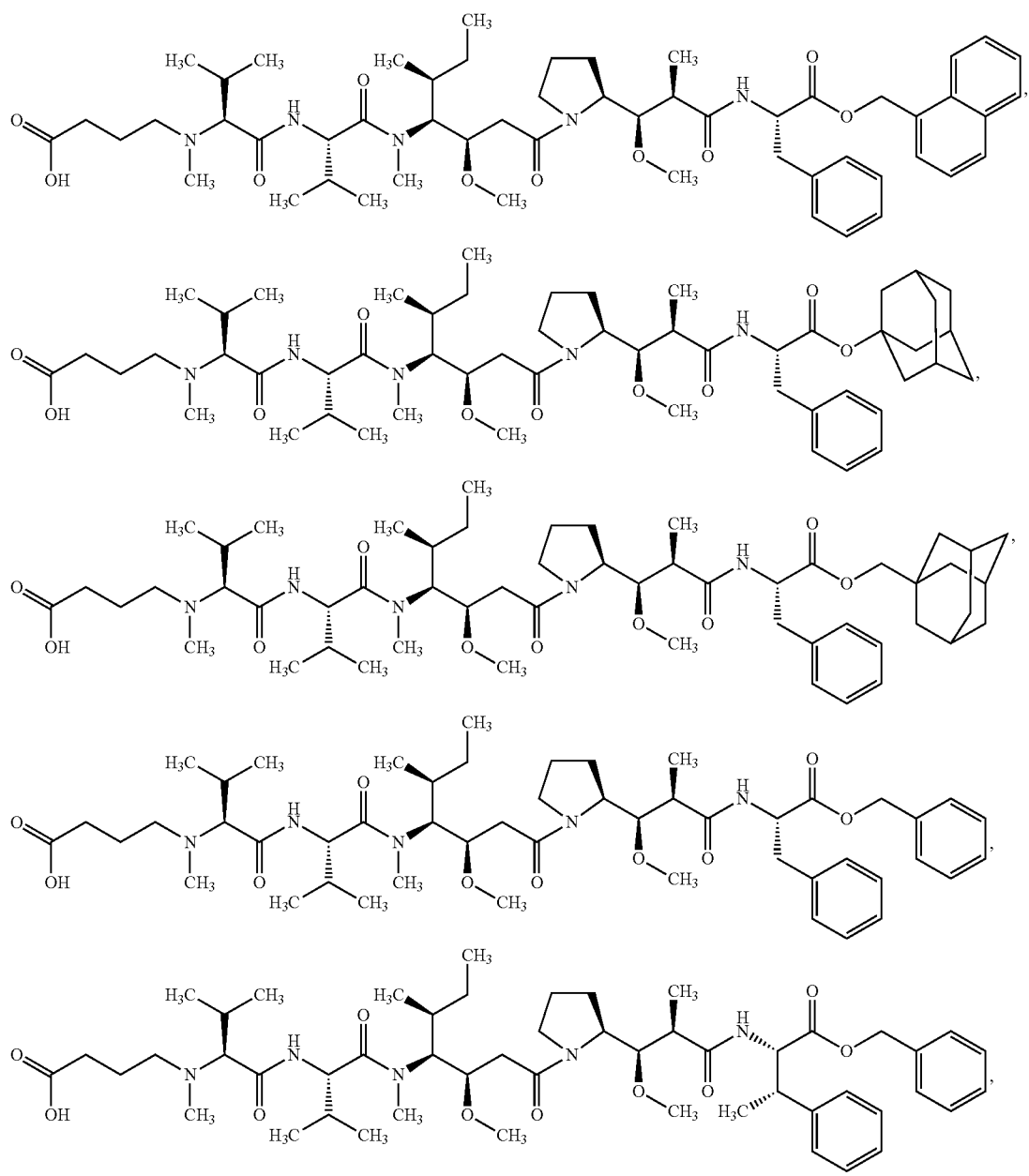

-continued
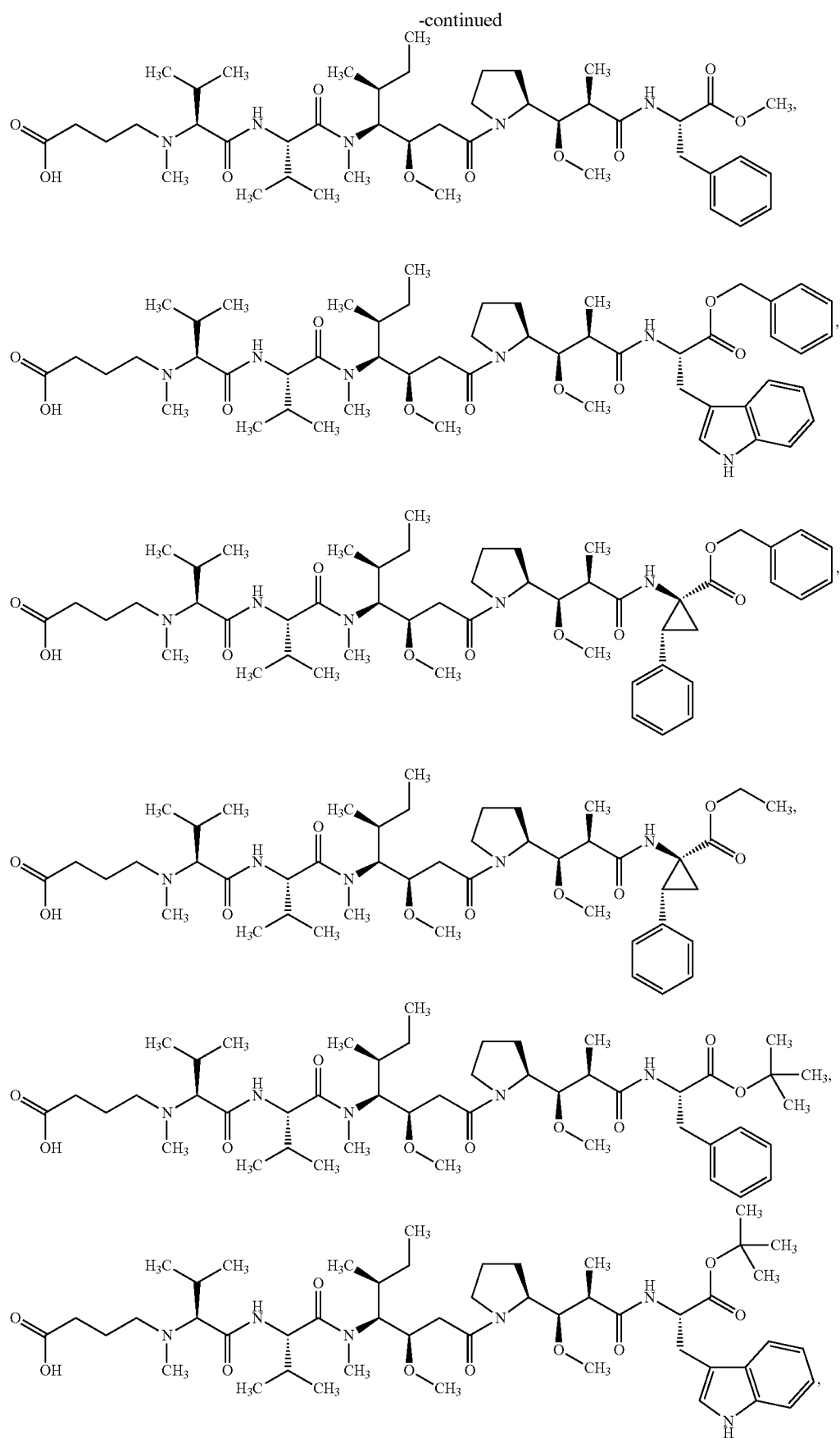

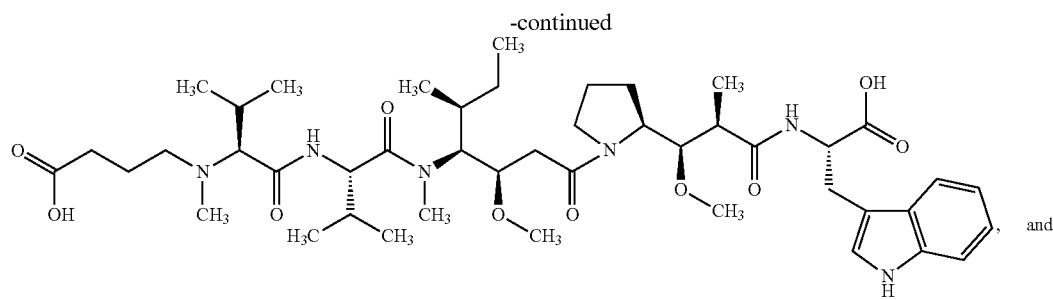
, and
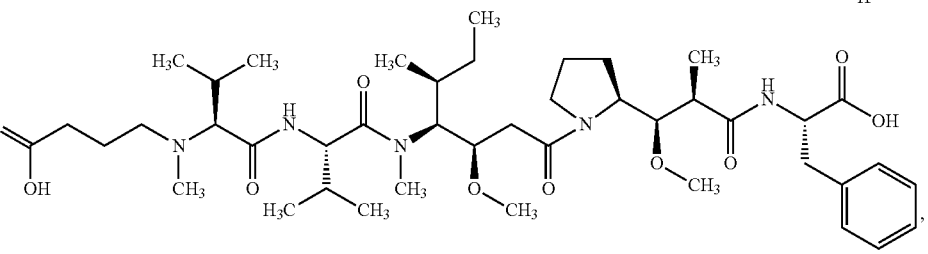
,
or a salt or solvate thereof.
15. The compound of claim 10, wherein said compound is selected from the group consisting of:
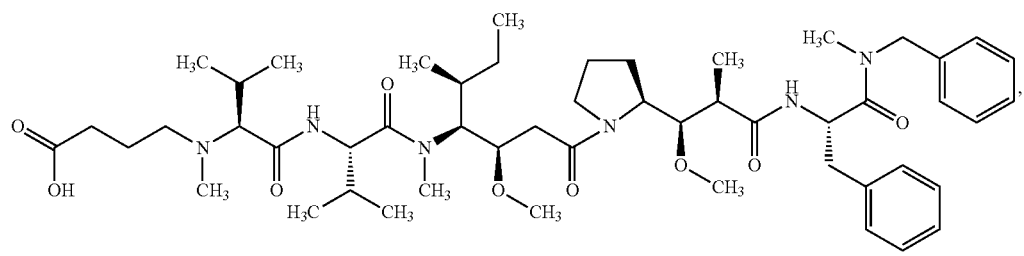
,
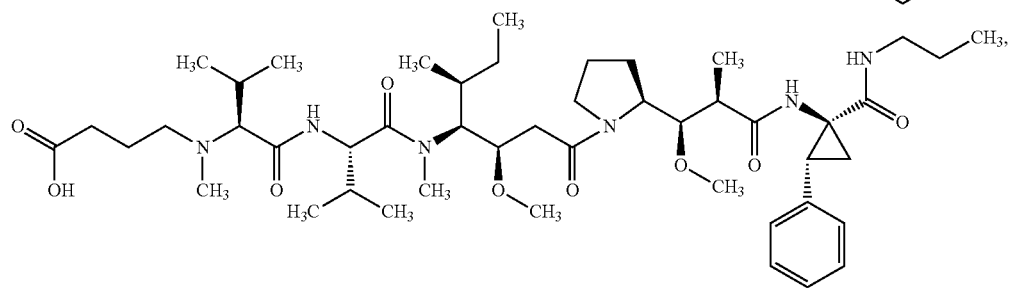
,
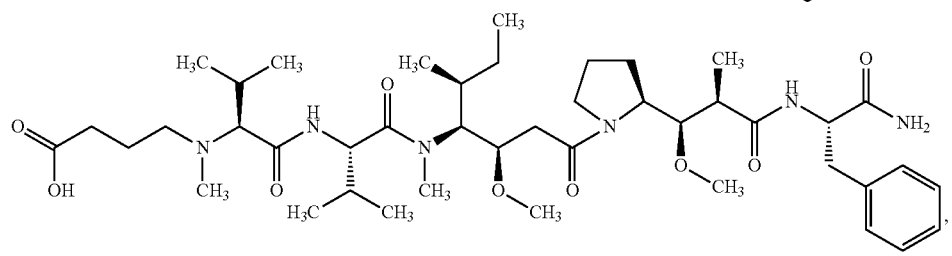
,
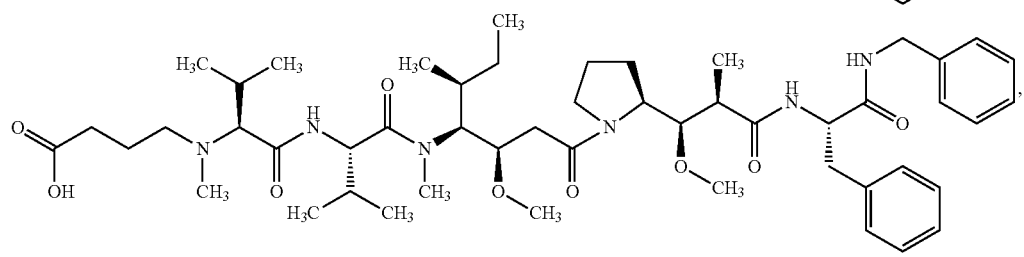
, -continued
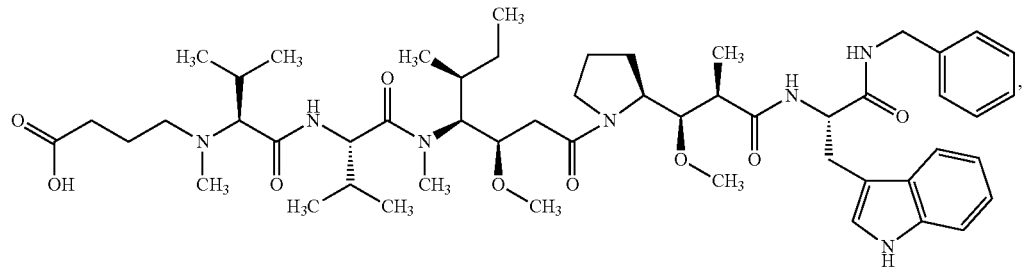
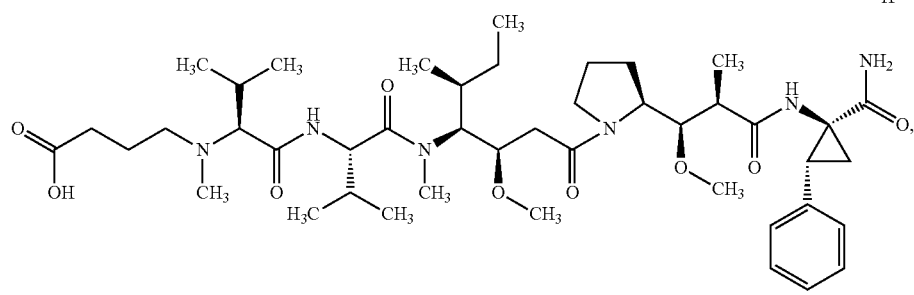
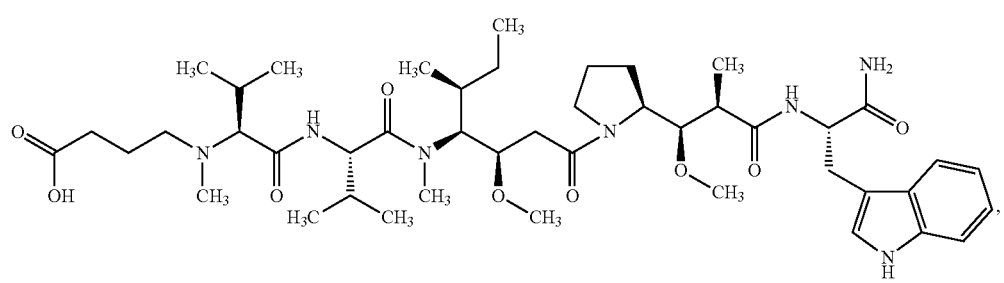
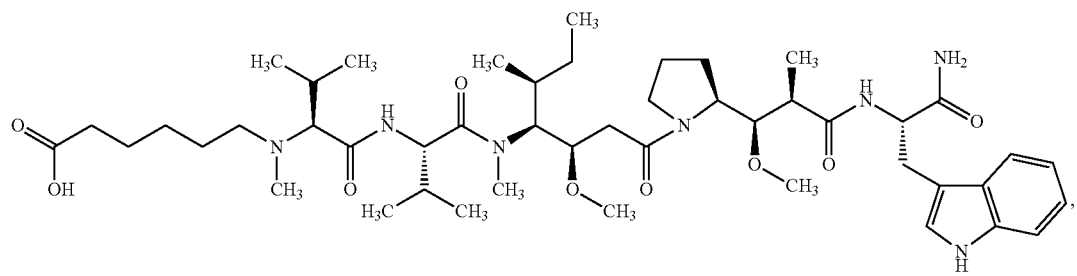
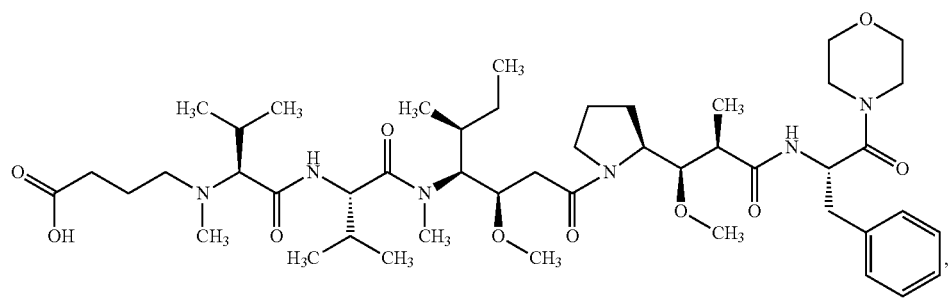
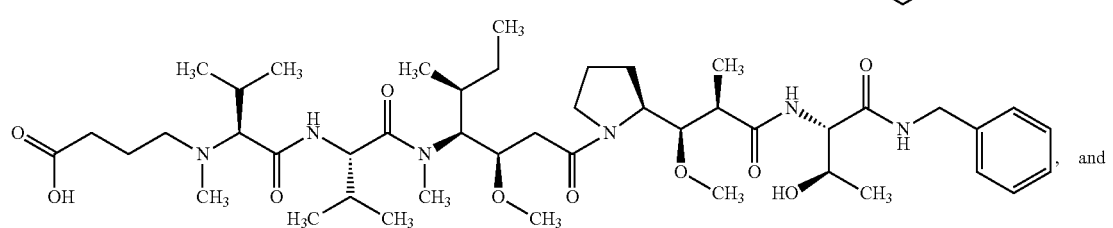, and -continued
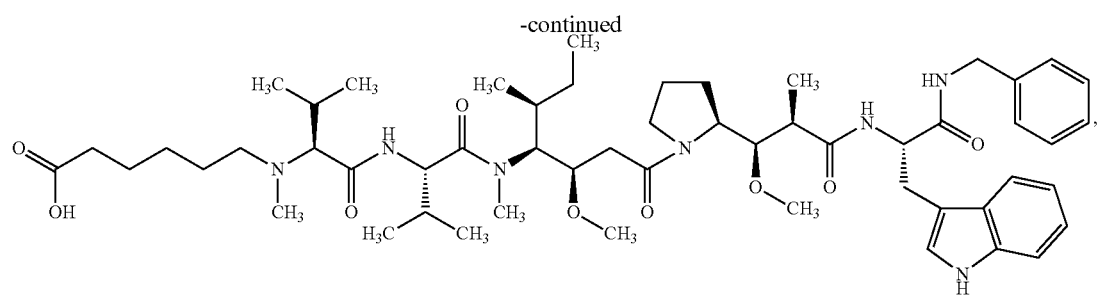
or a salt or solvate thereof.
16. The compound of claim 14, wherein the compound is
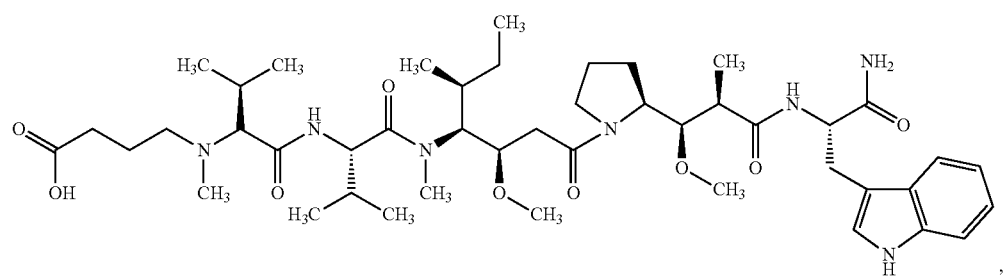
or a salt or solvate thereof.
* * * * *